US012599670B2

(12) United States Patent
Cullen

(10) Patent No.: US 12,599,670 B2
(45) Date of Patent: Apr. 14, 2026

(54) COMPOSITION COMPRISING THREE-DIMENSIONAL ASTROCYTE BUNDLES OF BI-POLAR AND ALIGNED ASTROCYTE PROCESSES AND A METHOD OF MAKING THEREOF

(71) Applicant: THE TRUSTEES OF THE UNIVERSITY OF PENNSYLVANIA, Philadelphia, PA (US)

(72) Inventor: D. Kacy Cullen, Media, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 15/534,934

(22) PCT Filed: Dec. 11, 2015

(86) PCT No.: PCT/US2015/065353
§ 371 (c)(1),
(2) Date: Jun. 9, 2017

(87) PCT Pub. No.: WO2016/094850
PCT Pub. Date: Jun. 16, 2016

(65) Prior Publication Data
US 2017/0368180 A1　　Dec. 28, 2017

Related U.S. Application Data

(60) Provisional application No. 62/091,245, filed on Dec. 12, 2014.

(51) Int. Cl.
| | |
|---|---|
| *A61K 47/36* | (2006.01) |
| *A61K 9/00* | (2006.01) |
| *A61K 35/30* | (2015.01) |
| *A61P 25/00* | (2006.01) |
| *C12N 5/00* | (2006.01) |
| *C12N 5/06* | (2006.01) |
| *C12N 5/07* | (2010.01) |
| *C12N 5/079* | (2010.01) |
| *C12N 5/0793* | (2010.01) |

(52) U.S. Cl.
CPC ............ *A61K 47/36* (2013.01); *A61K 9/0024* (2013.01); *A61K 35/30* (2013.01); *A61P 25/00* (2018.01); *C12N 5/0068* (2013.01); *C12N 5/06* (2013.01); *C12N 5/0618* (2013.01); *C12N 5/0619* (2013.01); *C12N 5/0622* (2013.01)

(58) Field of Classification Search
CPC ...... A61K 35/30; A61K 47/36; A61K 9/0024; A61K 2300/00; A61K 38/17; A61L 27/3604; A61L 27/3675; A61L 2300/412; A61L 2300/604; A61L 2300/606; A61L 2300/64; A61L 2420/00; A61L 2420/06; A61L 2430/32; A61L 27/20; A61L 27/225; A61L 27/227; A61L 27/24; A61L 27/26; A61L 27/34; A61L 27/3878; A61L 27/52; A61L 27/54; A61L 27/58; A61L 31/047; A61L 31/10; A61L 31/14; A61L 31/16; C12N 5/0622; C12N 2533/52; C12N 2533/56; C12N 2533/76; C12N 2533/78; C12N 2533/80; C12N 2533/90; C12N 5/0619; C12N 11/04; C12N 2502/08; C12N 2506/1392; C12N 2510/02; C12N 2510/04; C12N 2533/54; C12N 2533/72; C07K 14/435; C07K 14/47; A61F 2002/30062; A61F 2002/30199; A61F 2210/0004; A61F 2230/0063; A61M 2210/0693; A61N 1/05; A61N 1/375; B29C 55/22; B29K 2067/043; B29K 2067/046; B29K 2295/0056; C12M 25/10; C12M 29/16
See application file for complete search history.

(56) References Cited

U.S. PATENT DOCUMENTS

| | | | | |
|---|---|---|---|---|
| 5,061,281 A | * | 10/1991 | Mares | ................ A61B 17/1128 424/426 |
| 5,358,475 A | * | 10/1994 | Mares | ................ A61B 17/1128 523/113 |
| 6,171,610 B1 | * | 1/2001 | Vacanti | .................... A61F 2/28 424/426 |
| 6,264,944 B1 | | 7/2001 | Smith et al. | |

(Continued)

FOREIGN PATENT DOCUMENTS

| | | |
|---|---|---|
| JP | 2009506836 | 2/2009 |
| WO | 2011102991 A1 | 8/2011 |

(Continued)

OTHER PUBLICATIONS

Yucel et al. Biomacromolecules, 2010; 11:3584-3591.*

(Continued)

*Primary Examiner* — Chang-Yu Wang
(74) *Attorney, Agent, or Firm* — Saul Ewing LLP; Kathryn Doyle; Justin Crotty

(57) ABSTRACT
The invention includes a composition comprising an astrocyte comprising aligned and elongated astrocyte processes resulting from ex vivo machine-driven, physical stretching of the astrocyte maintained in culture, as well as a method of making it. The invention also includes a composition comprising an astrocyte comprising aligned bi-polar processes resulting from growth within hydrogel micro-columns in culture, as well as a method of making it. The invention also provides methods of treatment of nervous system injury or degeneration by implanting the compositions of the invention.

25 Claims, 22 Drawing Sheets

(56) References Cited

U.S. PATENT DOCUMENTS

| | | | |
|---|---|---|---|
| 6,365,153 B2 | 4/2002 | Smith et al. | |
| 6,461,629 B1 | 10/2002 | Tranquillo | |
| 6,548,569 B1 | 4/2003 | Williams | |
| 7,338,517 B2 | 3/2008 | Yost | |
| 7,429,267 B2 | 9/2008 | Smith et al. | |
| 8,401,635 B2 | 3/2013 | Smith | |
| 8,497,017 B2 | 7/2013 | Ohrlander | |
| 8,685,634 B2 | 4/2014 | Boruch | |
| 8,747,880 B2 | 6/2014 | Forgacs | |
| 9,139,935 B2* | 9/2015 | Chen | B01D 69/08 |
| 9,386,990 B2 | 7/2016 | Muir | |
| 9,556,415 B2 | 1/2017 | Forgacs | |
| 9,572,909 B2* | 2/2017 | Simpson | A61L 27/18 |
| 9,713,521 B2* | 7/2017 | Chen | D01D 5/0076 |
| 9,717,761 B2 | 8/2017 | Pitaru | |
| 9,737,635 B2 | 8/2017 | Brown | |
| 9,820,747 B2* | 11/2017 | Siemionow | A61B 17/1128 |
| 10,179,192 B2 | 1/2019 | Brown | |
| 10,617,300 B2 | 4/2020 | Rogers | |
| 10,772,989 B2 | 9/2020 | Brown | |
| 11,060,066 B2 | 7/2021 | Thomson | |
| 2001/0031974 A1 | 10/2001 | Hadlock | |
| 2001/0038835 A1 | 11/2001 | Smith et al. | |
| 2002/0168338 A1 | 11/2002 | Baird | |
| 2003/0049839 A1* | 3/2003 | Romero-Ortega | C12N 5/0068 |
| | | | 435/397 |
| 2003/0059933 A1 | 3/2003 | Tresco et al. | |
| 2004/0101518 A1* | 5/2004 | Vacanti | A61F 2/28 |
| | | | 424/93.7 |
| 2006/0292187 A1 | 12/2006 | Smith | |
| 2007/0010831 A1* | 1/2007 | Romero-Ortega | |
| | | | A61B 17/1128 |
| | | | 606/152 |
| 2007/0060815 A1 | 3/2007 | Martin | |
| 2007/0067883 A1 | 3/2007 | Sretavan | |
| 2007/0100358 A2* | 5/2007 | Romero-Ortega | |
| | | | A61B 17/1128 |
| | | | 606/152 |
| 2007/0155010 A1 | 7/2007 | Farnsworth | |
| 2008/0014631 A1 | 1/2008 | Muraguchi | |
| 2008/0022660 A1 | 1/2008 | Reuter | |
| 2008/0226609 A1 | 9/2008 | Proschel | |
| 2008/0292187 A1 | 11/2008 | Eitan | |
| 2008/0300691 A1 | 12/2008 | Romero-Ortega | |
| 2009/0222067 A1 | 9/2009 | Toselli | |
| 2010/0028436 A1 | 2/2010 | Ohrlander | |
| 2010/0226895 A1 | 9/2010 | Boruch | |
| 2011/0087338 A1* | 4/2011 | Siemionow | A61B 17/1128 |
| | | | 623/23.72 |
| 2011/0105998 A1 | 5/2011 | Zhang | |
| 2011/0212501 A1 | 9/2011 | Yoo et al. | |
| 2011/0263504 A1 | 10/2011 | Cerami | |
| 2011/0264235 A1* | 10/2011 | Chen | B01D 69/08 |
| | | | 623/23.72 |
| 2011/0300598 A1 | 12/2011 | Smith | |
| 2012/0128636 A1 | 5/2012 | Le | |
| 2012/0184035 A1 | 7/2012 | Agarwal | |
| 2012/0221025 A1* | 8/2012 | Simpson | A61L 27/18 |
| | | | 606/152 |
| 2013/0046134 A1 | 2/2013 | Parker | |
| 2013/0110138 A1* | 5/2013 | Hurtado | A61L 27/18 |
| | | | 606/152 |
| 2013/0171116 A1 | 7/2013 | Shoham | |
| 2014/0024116 A1 | 1/2014 | Subramanian | |
| 2014/0050704 A1 | 2/2014 | Kumar et al. | |
| 2014/0051168 A1 | 2/2014 | Vukasinovic et al. | |
| 2014/0308256 A1 | 10/2014 | Lu | |
| 2014/0371564 A1 | 12/2014 | Anikeeva | |
| 2015/0024025 A1* | 1/2015 | Floyd | A61L 27/54 |
| | | | 424/425 |
| 2015/0202351 A1* | 7/2015 | Kaplan | A61B 5/0478 |
| | | | 607/116 |
| 2015/0342719 A1* | 12/2015 | Chen | D01D 5/0076 |
| | | | 623/23.72 |

| | | |
|---|---|---|
| 2015/0352153 A1 | 12/2015 | Smith |
| 2016/0040961 A1 | 2/2016 | Kovalev |
| 2016/0245788 A1 | 8/2016 | Wang |
| 2016/0250385 A1 | 9/2016 | Cullen |
| 2017/0007824 A1 | 1/2017 | Gardner |
| 2017/0368180 A1 | 12/2017 | Cullen |
| 2018/0214492 A1 | 8/2018 | Smith |
| 2018/0256647 A1 | 9/2018 | Bitar |
| 2019/0126043 A1 | 5/2019 | Cullen |
| 2019/0269755 A1 | 9/2019 | Pruneau |
| 2020/0063099 A1 | 2/2020 | Feyeux |
| 2020/0208105 A1 | 7/2020 | Zimmermann |
| 2020/0237867 A1 | 7/2020 | Romero-Ortega |
| 2021/0393960 A1 | 12/2021 | Cullen |

FOREIGN PATENT DOCUMENTS

| | | |
|---|---|---|
| WO | 2013002953 A1 | 1/2013 |
| WO | 2015066627 A1 | 5/2015 |
| WO | 2016040961 A1 | 3/2016 |
| WO | 2016176333 A1 | 11/2016 |
| WO | 2017145163 A1 | 8/2017 |
| WO | 2017181068 A1 | 10/2017 |
| WO | 2019071106 | 4/2019 |
| WO | 2022182723 A1 | 9/2022 |

OTHER PUBLICATIONS

Weightman et al. NanoMed Nanotechnol. Bio. Med. 2014; 10:291-295 published online on Oct. 1, 2013; doi.org/10.1016/j.nano2013.09.001.*

East et al. Tissue Eng. Part A, 2010; 16:3173-3184.*

Cullen et al. Tissue Eng. Part A, 2012; 18:2280-2289.*

Abbott, Chapter 8, p. 189-208 of the book: Blood-Brain Interfaces: From Ontogeny to Artificial Barriers edited by R. Dermietzel, D.C. Spary and M. Nedergaard, Wiley-VCH Verlag GmbH & Co. KGaA, Weinheim. 2006.*

Balasubramanian et al. Tissue Engineering: PartA, 2016; 22:885-898.*

Brown et al. Adv. Funct. Mat. 2005; 15:1762-1770.*

Lau et al. J. Neurochem. 2014:130:215-226.*

Tibbitt et al., Biotechnol. Bioeng. 2009; 103:655-663.*

Ng et al., RSC Advances; 2012; 2:10110-10124.*

Watson et al. SLAS Discovery, 2017; 22:583-601.*

Abbott , Chapter 8, The Bipolar Astrocyte: Polarized Features of Astrocytic Glia Underlying Physiology, with Particular Reference to the Blood-Brain Barrier. Book: Blood-Brain Interfaces: From Ontogeny to Artificial Barrier, Edited by Dermietzel et al., 2006, Wiley-VCH Verlag GmbH & Co. KGaA, Weinhem.*

Peng et al, Chapter 13, Astrocyte Polarization and Wound Healing in Culture: Studying Cell Adhesion Molecules. Book: Astrocytes: Methods and Protocols, Methods in Molecular Biology, vol. 814, DOI 10.1007/978-1-61779-452-0_13, Springer Science+Business Media, LLC 2012.*

Fedoroff and Richardson edited, Book: Protocols for neural cell culture, 2nd edition, 1997, Springer Science Business Media New York.*

The catalog of surface area for corning cell culture vessels from the Corning website:www.corning.com/catalog/cls/documents/application-notes/CLS-AN-209.pdf, retrieved on Aug. 31, 2020.*

Yang et al. Cytotechnology, 2006; 52:87-97.doi 10.1007/s10616-006-9033-4.*

International Search Report and Written Opinion for PCT International Application No. PCT/US2015/065353 issued Mar. 7, 2016.

Cullen, et al., In vitro neural injury model for optimization of tissue-engineered constructs, J. Neurosci Res. 85(16),2007, 3642-3651 (Abstract Only).

Lau, et al., 3D Electrospun scaffolds promote a cytotrophic phenotype of cultured primary astrocytes, J Neurochem. 130(2),2014,215-226.

Mccarthy, et al., Preparation of separate astroglial and oligodendroglial cell cultures from rat cerebral tissue, J Cell Biol. 85(3),1980,890-902.

(56)             References Cited

OTHER PUBLICATIONS

Shimizu, et al., Cell sheet engineering for myocardial tissue recon-struction, Biomaterials. 24(13) ,2003 ,2309-2316.
Smith, et al., Stretch Growth of Integrated Axon Tracts: Extremes & Exploitations, Progress in Neurobiology 89(3) ,2009 ,231-239.
Struzyna, el al., Living scaffolds for neuroregeneration, Curr Opin Solid State Mater Sci. 18(6) ,2014 ,308-318.
Zheng, et al., Tensile regulation of axonal elongation and initiation, J Neurosci. 11(4) , 1991 , 1117-1125.
Barbour, et al., "Supercharged End-to-Side Anterior Interosseous to Ulnar Motor Nerve Transfer for Intrinsic Musculature Reinnerva-tion", J Hand Surg. 37(10), 2012, 2150-2159.
Farber, et al., "Supercharge Nerve Transfer to Enhance Motor Recovery", J Hand Surg. 38(3), 2013, 466-477.
Gordon, et al., "Accelerating Axon Growth to Overcome Limita-tions in Functional Recovery after Peripheral Nerve Injury", Neu-rosurgery 65(4), 2009, A132-A144.
Gordon, et al., "Brief electrical stimulation accelerates axon regen-eration in the peripheral nervous system and promotes sensory axon regeneration in the central nervous system", Motor Control 13(4), 2009, 412-441.
Gordon, et al., "The Basis for Diminished Functional Recovery after Delayed Peripheral Nerve Repair", J Neurosci. 31(14), 2011, 5325-5334.
Gordon, "The physiology of neural injury and regeneration: The role of neurotrophic factors", J Commun Disord. 43(4), 2010, 265-273.
Ladak, et al., "Side-to-side nerve grafts sustain chronically denervated peripheral nerve pathways during axon regeneration and result in improved functional reinnervation", Neurosurgery 68(6), 2011, 1654-1666.
Midha, et al., "Regeneration into Protected and Chronically Denervated Peripheral Nerve Stumps", Neurosurgery 57(6), 2005, 1289-1299.
Scholz, et al., "Peripheral nerve injuries: An international survey of current treatments and future perspectives", J Reconstructive Micro-surgery 25(6), 2009, 339-344.
Sulaiman, et al., "Role of Chronic Schwann Cell Denervation in Poor Functional Recovery after Nerve Injuries and Experimental Strategies to Combat It", Neurosurgery 65(4), 2009, A105-A114.
Pfister, et al., "Development of transplantable nervous tissue con-structs comprised of stretch-grown axons", J Neurosci Methods. 153(1), 2006, 95-103.
Jiang et al., "Stem Cell Transplantation for Peripheral Nerve Regen-eration: Current Options and Opportunities," Int J Mol Sci. Jan. 5, 2017;18(1). pii: E94.
Cullen et al., "Collagen-Dependent Neurite Outgrowth and Response to Dynamic Deformation in 3D Neuronal Cultures," Ann. Biomed. Engin., May 2007; 35(5):835-846.
Xu et al., "Electrophysiological characterization of embryonic hip-pocampal neurons cultured in a 30 collagen hydrogel," Biomaterials 2009; 30:4377-4383.
Struzyna et al., "Tissue Engineered Nigrostriatal Pathway for Treat-ment of Parkinson's Disease," J. Tissue Engin. & Regen. Med. 2018; 12:1702-1716.
Henstridge et al., "Beyond the neuron-cellular interactions early in Alzheimer disease pathogenesis," Nat. Rev. Neurosci. 2019; 20:94-107.
Anger, "Animal Test Systems to Study Behavioral Dysfunctions of Neurodegenerative Disorders," (p. 403, abstract, Neurotoxicology, 1991; 12:403-13.
Blight, "Miracles and molecules—progress in spinal cord repair," Nat. Neurosci. 2002. 5: 1051-4.
Schmidt et al., "Neural Tissue Engineering: Strategies for Repair and Regeneration," Annu. Rev. Biomed. Eng. 2003. 5: 293-347.
Hoke et al., "Mechanisms of Disease: what factors limit the success of peripheral nerve regeneration in humans?" Nat. Clin. Pract. Neurol. 2006: 448-454.
Belal, et al., "Pathology as it relates to ear surgery II. Labyrinthectomy", J Laryngol Otol, 97(1), 1983, 1-10.

Borisoff, et al., "Suppression of Rho-kinase activity promotes axonal growth on inhibitory CNS substrates", Mol Cell NeurOsci, 22(3), 2003, 405-416.
Cheng, et al., "Clinical progression in Parkinson disease and the neurobiology of axons", Ann Neurol, 67(6), 2010, 715-725.
Cullen, D. K., et al., "Microtissue Engineered Constructs with Living Axons for Targeted Nervous System Reconstruction", Tissue Engineering: Part A, vol. 18(21,22), 2012, 2280-2289.
Curinga, et al., "Molecular/genetic manipulation of extrinsic axon guidance factors for CNS repair and regeneration", Exp Neurol, 209(2), 2008, 333-342.
Denham, et al., "Neurons derived from human embryonic stem cells extend long-distance axonal projections through growth along host white matter tracts after intra-cerebral transplantation", Front Cell Neurosci 6, 2012,11.
Diamond, et al., "'Where' and 'what' in the whisker sensorimotor system", Nat Rev Neurosci, 9(8), 2008, 601-612.
Fawcett, "Dopaminergic neuronal survival and the effects of bFGF in explant, three dimensional and monolayer Cultures of embryonic rat ventral mesencephalon", Exp Brain Res, 106(2), 1995,275-282.
Filous, et al., "Immature astrocytes promote CNS axonal regenera-tion when combined with chondroitinase ABC", Dev Neurobiol, 70(12), 2010, 826-841.
Hennink, et al., "Novel crosslinking methods to design hydrogels", Adv. Drug Del. Rev. 54,2002,13-36.
Hoffman, "Hydrogels for biomedical applications", Adv. Drug Del. Rev. 43,2002, 3-12.
Huebner, et al., "Axon regeneration in the peripheral and central nervous systems", Results Probl Cell Differ 48, 2009, 339-351.
Hwang, et al., "Chondrogenic Differentiation of Human Embryonic Stem Cell-Derived Cells in Arginine-Glycine-Aspartate-Modified Hydrogels", Tissue Eng. 12, 2006, 2695-706.
Ifkovits, et al., "Review: Photopolymerizable and Degradable Biomateri-als for Tissue Engineering Applications", Tissue Eng. 13(10), 2007, 2369-85.
Kim, et al., "Association between sociability and diffusion tensor imaging in BALB/cJ mice", NMR in Biomedicine, 25 1), 2012, 104-112.
Kim, et al., "Enhanced delineation of white matter structures of the fixed mouse brain using Gd-DTPA in microscopic MRI", NMR in Biomedicine, 22(3), 2009, 303-309.
Kunze, et al., "Micropatterning neural cell cultures in 3D with a multi-layered scaffold", Biomaterials, 32(8), 2011, 2088-2098.
Lavallee, "Feedforward Inhibitory Control of Sensory Information in Higher-Order Thalamic Nuclei", J Neurosci, 25 33), 2005, 7489-7498.
Learoyd, et al., "Comparison of rat sensory behavioral tasks to detect somatosensory morbidity after diffuse brain-injury", Behav Brain Res, 226(1), 2012, 197-204.
Levin, et al., "A clinicopathologic study of optic neuropathies associated with intracranial mass lesions with quantification of remaining axons.", Am J Ophthalmol, 95(3), 1983,295-306.
Marshall, et al., "Deep white matter infarction: correlation of MR imaging and histopathologic findings", Radiology, 167(2), 1988, 517-522.
Masri, et al., "Zona Incerta: A Role in Central Pain", J Neurophysiol, 102(1), 2009, 181-191.
Mcnamara, et al., "The Whisker Nuisance Task Identifies a Late-Onset, Persistent Sensory Sensitivity in Diffuse Brain-Injured Rats", J Neurotrauma, 27(4), 2010, 695-706.
Melzer, et al., "Stimulus Frequency Processing in Awake Rat Barrel Cortex", J Neuorsci, 26(47), 2006, 12198-12205.
Millet, et al., "Guiding neuron development with planar surface gradients of substrate cues deposited using microfluidic devices", Lab Chip, 10(12), 2010, 1525-1535.
Mine, et al., "Grafted human neural stem cells enhance several steps of endogenous neurogenesis and improve behavioral recovery after middle cerebral artery occlusion in rats", Neurobiol Dis 52:, 2013, 191-203.
Nam, et al., "Multichannel recording and stimulation of neuronal cultures grown on microstamped poly-D-lysine", Conf Proc IEEE Eng Med Biol Soc. 6:, 2004, 4049-52.

(56) References Cited

OTHER PUBLICATIONS

Nguyen, et al., "Photopolymehzable hydrogels for tissue engineering applications", Biomaterials 23(22), 2002, 4307-14.

O'Connor, et al., "Survival and neurite outgrowth of rat cortical neurons in three-dimensional agarose and collagen gel matrices", Neurosci Lett, 304(3), 2001,189-193.

Qiu, et al., "Photoreceptor differentiation and integration of retinal progenitor cells transplanted into transgenic rats", Exp Eye Res, 80(4), 2005, 515-525.

Ren, et al., "Intracerebral neural stem cell transplantation improved the auditory of mice with presbycusis", Int J Clin Exp Pathol 6(2), 2013, 230-241.

Shin, "Biomimetic materials for tissue engineering", Biomaterials 24, 2003, 4353-4364.

Sinclair, et al., "Dopamine cells in nigral grafts differentiate prior to implantation", Eur J Neurosci 11(12), 1999, 4341-4348.

Smith, et al., "High Tolerance and Delayed Elastic Response of Cultured Axons to Dynamic Stretch Injury", J NeurOsci 19(11), 1999, 4263-4269.

Sorribas, et al., "Photolithographic generation of protein micropatterns for neuron culture applications", Biomaterials, 23(3):, 2002, 893-900.

Tallantyre, et al., "Clinico-pathological evidence that axonal loss underlies disability in progressive multiple sclerosis", Mult Scler, 16(4), 2010, 406-411.

Tate, et al., "Fibronectin Promotes Survival and Migration of Primary Neural Stem Cells Transplanted Into the Traumatically Injured Mouse Brain", Cell Transplant 11 (3), 2002, 283-295 (abstract only).

Tate, et al., "Laminin and fibronectin scaffolds enhance neural stem cell transplantation into the injured brain", J Tissue Eng Regen Med 3(3), 2009, 208-217.

Thomas, et al., "Hypersensitive Glutamate Signaling Correlates with the Development of Late-Onset Behavioral Morbidity in Diffuse Brain-Injured Circuitry", J Neurotrauma, 29(2):, 2012, 187-200.

Wheeler, et al., "Patterning to influence in vitro neuronal interfaces", Conf Proc IEEE Eng Med Biol Soc 7,2004, 6337-5339.

Woerly, et al., "Cultured rat neuronal and glial cells entrapped within hydrogel polymer matrices: a potential tool for neural tissue replacement", Neurosci Lett, 205(3), 1996, 197-201.

Yoo, et al., "Simple and Novel Three Dimensional Neuronal Cell Culture Using a Micro Mesh Scaffold", Exp Neurobiol 20(2), 2011, 110-115.

BRAIN Initiative Investigators Pre-Meeting: Large Scale Recording and Modulation, Dec. 9, 2015, Rockville, MD.

Extended European Search Report for European Patent Application No. 17783279.7 issued Oct. 11, 2019.

International Search Report and Written Opinion for PCT/US2017/027705 issued Sep. 1, 2017.

Abate, T., et al., "Stanford engineers create artificial skin that can send pressure sensation to brain cell," Stanford Report, Oct. 15, 2015,4 pages.

Anikeeva, P., et al.,"Flexible Optoelectronic Devices for Neural Recording and Stimulation", Flexible Electronics Session, NAE USFOE, 2013, 13 pages.

Aregueta-Robles, UA et al., "Organic electrode coatings for next-generation neural interfaces", Frontiers in Neuroengineering, (May 27, 2014), pp. 1-18, XP055158449.

Chen, H. I., et al., "Neural Substrate Expansion for the Restoration of Brain Function", Frontiers in Systems Neuroscience, vol. 10(1), Jan. 2016, 9 pages.

Choi, ML , et al., "Light-guiding hydrogels for cell-based sensing and optogerietic synthesis In vivo", Nat Photonics, 7, 2013,987-994.

Colapinto, J., et al., "Lighting the Brain", Profiles, May 18, 2015,16 pages.

Deisseroth, K., et al., "Engineering Approaches to Illuminating Brain Structure and Dynamics", Neuron 80, Oct. JO, 2013, pp. 568-577.

Jeong, J., et al., "Soft Materials in Neuroengineering for Hard Problems in Neuroscience," Neuron 86, Apr. 8, 2015, pp. 175-186.

Long, X. , et al., "Magnetogenetics: remote non-invasive magnetic activation of neuronal activity with a magnetoreceptor", Science Bulletin 60(24), Dec. 2015, 2107-2119.

NIH , "Biological 'Living Electrodes' using Tissue Engineered Axonal Tracts to Probe and Modulate the Nervous System", NIH Research Portfolio Online Reporting Tools (RePORT), Dec. 29, 2015, 1 page.

Smith, K. , "Method Man—Karl Deisseroth is leaving his mark on brain science one technique at a time", Nature, vol. 497, May 30, 2013, 550-552.

Struzyna, L. A., et al., "Restoring nervous system structure and function using tissue engineered living scaffolds", Neural Regeneration Research, vol. 10(5), May 2015, pp. 679-685.

Tang-Schomer, M. D., et al., "Bioengineered functional brain-like cortical tissue", PNAS, vol. 111 (38), Sep. 23, 2014, 13811-13818.

International Search Report and Written Opinion, PCT/US2018/054576, dated Dec. 12, 2018.

Huang , et al., "Long-term survival and integration of transplanted engineered nervous tissue constructs promotes peripheral nerve regeneration", Tissue Eng Part A, 15(7), 1677-1685 (Jul. 2009) (Abstract only).

Loverde, Joseph R. , "Deciphering the biology of axon stretch-growth", New Jersey Institute of Technology, Digital Commons @ NJIT, Theses 297, submitted to the Faculty of New Jersey Institute of Technology, Jan. 2009, 63 pages.

Pfister , et al., "Extreme stretch growth of integrated axons", J Neurosci, 24(36), 7978-7983 (Sep. 2004).

Smith , et al., "A new strategy to produce sustained growth of central nervous system axons: continuous mechanical tension", Tissue Eng 7, 131-139 (2001) (Abstract only).

International Search Report and Written Opinion dated Apr. 14, 2020, PCT/US19/60585.

Czajka , et al., "Implanted scaffold-free prevascularized constructs promote tissue repair", Ann Plast Surg., Mar. 2015; 74(3): 371-375.

Graber , et al., "Purification and Culture of Spinal Motor Neurons from Rat Embryos", Downloaded from http://cshprotocols.cshlp.org/on Jul. 26, 2021—Published by Cold Spring Harbor Laboratory Press.

Katiyar , et al., "Stretch-Growth of Motor Axons in Custom Mechanobioreactors to Generate Long-Projecting Axonal and Axonal-Myocyte Constructs", bioRxiv, preprint doi: https://doi.Org/10.1101/598755; Apr. 4, 2019.

Kimura , et al., "Development, Maturation, and Transdifferentiation of Cardiac Sympathetic Nerves", Circ Res. Jan. 20, 2012;110(2):325-36, doi: 10.1161/CIRCRESAHA.111.257253. PMID: 22267838.

Kreipke , et al., "Innervating sympathetic neurons regulate heart size and the timing of cardiomyocyte cell cycle withdrawal", J Physiol 593.23 (Sep. 2015) pp. 5057-5073.

O'Donnell , et al., "A tissue-engineered rostral migratory stream for directed neuronal replacement", Neural Regeneration Research, Aug. 2018, vol. 13, No. 8, pp. 1327-1331.

Oh , et al., "Functional Coupling with Cardiac Muscle Promotes Maturation of hPSC-Derived Sympathetic Neurons", Cell Stem Cell, 19, 95-106, Jul. 7, 2016.

Potter , et al., "Synaptic Functions in Rat Sympathetic Neurons in Microcultures. II. Adrenergic/Cholinergic Dual Status and Plasticity", The Journal of Neuroscience, Apr. 1986, vol. 6, No. 4, pp. 1080-1098.

Rodell , et al., "Injectable and Cytocompatible Tough Double Network Hydrogels through Tandem Supramolecular and Covalent Crosslinking", Adv Mater., Oct. 2016; 28(38): 8419-8424. doi:10.1002/adma.201602268.

Serruya , et al., "Cardiac myocyte microtissue aggregates broadcast local field potentials", bioRxiv, preprint doi: https://doi.org/10.1101/376418; Jul. 25, 2018.

Struzyna , et al., "Rebuilding Brain Circuitry with Living Micro-Tissue Engineered Neural Networks", Tissue Engineering: Part A, vol. 21, Nos. 21 and 22, 2015.

Das, Suradip, et al., "Innervation: the missing link for biofabricated tissues and organs", Regenerative Medicine (2020) 5:11 ; https://doi.org/10.1038/s41536-020-0096-1.

(56)            References Cited

OTHER PUBLICATIONS

Das, Suradip, et al., "Pre-innervated tissue-engineered muscle promotes a pro-regenerative microenvironment following volumetric muscle loss", Communications Biology, (2020), 3:330, https://doi.org/10.1038/s42003-020-1056-4, www.nature.com/commsbio.

Ungrin , et al., "Reproducible, Ultra High-Throughput Formation of Multicellular Organization from Single Cell Suspension-Derived Human Embryonic Stem Cell Aggregates", PLoS One, Feb. 2008, vol. 3, Issue 2, e1565.

Vegh , et al., "Part and Parcel of the Cardiac Autonomic Nerve System: Unravelling Its Cellular Building Blocks during Development", J. Cardiovasc. Dev. Dis., Sep. 2016, 3, 28.

Zareen , et al., "Protocol for Culturing Sympathetic Neurons from Rat Superior Cervical Ganglia (SCG)", J. Vis. Exp. (23), e988, doi: 10.3791/988 (Jan. 2009).

International Search Report and Written Opinion issued in App. No. PCT/US2022/017470, mailing date Jun. 22, 2022, 13 pages.

International Search Report and Written Opinion issued in App. No. PCT/US22/32978, mailing date Oct. 27, 2022, 17 pages.

International Search Report and Written Opinion issued in App. No. PCT/US2022/029908, mailing date Oct. 27, 2022, 12 pages.

Adewole et al., "Development of optically controlled "living electrodes" with long-projecting axon tracts for a synaptic brain-machine interface", Science Advances, vol. 7, Jan. 22, 2021 [retrieved on Sep. 16, 2022]. Retrieved from the Internet: URL: https://www.science.org/doi/10.1126/sciadv.aay5347>. pp. 1-15.

Gordian-Velez et al., "Restoring lost nigrostriatal fibers in Parkinson's disease based on clinically-inspired design criteria", Brain Research Bulletin, vol. 175, Jul. 28, 2021, pp. 168-185.

International Search Report and Written Opinion issued in App. No. PCT/US2022/032146, mailing date Sep. 14, 2022, 15 pages.

Kim et al. "Gingiva-Derived Mesenchymal Stem Cells: Potential Application in Tissue Engineering and Regenerative Medicine—A Comprehensive Review", Frontiers in Immunology, Apr. 16, 2021, vol. 12, Article No. 667221, pp. 1-25.

Clark et al. "In Vivo Neural Tissue Engineering: Cylindrical Biocompatible Hydrogels That Create New Neural Tracts in the Adult Mammalian Brain", Stem Cells and Development, Jun. 2016, vol. 25, No. 15, pp. 1109-1118.

Purvis et al. "Tissue Engineering and Biomaterial Strategies to Elicit Endogenous Neuronal Replacement in the Brain", Frontiers in Neurology, Apr. 28, 2020, vol. 11, Article No. 344.

O'Donnell et al. "An Implantable Human Stem Cell-Derived Tissue-Engineered Rostral Migratory Stream for Directed Neuronal Replacement", Nature Communications Biology, Jul. 15, 2021, vol. 4, Article No. 879.

International Search Report and Written Opinion issued in App. No. PCT/US 2023/013385, mailing date May 2, 2023, 10 pages.

Extended European Search Report issued in App. No. EP23164337, dated Jun. 16, 2023, 9 pages.

EPO Communication pursuant to Aritcle 94(3) issued in App. No. EP17783279, dated Aug. 3, 2023, 5 pages.

McGill, The McGill Physiology Virutal Lab, Accessed Aug. 22, 2023, Available online at: www.medicine.cgill.ca/physio/vlab/other_exps CAP/nerve_anat.htm#:-:text=For%20example%2C%20the%20vagus%20nerve,ganglia%2C%20for%20sensory%20fibres.

* cited by examiner

A) Neuroanatomical and physiological inspiration: rostral migratory stream

B) *In vitro* micro-column fabrication and seeding

C) Future application: *In vivo* delivery

COMPOSITION COMPRISING THREE-DIMENSIONAL ASTROCYTE BUNDLES OF BI-POLAR AND ALIGNED ASTROCYTE PROCESSES AND A METHOD OF MAKING THEREOF

CROSS-REFERENCE TO RELATED APPLICATIONS

The present application is a 35 U.S.C. § 371 national phase application from, and claims priority to, International Application No. PCT/US2015/065353, filed Dec. 11, 2015, which claims priority under 35 U.S.C. § 119 (e) to U.S. Provisional Application No. 62/091,245, filed Dec. 12, 2014, all of which applications are incorporated herein by reference in their entireties.

STATEMENT REGARDING FEDERALLY SPONSORED RESEARCH OR DEVELOPMENT

This invention was made with government support under grant number W81XWH-13 awarded by the Department of Defense. The government has certain rights in the invention.

BACKGROUND OF THE INVENTION

Nervous system regeneration is a complex biological process. In the peripheral nervous system (PNS), nerves can regenerate on their own if the lesions are small. Large lesions must be surgically treated, normally using nerve grafts harvested from other parts of the body. However in the central nervous system (CNS), nerve cells rarely regenerate on their own, even in small lesions, because factors are present that inhibit repair and regeneration. Accordingly, efforts for repairing CNS injuries are focused on creating a permissive environment for regeneration.

Despite much research in creating a permissive environment for nervous system regeneration, there is a need in the art for the development of improved treatments for CNS injuries. The present invention satisfies this need.

SUMMARY OF THE INVENTION

The present invention includes a composition comprising an astrocyte comprising aligned and elongated astrocyte processes resulting from ex vivo machine-driven, physical stretching of the astrocyte maintained in culture, as well as a method of making it.

In one aspect, the invention includes a composition comprising three-dimensional astrocyte bundles of bi-polar and aligned astrocyte processes.

In another aspect, the invention includes a method of producing three-dimensional astrocyte bundles of bi-polar aligned astrocyte processes, comprising seeding a micro-column comprising a biocompatible matrix with a plurality of astrocytes; and culturing the micro-column so seeded in a culture medium.

In yet another aspect, the invention includes a composition comprising a three-dimensional bundle of aligned bi-polar astrocytes made by the method described herein.

In still another aspect, the invention includes a composition comprising an astrocyte comprising at least one aligned and elongated astrocyte processes having a length of at least 0.2 millimeter.

In another aspect, the invention includes a method of producing aligned and elongated astrocyte processes from an astrocyte comprising: a) culturing an astrocyte in a culture medium: b) plating the cultured astrocyte onto an overlying membrane and an underlying membrane so that the cultured astrocyte adheres to both membranes; and c) moving one of the two membranes—the overlying membrane and the underlying membrane-across the other under an ex vivo force at a rate of in the range of 0.1-0.5 millimeter/day so that astrocyte processes from the astrocyte are stretched and aligned along the ex vivo force.

In yet another aspect, the invention includes a composition comprising aligned and elongated astrocyte processes from an astrocyte, wherein the aligned and elongated astrocyte processes are made by the method described herein.

In various embodiments of the above aspects or any other aspect of the invention delineated herein, the astrocyte bundles are enclosed in a micro-column comprising a biocompatible matrix on the inner surface of the micro-column. In one such embodiment, the biocompatible matrix is a hydrogel selected from the group consisting of extracellular matrix, collagen, agarose, methylcellulose, biodegradable polyurethanes, and cross-linked hyaluronic acid. In another embodiment, the biocompatible matrix comprises collagen and the micro-column comprises agarose.

In one embodiment, the inner diameter of the micro-column is in the range of about 0.1 mm to about 0.9 mm. In another embodiment, the inner diameter of the micro-column is in the range of about 0.3 mm to about 0.35 mm. In yet another embodiment, the inner diameter of the micro-column is about 0.18 mm.

In another embodiment, the micro-column is seeded with astrocytes at a density in the range of $9\text{-}12\times10^5$ cells/ml. In yet another embodiment, the micro-column is co-seeded with neurons. In still another embodiment, the astrocytes so cultured are extracted from the micro-column.

In another embodiment, the culture medium comprises Neurobasal® (A neuronal culture medium for cultivating neuronal cells from hippocampus, cortex and other regions of the brain and containing no L-glutamine. L-glutamic acid, or aspartic acid), B27® supplement (a neuronal culture supplement comprising insulin, transferrin, progesterone, putrescine, selenium, thyroid hormone T3, fatty acids, and antioxidants including vitamin E and glutathione), G-5 supplement (a chemically defined serum free supplement based on Bottenstein's G-5 formulation for growth and expression of glial cells and astrocytes) and L-glutamine. In yet another embodiment, the weight percentage of B27® supplement (a neuronal culture supplement comprising insulin, transferrin, progesterone, putrescine, selenium, thyroid hormone T3, fatty acids, and antioxidants including vitamin E and glutathione) in the culture medium ranges from 1% to 5%. In yet another embodiment, the weight percentage of G-5 supplement (a chemically defined serum free supplement based on Bottenstein's G-5 formulation for growth and expression of glial cells and astrocytes) in the culture medium ranges from 0.1% to 3%. In still another embodiment, the weight percentage of L-glutamine in the culture medium ranges from 0.1% to 1.0%.

In another embodiment, the overlying membrane is the towing membrane and the underlying membrane is the stationary membrane. In yet another embodiment, the underlying membrane is the towing membrane and the overlying membrane is the stationary membrane. In still another embodiment, the towing membrane is coated with a biocompatible matrix. In another embodiment, the stationary membrane is coated with a biocompatible matrix. In yet another embodiment, the biocompatible matrix is a hydrogel selected from the group consisting of, extracellular matrix, MATRIGEL® (a gelatinous protein mixture), collagen, agarose, methylcellulose, biodegradable polyurethanes, and cross-linked hyaluronic acid. In yet another embodiment, the biocompatible matrix comprises MATRIGEL® (a gelatinous protein mixture).

In another embodiment, the ex vivo force is a mechanical force. In yet another embodiment, the mechanical force is generated from a stepper motor. In still another embodiment, the astrocyte processes are elongated greater than 1 millimeter in length. In another embodiment, the astrocyte processes are elongated greater than 2 millimeter in length.

In one aspect, the invention includes a method of treating a neurological disorder in a subject, comprising transplanting into a site for the neurological disorder the composition described herein.

In another aspect, the invention includes a method of treating a neurodegenerative condition in a subject, comprising transplanting into the brain of the subject the composition described herein.

In yet another aspect, the invention includes a method of treating a neurological disorder in a subject, comprising transplanting into the site for the neurological disorder the composition described herein.

In still another aspect, the invention includes a method of treating a neurodegenerative condition in a subject, comprising transplanting into the brain of the subject the composition described herein.

In various embodiments of the above aspects or any other aspect of the invention delineated herein, the neurological disorder is selected from the group consisting of nerve injury, spinal cord injury or brain injury, such as the brain injury is the result of a stroke or traumatic brain injury. In one embodiment, the neurodegenerative condition is Alzheimer's disease or Parkinson's disease.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 2, comprising FIGS. 2A-2B are confocal microscopy images of astrocytes in vivo from porcine cerebral cortex, stained using immunohistochemistry for glial-fibrillary acidic protein with Hoechst counterstain. FIG. 2C is a bright field microscopy image of astrocytes after 5 days in vitro culture on polystyrene with serum media (Dulbecco's Modified Eagle Medium: Nutrient Mixture F-12 (DMEM/F12)+10% Fetal bovine serum (FBS)). FIG. 2D is a bright field microscopy image of astrocytes 5 days in vitro on polystyrene with defined serum-free media (Neurobasal® (A neuronal culture medium for cultivating neuronal cells from hippocampus, cortex and other regions of the brain and containing no L-glutamine. L-glutamic acid, or aspartic acid)+2% B27® supplement (a neuronal culture supplement comprising insulin, transferrin, progesterone, putrescine, selenium, thyroid hormone T3, fatty acids, and antioxidants including vitamin E and glutathione)+1% G-5 supplement (a chemically defined serum free supplement based on Bottenstein's G-5 formulation for growth and expression of glial cells and astrocytes)+0.25% L-Glutamine).

FIG. 3, comprising FIG. 3A is a bright field microscopy image depicting astrocytes 5 days after in vitro culture (matrix pre-coated with poly-L-lysine) on polystyrene only. FIG. 3B is a bright field microscopy image depicting astrocytes 5 days after in vitro (matrix pre-coated with poly-L-lysine) culture on copolymer film, ACLAR® film (a clear, poly-chloro-trifluoroethylene (PCTFE) film), only. FIG. 3C is a bright field microscopy image depicting astrocytes 5 days in vitro (matrix pre-coated with poly-L-lysine), grown on 1 mg/mL gel matrix, MATRIGEL® (a gelatinous protein mixture), on copolymer film, ACLAR® film (a clear, poly-chloro-trifluoroethylene (PCTFE) film). FIG. 3D is a bright field microscopy image depicting astrocytes 5 days after in vitro (matrix pre-coated with poly-L-lysine) culture on 1 mg/mL rat tail collagen type I on copolymer film, ACLAR® film (a clear, poly-chloro-trifluoroethylene (PCTFE) film). All cultures were plated with defined media (Neurobasal® (A neuronal culture medium for cultivating neuronal cells from hippocampus, cortex and other regions of the brain and containing no L-glutamine. L-glutamic acid, or aspartic acid)+2% B27® supplement (a neuronal culture supplement comprising insulin, transferrin, progesterone, putrescine, selenium, thyroid hormone T3, fatty acids, and antioxidants including vitamin E and glutathione)+1% G-5 supplement (a chemically defined serum free supplement based on Bottenstein's G-5 formulation for growth and expression of glial cells and astrocytes)+0.25% L-Glutamine).

FIG. 4, comprising FIG. 4A is a bright field microscopy image depicting astrocytes cultured on 1 mg/mL collagen type I after 5 days of in vitro culture. FIG. 4B is a bright field microscopy image depicting astrocytes cultured on 1 mg/mL collagen type I after 20 days of in vitro culture. All cultures were plated with defined media (Neurobasal® (A neuronal culture medium for cultivating neuronal cells from hippocampus, cortex and other regions of the brain and containing no L-glutamine. L-glutamic acid, or aspartic acid)+2% B27® supplement (a neuronal culture supplement comprising insulin, transferrin, progesterone, putrescine, selenium, thyroid hormone T3, fatty acids, and antioxidants including vitamin E and glutathione)+1% G-5 supplement (a chemically defined serum free supplement based on Bottenstein's G-5 formulation for growth and expression of glial cells and astrocytes)+0.25% L-Glutamine).

FIG. 5, comprising FIG. 5A is a bright field microscopy image depicting astrocytes 1 day after in vitro culture on a collagen I coated interface between a thin copolymer film, ACLAR® 33C film (a clear, polychloro-trifluoroethylene (PCTFE) film, overlying membrane and a thicker copolymer film, ACLAR® film (a clear, poly-chloro-trifluoroethylene (PCTFE) film), underlying membrane with defined media (B27® supplement (a neuronal culture supplement comprising insulin, transferrin, progesterone, putrescine, selenium, thyroid hormone T3, fatty acids, and antioxidants including vitamin E and glutathione)+2% B27® supplement (a neuronal culture supplement comprising insulin, transferrin, progesterone, putrescine, selenium, thyroid hormone T3, fatty acids, and antioxidants including vitamin E and glutathione)+1% G-5 supplement (a chemically defined serum free supplement based on Bottenstein's G-5 formulation for growth and expression of glial cells and astrocytes)+0.25% L-Glutamine). The astrocytes grew along the entire overlying membrane. FIGS. 5B-5D are higher magnification images showing processes crossing the overlying membrane interface.

FIG. 8, comprising FIG. 8A is an image illustrating a custom-built mechano-bioreactor attached to a stepper motor in order to apply mechanical tension. FIG. 8B is a cross-section view of the mechano-bioreactor illustrating the towing membrane at its original position, outlined with a box. FIG. 8C is a cross-section view of the mechano-bioreactor illustrating the towing membrane at its extended position, outlined with a box. FIG. 8D is a cross-section view of the mechanobioreactor showing the towing membrane pulled back and the network of processes stretched due to the applied tension.

FIG. 17A1: this engineered "living scaffold" recapitulates the rostral migratory stream (RMS), which extends from the subventricular zone (SVZ)—a known stem cell niche—to the olfactory bulb. FIG. 17A2 shows a tract of aligned glial somata and processes on which developing neuroblasts migrate. FIG. 17B1: To emulate this anatomical pathway, a biomaterial scheme was employed featuring an agarose hydrogel micro-column of specified outer and inner diameters (generally 2-3 times the diameter of a human hair) coated with a bioactive collagenous matrix on the inner surface to promote cell adherence and survival. FIG. 17B2: Astrocytes were microinjected into the hydrogel micro-column, ultimately forming longitudinally aligned astrocytic somata and processes within the center of the micro-column (FIG. 17B3). FIG. 17C1: This micro-construct has the potential to physically bridge a glial scar/penumbra to provide a living labeled pathway to redirect migrating neuroblasts from a stem cell niche, such as the SVZ/RMS, (FIG. 17C2) to a site of focal injury.

(FIG. 19B) medium, and (FIG. 19C) high cell densities (N=15 micro-columns each). Micro-columns plated at high cell densities were found to consistently produce a robust network of longitudinally aligned astrocytes, whereas low and medium cell densities, although predominantly aligned, did not form such dense bundles. Scale bar: 200 µm.

FIGS. 20C, 20D: The robust, longitudinally aligned networks formed following seeding at a high density (N=21) were also virtually all of an anastrocytic phenotype. Scale bars FIGS. 20A, 20C, 20D: 100 µm: Scale bar FIG. 20B: 20 µm.

FIG. 21A: Astrocytes grown in a traditional planar culture environment on polystyrene exhibited an archetypal stellate morphology and (FIG. 21B) were solely of the astrocytic phenotype as confirmed by immunocytochemistry (GFAP, Hoechst). FIG. 21C: Alternatively, phase contrast images of astrocytes grown in hydrogel micro-columns of 350 µm (pictured) and 180 µm (not pictured) ID consistently formed a bipolar morphology nearly perfectly aligned with the central axis of the micro-column. FIG. 21D: The astrocytic phenotype of these bi-polar aligned cells was also confirmed by immunocytochemistry (GFAP, Hoechst). FIG. 21E: The effect of micro-column diameter on induction of bipolar morphology was quantified, as shown graphically as the percentage of bi-polar astrocytes for the various microcolumn/culture conditions. Micro-columns with an ID of 180 µm (n=121 astrocytes from N=6 microcolumns) or 350 µm (n=134; N=6) resulted in a significant increase in the presence of bi-polar astrocytes compared to 1 mm ID micro-columns (n=146 astrocytes; N=5) or 2-D sister cultures on polystyrene (n=102; N=5 cultures) (p<0.001 each). Error bars represent standard deviation. Scale bars FIGS. 21A, 21B: 100 µm: Scale bars FIGS. 21C, 21D: 20 µm.

(FIGS. 22A-22D) Bright field microscopy revealed that astrocytes plated at high density in hydrogel micro-columns of 350 µm ID formed a robust network of longitudinally aligned astrocytes that extended throughout the entire length of the micro-column (>5 mm). Confocal reconstructions of these dense bundles stained via immunocytochemistry to denote (FIGS. 22E, 22H) astrocyte somata/processes (GFAP) and (FIGS. 22F, 22I) Hoechst nuclear counterstain with (FIGS. 22G, 22J) overlay confirm that the longitudinal bundles were comprised of astrocytic somata and processes expressing GFAP throughout the entire length. These micro-columns were also immunostained with anti-β-tubulin-III to assess potential neuronal contamination, demonstrating a complete absence of neurons (not shown). Scale bars FIGS. 22A, 22E, 22F, 22G: 500 µm; Scale bars FIGS. 22B, 22C, 22D, 22H, 22I, 22J: 100 µm.

FIGS. 22C-22E show high-resolution confocal reconstructions of astrocyte bundles following extraction via immunocytochemistry (GFAP; DAPI), demonstrating bipolar morphology and alignment of astrocytes. Scale bars FIGS. 22A-22C: 500 µm; FIG. 22D: 100 µm; E: 50 µm.

FIG. 24A shows an astrocytic bundle extracted from a 20 mm micro-column and adhered to a poly-L-lysine coated coverslip in a swirl pattern. FIG. 24B shows higher magnification of a representative region demonstrating maintenance of astrocyte somata and process alignment following physical manipulation of extracted astrocyte bundles. Scale bars: 100 µm.

FIG. 25A: Astrocytes seeded in hydrogel micro-columns were spherical with a non-process bearing morphology as they adhered to the internal collagen matrix at 1 hour post-plating. FIG. 25B: As early as 1 day in vitro (DIV), the astrocytes appeared to remodel the collagen ECM and contracted to form dense bundles of longitudinally aligned astrocytes. FIG. 25C: Additional micro-columns were co-seeded with neurons (at 1 hour post astrocyte seeding); however, the presence of neurons did not inhibit the formation of dense longitudinally aligned astrocytes by 1 DIV. These results suggest that astrocytes dominate the mechanical environment and that co-seeding with neurons does not modulate the astrocytic behavior to remodel and contract the collagen ECM. Scale bar: 100 µm.

FIGS. 26A-26C: Representative confocal reconstructions of planar co-cultures grown on polystyrene revealed that although neurons and astrocytes were physically associated in many instances in this 2-D environment, these cells did not exhibit any preferential alignment. FIGS. 26D-26K: In contrast, co-cultures within 3-D micro-columns demonstrated that all neurons were associated with the longitudinally aligned astrocytic bundles, and predominantly extended neurites along the direction of astrocytic alignment. Scale bars FIGS. 26A-26C: 200 μm; Scale bars FIGS. 26D-26F: 100 μm: Scale bars FIGS. 26H-26K: 50 μm.

DETAILED DESCRIPTION OF THE INVENTION

The invention includes a method for producing aligned and elongated astrocyte processes from an astrocyte. The method comprises culturing an astrocyte in a culture medium: plating the cultured astrocyte onto an overlying membrane and an underlying membrane so that the cultured astrocyte adheres to both membranes; and moving the overlying membrane across the underlying membrane under an ex vivo force so that astrocyte processes from the astrocyte are stretched and aligned along the ex vivo force.

The invention further includes compositions and methods for producing three-dimensional astrocyte bundles of bi-polar and aligned astrocyte processes. The method comprises seeding a micro-column enclosing a biocompatible matrix and astrocytes; and culturing the micro-column in a culture medium. Such three dimensional astrocyte bundles are useful in a variety of applications for treatment of traumatic brain injury, spinal cord injury, stroke, and the like.

Definitions

Unless defined otherwise, all technical and scientific terms used herein have the same meaning as commonly understood by one of ordinary skill in the art to which the invention pertains. Although any methods and materials similar or equivalent to those described herein may be used in the practice for testing of the present invention, illustrative materials and methods are described herein. In describing and claiming the present invention, the following terminology will be used.

It is also to be understood that the terminology used herein is for the purpose of describing particular embodiments only, and is not intended to be limiting.

As used herein, the articles "a" and "an" are used to refer to one or to more than one (i.e., to at least one) of the grammatical object of the article. By way of example, "an element" means one element or more than one element.

As used herein when referring to a measurable value such as an amount, a temporal duration, and the like, the term "about" is meant to encompass variations of +20% or +10%, more preferably +5%, even more preferably #1%, and still more preferably +0.1% from the specified value, as such variations are appropriate to perform the disclosed methods.

As used herein, "ACLAR® film" refers to a clear, poly-chloro-trifluoroethylene (PCTFE) film, sold under the trade name ACLAR® film (a clear, poly-chloro-trifluoroethylene (PCTFE) film).

As used herein, "astrocyte living scaffold" refers to a composition comprising at least one elongated astrocyte, a biocompatible matrix, and optionally a sheath. Alternatively, "astrocyte living scaffold" may also refer to a composition comprising at least one aligned bi-polar astrocyte.

As used herein, the term "bi-polar" refers to astrocytes with two processes departing from the cell body.

As used herein, the term "aligned" refers to processes running in the same direction.

Figure 9:
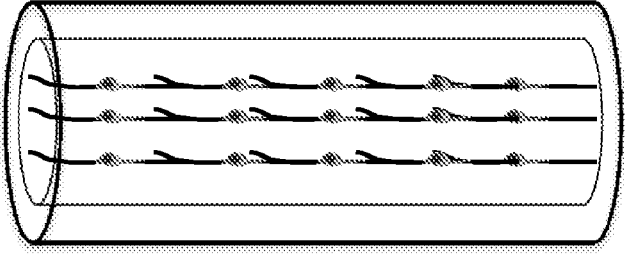
FIG. 9 is a schematic diagram illustrating the finding that astrocytes grown in transplantable hydrogel micro-columns form a bi-polar, aligned, and pro-regenerative morphology.

As used herein, the term "aligned bi-polar" refers to astrocytes with two processes running in a straight line (i.e. not departing the cell body at different angles) as shown in FIG. 9.

As used herein, the term "aligned bi-polar astrocyte" and "aligned bi-polar astrocyte processes" are used interchangeably.

As used herein, "B27® supplement (a neuronal culture supplement comprising insulin, transferrin, progesterone, putrescine, selenium, thyroid hormone T3, fatty acids, and antioxidants including vitamin E and glutathione)" refers to an optimized serum-free supplement used to support the low or high density growth and short or long-term viability of hippocampal neurons and other CNS cells.

As used herein, "biocompatible" refers to a material that is substantially non-toxic to astrocytes and that is substantially non-toxic to the cells and tissues of a recipient of the composition of the invention. A biocompatible material, when introduced into an individual, is not toxic or injurious to that individual, nor does it induce immunological rejection of the material in the mammal.

As used herein, "biocompatible matrix" refers to a material that is biocompatible and provides a permissive environment for nerve regeneration. Non-limiting examples include: hydrogel, extracellular matrix, collagen, self-assembling peptides, alginate, agarose, fibrin, cross-linked hyaluronic acid, chitosan, poly (HEMA-MMA), polylactic acid (PLA), biodegradable polyurethanes, other natural and biocompatible polymers, and combinations thereof As used herein, "biodegradable" refers to the capacity of a substance to be physically and/or chemically broken down by a living organism.

As used herein, "G-5 supplement (a chemically defined serum free supplement based on Bottenstein's G-5 formulation for growth and expression of glial cells and astrocytes)" refers to a chemically defined, serum-free supplement based on Bottenstein's G-5 supplement (a chemically defined serum free supplement based on Bottenstein's G-5 formulation for growth and expression of glial cells and astrocytes) formulation, and is used for growth and expression of glial cells (normal and tumor) of astrocytic phenotype (astrocytes).

As used herein, the term "ex vivo" refers to conditions outside the body of a living organism.

As used herein, the term "ex vivo force" and the term "external force" are used interchangeably herein. Both refer to a force caused by the changes of the conditions outside the living organism or cell(s).

As used herein, the term "living scaffolds" refers to regenerative scaffolds comprised of living neural cells in a preformed, often anisotropic, three-dimensional (3-D) architecture. Living scaffolds may facilitate targeted neural cell migration and axonal pathfinding by mimicking key developmental mechanisms. Living scaffolds commonly act based on the simultaneous presentation of structural and soluble cues.

As used herein, a "mechanically elongated astrocyte" refers to an astrocyte that has an increased length of its processes as a result of an ex vivo stretching procedure when compared with an otherwise identical astrocyte that has not been subjected to the ex vivo stretching procedure. "Mechanically elongated astrocytes" respond to the application of external "stretching" forces by stimulating growth and increasing cell/process volume by adding new intracellular constituents (e.g., plasma membrane, cytoskeleton, organelles, etc.) rather than being "thinned out".

"Mechanically elongated astrocyte", "mechanically elongated astrocyte processes", "stretch-grown astrocyte" and "stretch-grown astrocyte processes" are used interchangeably herein.

As used herein, "MATRIGEL® (a gelatinous protein mixture)" refers to a gelatinous protein mixture sold under the trade name MATRIGEL® (a gelatinous protein mixture).

As used herein, "membrane" and "matrix" are used interchangeably to refer to a material which may be used to embed or coat mechanically elongated astrocytes, or the elongated processes thereof, and which provides physical support therefor. As such, the physical form of the matrix is a highly viscous liquid, a semi-solid or a solid. While the matrix may comprise a liquid growth medium, such a liquid growth medium alone cannot serve as a matrix as used herein. The matrix enables easy handling of the elongated astrocytes, for example, for transplantation to the site of a nerve lesion, while both maintaining the integrity of the mechanically elongated astrocytes and also providing a permissive environment for subsequent nerve regeneration.

As used herein, "neurological disorder" refers to any disorder of the body's nervous system, which includes the nerves, brain and spinal cord. In certain embodiments, neurological disorders can arise from injury to the nerves, brain, or spinal cord.

As used herein, "neurodegenerative condition" refers to a condition in which there is a loss of structure or function of neurons, including death of neurons. Examples of neurodegenerative conditions include but are not limited to: Alzheimer's disease, Parkinson's disease, Huntington's disease, prion disease, motor neurone diseases, spinocerebellar ataxia, spinal muscular atrophy, amyotrophic lateral sclerosis (ALS), encephalitis, epilepsy, head and brain malformations, and hydrocephalus.

As used herein, "Neurobasal® (A neuronal culture medium for cultivating neuronal cells from hippocampus, cortex and other regions of the brain and containing no L-glutamine. L-glutamic acid, or aspartic acid)" refers to a serum-free basal medium formulated for post-natal and adult brain neuronal cells, which allows the growth of neural cells from hippocampus, cortex and other regions of the brain, wherein both long and short term maintenance of homogeneous populations of neuronal cells is achieved without the need of an astrocyte feeder layer. Neurobasal® (A neuronal culture medium for cultivating neuronal cells from hippocampus, cortex and other regions of the brain and containing no L-glutamine. L-glutamic acid, or aspartic acid) media contain no L-glutamine, L-glutamic acid, or aspartic acid.

As used herein, "stretch-grow" refers to an astrocyte process growing under ex vivo force.

A "subject" or "patient," as used therein, may be a human or non-human mammal. Non-human mammals include, for example, livestock and pets, such as ovine, bovine, porcine, canine, feline and murine mammals. Preferably, the subject is human.

As used herein, "synapse" refers to a junction between a neuron and another cell, across which chemical communication flows.

As used herein, "synapsed" refers to a neuron that has formed one or more synapses with one or more cells, such as another neuron or a muscle cell.

"Stepper motor" and "microstepper motor", used interchangeably herein, refer to a brushless, synchronous electric motor that converts digital pulses into mechanical shaft rotations with each rotation divided into a set number of steps.

As used herein, "treating a nerve lesion" means reducing the frequency and/or the severity of a symptom of the nerve lesion.

As used herein, "astrocyte bundle" refers to a three-dimensional, dense network of closely associated aligned bi-polar astrocytes in a cable-like architecture generally measuring 50-150 µm in total diameter.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Methods

The invention includes a method for producing aligned and elongated astrocyte processes from an astrocyte. The method comprises: culturing an astrocyte in a culture medium: plating the cultured astrocyte onto an overlying membrane and an underlying membrane so that the cultured astrocyte adheres to both membranes; and moving the overlying membrane across the underlying membrane under an ex vivo force. In one embodiment, the overlying membrane and the underlying membrane are planar, and the stretch-growing is conducted in a two-dimensional way. Alternatively, the overlying membrane and the underlying membrane are constructed as three-dimensional structures, and the stretch-growing is conducted in a three-dimensional way. In one embodiment, the overlying membrane and the underlying membrane can be rolled to form cylinders.

Depending on the culture and how many days the astrocyte has been stretched, the stretching rate can be varied. Rapid stretching rates cause choreographed process degeneration or outright breakage, whereas slow rates lead to adaptive motility-both extremes fail to achieve process elongation (FIG. 16A-16D).

Figures 8A, 8B, 8C, 8D:
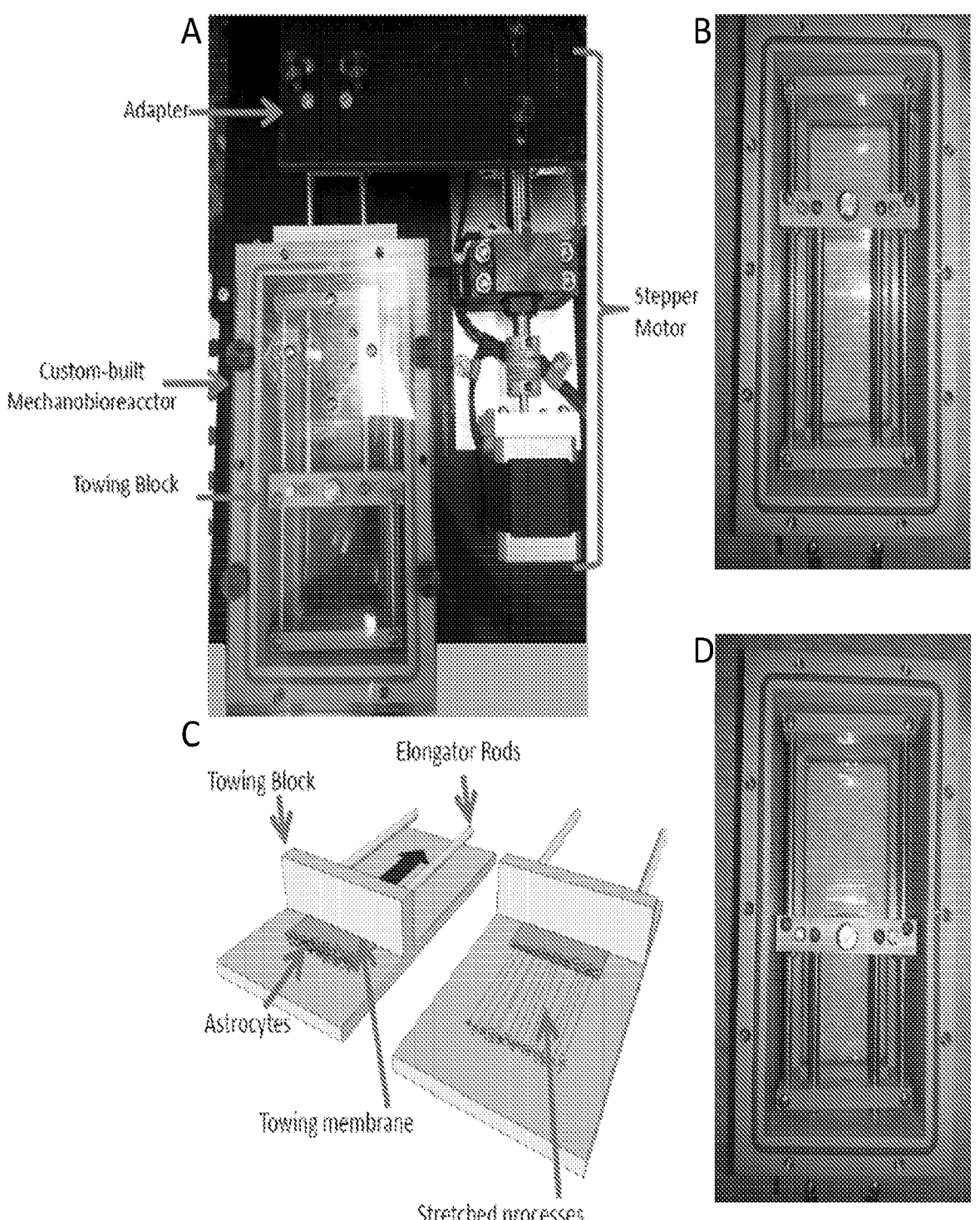
FIGS. 8A-8D, illustrates the device and scheme to stretch-grow the astrocytes.

In one embodiment, the stretching rate is in the range of about 0.1-0.5 millimeter/day. In certain instances, the rate is about 0.1 millimeter/day, about 0.15 millimeter/day, about 0.2 millimeter/day, about 0.25 millimeter/day, about 0.3 millimeter/day, about 0.35 millimeter/day, about 0.4 millimeter/day, about 0.45 millimeter/day, or about 0.5 millimeter/day. In one instance, the stretching rate is about 0.3 millimeter/day, and astrocyte processes are successfully stretch-grown (FIG. 15A-15E). In certain embodiments, the ex vivo force can be any external force that causes the elongation of astrocyte processes. Non-limiting examples of ex vivo forces are a physical force, a mechanical force, a magnetic force, or an electrical force. In one instance, the ex vivo force is a mechanical force. In some instances, the mechanical force results from a stepper motor, pulling the overlying membrane away from the underlying membrane. In this case, the overlying membrane is the towing membrane, and the underlying membrane is the stationary membrane (FIG. 8B). Alternatively, the towing membrane is the underlying membrane, while the stationary membrane is the overlying membrane.

In certain embodiments, the elongation of astrocyte processes results from a stepper motor connected to a custom mechano-bioreactor so that astrocyte processes from the astrocyte are mechanically stretched and aligned along the mechanical force, as described in FIG. 8A.

Figure 10:
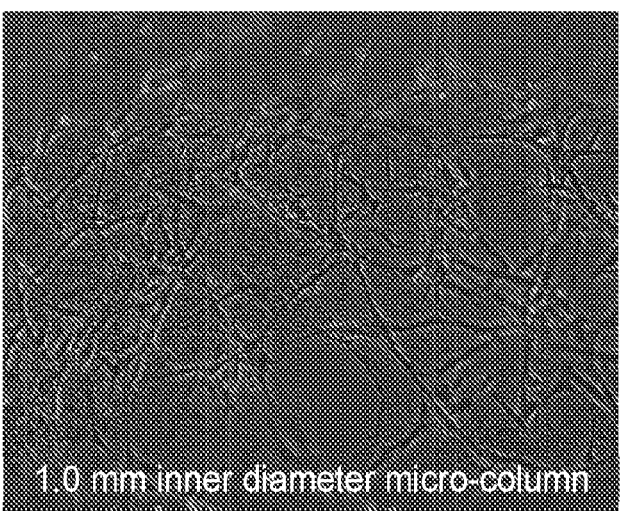
FIG. 10 is a bright field microscopy image illustrating the finding that astrocytes grown in transplantable hydrogel micro-columns with 1.0 mm inner diameter do not exhibit a preferential alignment.
Figure 12:
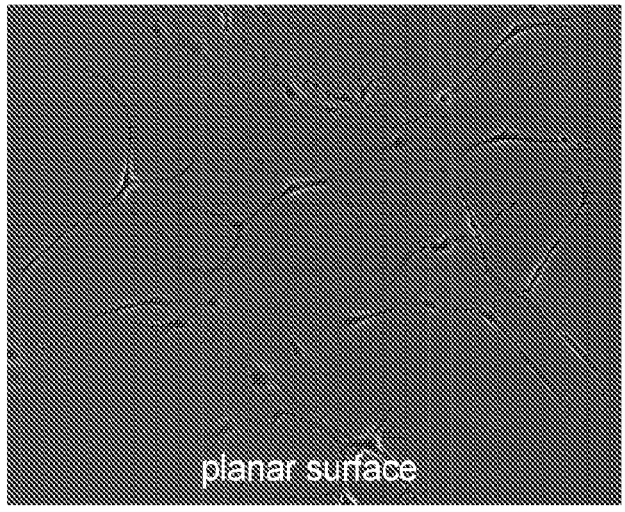
FIG. 12 is a bright field microscopy image illustrating the finding that astrocytes grown on a planar surface do not exhibit a preferential alignment.

The invention also includes a method for producing aligned bi-polar astrocyte. The method comprising seeding an astrocyte in a three-dimensional structure enclosing a biocompatible matrix; and culturing the three-dimensional structure in a culture medium. In one embodiment, the three-dimensional structure is a micro-column and the biocompatible matrix is an extracellular matrix (FIG. 9). Without being bound to a specific theory, it is theorized that the physical restrictions of the three-dimensional structure cause the astrocyte processes to grow and align in a bi-polar fashion. Astrocytes seeded on a planar surface or in a column with large inner diameter do not develop aligned bi-polar astrocyte processes (FIG. 10 and FIG. 12). In another embodiment, the astrocytes so cultured are extracted from the micro-column.

The biocompatible matrix enclosed in the three dimensional structure may provide a permissive environment for nervous system regeneration. Non-limiting examples of materials useful as a biocompatible matrix in the instant invention include: hydrogel, methylcellulose, extracellular matrix, collagen, self-assembling peptides, alginate, agarose, fibrin, cross-linked hyaluronic acid, chitosan, poly (HEMA-MMA), polylactic acid (PLA), biodegradable polyurethanes, other natural and biocompatible polymers, and combinations thereof.

In one embodiment, the three-dimensional structure is a micro-column and made of a biocompatible matrix. In one instance, the shell of the micro-column is made of a hydrogel (hydrogel micro-column). In another instance, the shell is made of an agarose hydrogel (agarose micro-column). In yet another instance, the shell is made of gelatin (gelatin micro-column). In yet another instance, the shell is made of collagen (collagen micro-column).

Figure 11:
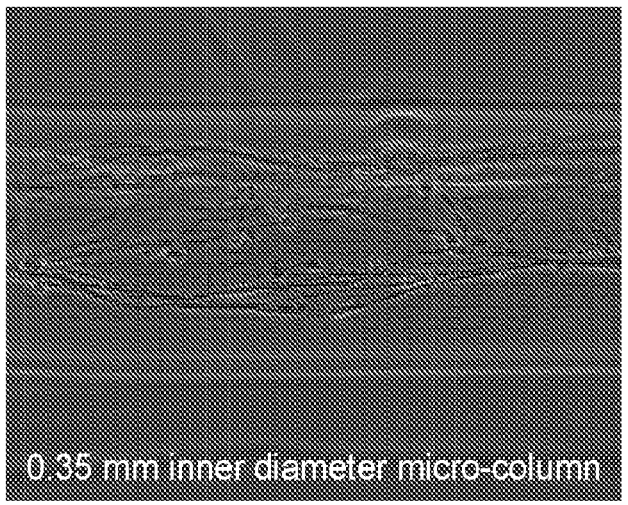
FIG. 11 is a bright field microscopy image illustrating the finding that astrocytes grown in transplantable hydrogel micro-columns with 0.35 mm inner diameter can be induced to form an aligned bi-polar morphology.
Figure 13:
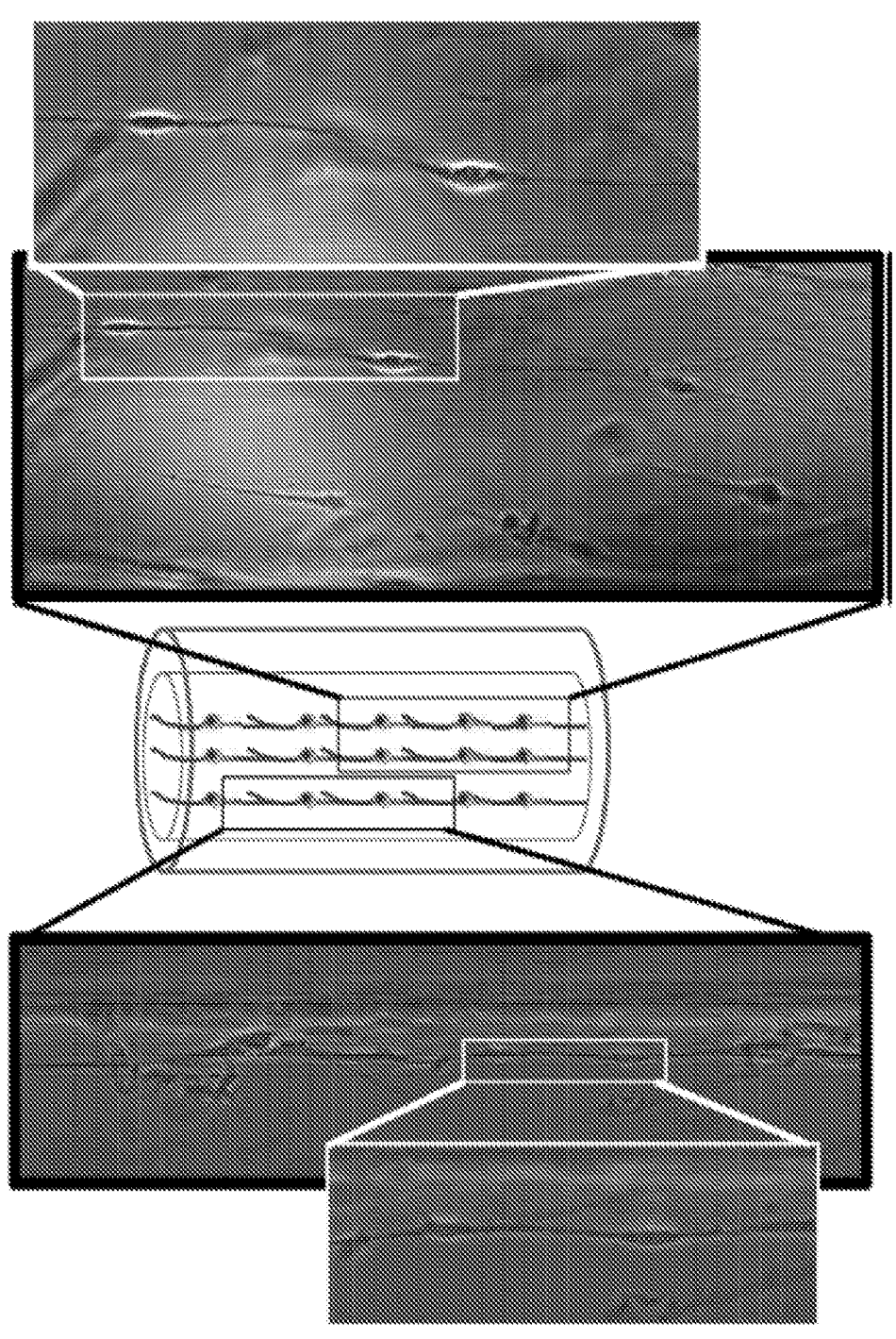
FIG. 13 is an image illustrating astrocytes grown in hydrogel columns with 0.35 mm inner diameter consistently form an aligned bi-polar morphology. Continuous chains of bi-polar astrocytes were formed across the micro-columns, nearly perfectly aligned with the long axis of the micro-column.
Figure 14:
FIG. 14 is a stained image of an aligned bi-polar astrocyte using an antibody recognizing the astrocyte-specific intermediate filament, glial fibrillary acidic protein (GFAP), with a Hoechst nuclear counterstain. This image demonstrates an aligned, bi-polar astrocyte grown in a hydrogel micro-column with a 0.35 mm inner diameter.
Figures 15A, 15B, 15C, 15D, 15E:
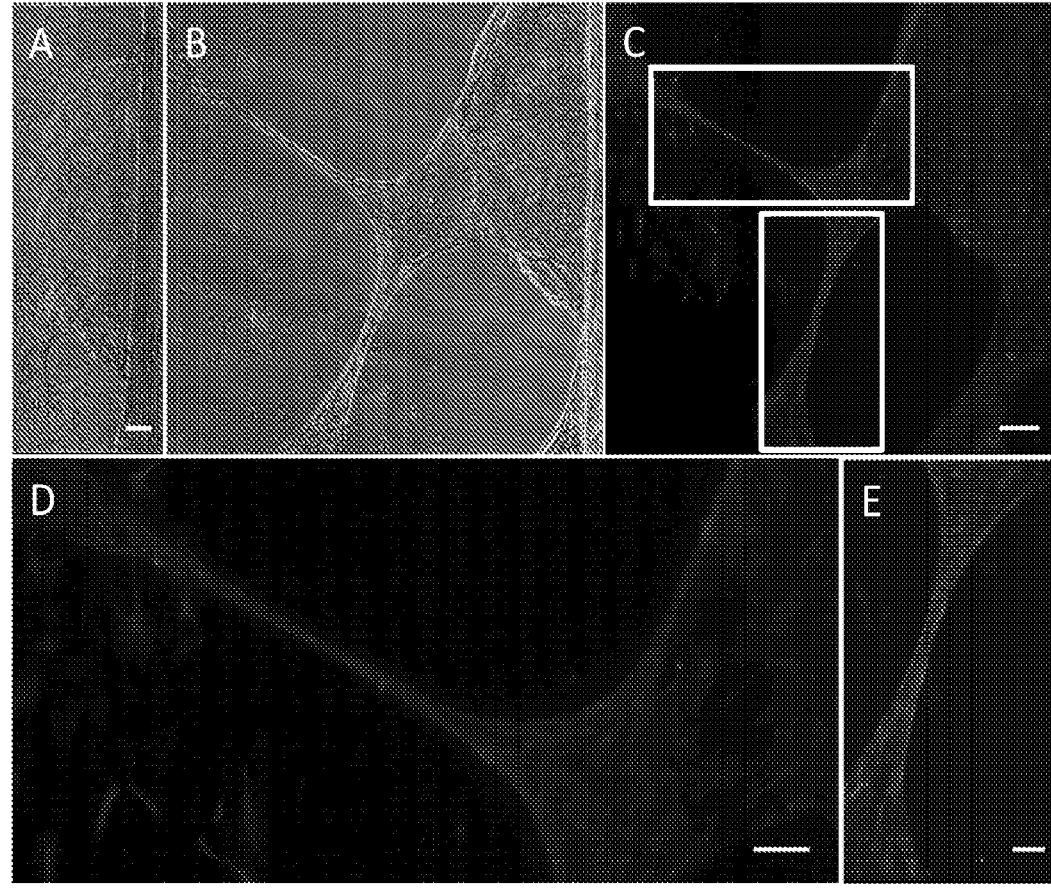
FIG. 15A is a bright field image of a culture prior to application of continuous mechanical tension for stretch-growth (scale: 50 μm).
FIG. 15B is a bright field image of a culture in the same area after several days of stretch-growth.
FIG. 15C is a fluorescent image of the same area as in FIG. 15B showing positive expression for GFAP (scale: 100 μm).
FIG. 15D is a magnified image of a stretched region from FIG. 15C (scale: 50 μm).
FIG. 15E is a magnified image of a stretched region from FIG. 15C (scale: 50 μm).
Figures 16A, 16B, 16C, 16D:
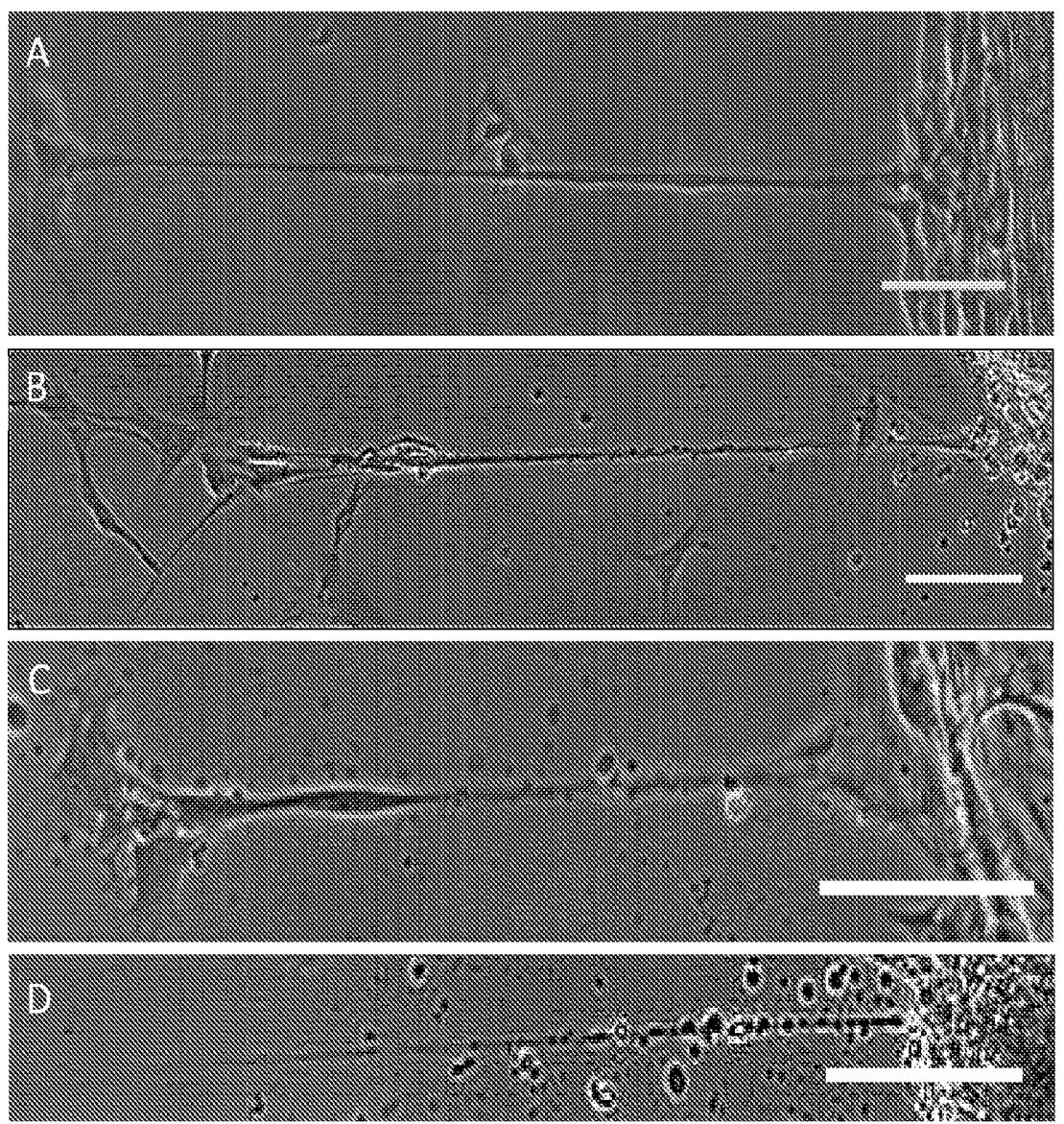
FIG. 16A is a scanning electron microscope (SEM) image illustrating the formation of healthy astrocyte processes that are smooth and continuous, and morphologically intact.
FIG. 16B is a SEM image illustrating an astrocyte process displayed early signs of degeneration, with early signs of "beading" becoming apparent along the process. Scale bar: 100 μm.
FIG. 16C is a SEM image illustrating that an astrocyte process underwent degeneration, as evidenced by the increased "beading", irregular diameter, and early disintegration of the process. Scale bar: 100 μm.
FIG. 16D is a SEM image illustrating that an astrocyte process exhibited severe "beading", discontinuity, and disintegration of the process. Scale bar: 100 μm.

In one embodiment, the micro-column used in this invention has an inner diameter in the range of about 0.1 mm to about 0.9 mm. In one instance, the inner diameter is about 0.35 mm (FIG. 11, FIG. 13, and FIG. 14). In another instance, the inner diameter is about 0.1 mm, about 0.15 mm, about 0.2 mm, about 0.25 mm, about 0.3 mm, about 0.35 mm, about 0.4 mm, about 0.45 mm, about 0.5 mm, about 0.55 mm, about 0.6 mm, about 0.65 mm, about 0.7 mm, about 0.75 mm, about 0.8 mm, about 0.85 mm, or about 0.9 mm. In another embodiment, the micro-column used in this invention has an outer diameter in the range of about 500 μm to 2000 μm. In one instance, the outer diameter is in the range of about 600 μm to 1900 μm, about 700 μm to 1800 μm, about 800 μm to 1700 μm, about 900 μm to 1600 μm, about 1000 μm to 1500 μm, about 1100 μm to 1400 μm, or about 1200 μm to 1300 μm. In another embodiment, the micro-column used in this invention has a length in the range of about 1 mm to about 20 mm. In one instance, the length is about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, or about 20 mm.

In order to generate elongated astrocyte processes according to the methods of the invention, the astrocytes are first cultured in media to generate processes.

Culture of Astrocytes

It is essential that astrocytes display robust process-bearing morphology in order to induce stretch-growth on astrocyte processes. Astrocytes are conventionally cultured in serum-containing media. That causes astrocytes to possess a "brick-like" morphology with few processes, which is not suitable for the elongation described herein. It was unexpectedly discovered that an astrocyte cultured in a new medium demonstrated a process-bearing morphology. In one embodiment, the medium comprises Neurobasal® (A neuronal culture medium for cultivating neuronal cells from hippocampus, cortex and other regions of the brain and containing no L-glutamine. L-glutamic acid, or aspartic acid) or medium comprising components similar thereto. In another embodiment, the medium comprises B27® supplement (a neuronal culture supplement comprising insulin, transferrin, progesterone, putrescine, selenium, thyroid hormone T3, fatty acids, and antioxidants including vitamin E and glutathione) or medium comprising components similar thereto. In yet another embodiment, the medium comprises G-5 supplement (a chemically defined serum free supplement based on Bottenstein's G-5 formulation for growth and expression of glial cells and astrocytes) or medium comprising components similar thereto. In yet another embodiment, the medium comprises L-glutamine. In yet another embodiment, the medium comprises Neurobasal® (A neuronal culture medium for cultivating neuronal cells from hippocampus, cortex and other regions of the brain and containing no L-glutamine. L-glutamic acid, or aspartic acid) or medium comprising components similar thereto and B27® supplement (a neuronal culture supplement comprising insulin, transferrin, progesterone, putrescine, selenium, thyroid hormone T3, fatty acids, and antioxidants including vitamin E and glutathione) or medium comprising components similar thereto. In yet another embodiment, the medium comprises Neurobasal® (A neuronal culture medium for cultivating neuronal cells from hippocampus, cortex and other regions of the brain and containing no L-glutamine. L-glutamic acid, or aspartic acid) or medium comprising components similar thereto and G-5 supplement (a chemically defined serum free supplement based on Bottenstein's G-5 formulation for growth and expression of glial cells and astrocytes) or medium comprising components similar thereto. In yet another embodiment, the medium comprises Neurobasal® (A neuronal culture medium for cultivating neuronal cells from hippocampus, cortex and other regions of the brain and containing no L-glutamine. L-glutamic acid, or aspartic acid) or medium comprising components similar thereto and L-glutamine. In yet another embodiment, the medium comprises Neurobasal® (A neuronal culture medium for cultivating neuronal cells from hippocampus, cortex and other regions of the brain and containing no L-glutamine. L-glutamic acid, or aspartic acid) or medium comprising components similar thereto, B27® supplement (a neuronal culture supplement comprising insulin, transferrin, progesterone, putrescine, selenium, thyroid hormone T3, fatty acids, and antioxidants including vitamin E and glutathione) or medium comprising components similar thereto and G-5 supplement (a chemically defined serum free supplement based on Bottenstein's G-5 formulation for growth and expression of glial cells and astrocytes) or medium comprising components similar thereto. In yet another embodiment, the medium comprises Neurobasal® (A neuronal culture medium for cultivating neuronal cells from hippocampus, cortex and other regions of the brain and containing no L-glutamine. L-glutamic acid, or aspartic acid) or medium comprising components similar thereto, B27® supplement (a neuronal culture supplement comprising insulin, transferrin, progesterone, putrescine, selenium, thyroid hormone T3, fatty acids, and antioxidants including vitamin E and glutathione) or medium comprising components similar thereto and L-glutamine. In yet another embodiment, the medium comprises B27® supplement (a neuronal culture supplement comprising insulin, transferrin, progesterone, putrescine, selenium, thyroid hormone T3, fatty acids, and antioxidants including vitamin E and glutathione) or medium comprising components similar thereto, G-5 supplement (a chemically defined serum free supplement based on Bottenstein's G-5 formulation for growth and expression of glial cells and astrocytes) or medium comprising components similar thereto, and L-glutamine.

In one embodiment, the medium comprises Neurobasal® (A neuronal culture medium for cultivating neuronal cells from hippocampus, cortex and other regions of the brain and containing no L-glutamine. L-glutamic acid, or aspartic acid) or medium comprising components similar thereto, B27® supplement (a neuronal culture supplement comprising insulin, transferrin, progesterone, putrescine, selenium, thyroid hormone T3, fatty acids, and antioxidants including vitamin E and glutathione) or medium comprising components similar thereto, G-5 supplement (a chemically defined serum free supplement based on Bottenstein's G-5 formulation for growth and expression of glial cells and astrocytes) or medium comprising components similar thereto, and L-glutamine. In certain embodiments, the amount of B27® supplement (a neuronal culture supplement comprising insulin, transferrin, progesterone, putrescine, selenium, thyroid hormone T3, fatty acids, and antioxidants including vitamin E and glutathione) varies from about 1% to 5% by volume. In other embodiments, the amount of G-5 supplement (a chemically defined serum free supplement based on Bottenstein's G-5 formulation for growth and expression of glial cells and astrocytes) varies from about 0.1% to 3% by volume. In other embodiments, the amount of L-glutamine varies from about 0.1% to 1.0% by volume. In other embodiments, the culture comprises Neurobasal® (A neuronal culture medium for cultivating neuronal cells from hippocampus, cortex and other regions of the brain and containing no L-glutamine. L-glutamic acid, or aspartic acid), 2% B27® supplement (a neuronal culture supplement comprising insulin, transferrin, progesterone, putrescine, selenium, thyroid hormone T3, fatty acids, and antioxidants including vitamin E and glutathione) by volume, 1% G-5 supplement (a chemically defined serum free supplement based on Bottenstein's G-5 formulation for growth and expression of glial cells and astrocytes) by volume, and 0.25% L-Glutamine by volume. In these embodiments above, neurobasal is the base media.

Once a suitable culture media to support the process-bearing morphology is developed, a matrix inducing the formation of networks between neighboring astrocyte processes is identified. This formation of networks between adjacent astrocytes is important for stretch-growth, allowing for the processes to span the interface between the overlying membrane and underlying membrane. This matrix can be used as either the underlying membrane or the overlying membrane or both.

Figures 4A, 4B:
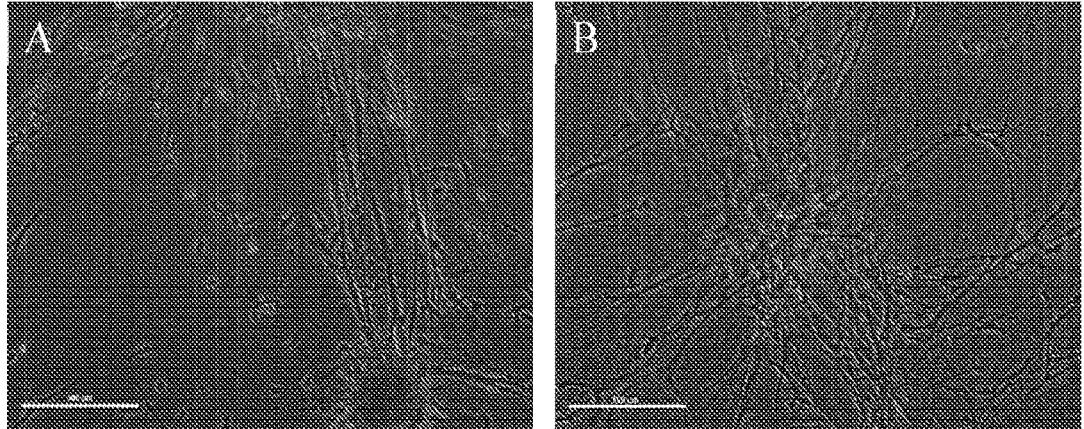
FIGS. 4A-4B, is a panel of images showing that the process-bearing morphology is maintained out to 20 days in vitro.

A non-limiting example of such matrix is collagen type I coated matrix. In addition to the process-bearing morphology, collagen type I coated matrix also induces the formation of networks between neighboring astrocyte processes. Furthermore, not only was it found that collagen type I coated membrane showed robust process outgrowth and network formation, but also collagen type I coated membrane allowed the process-bearing morphology to endure out to 20 days in vitro (FIG. 4). In certain embodiments, the ability of astrocytes to maintain this process-bearing morphology long term is important because the stretch-growth process may last for days or weeks in culture, depending on the target process length and rate of stretch.

Overlying and Underlying Membranes

The composition of the overlying membrane and the underlying membranes useful to stretch grow astrocytes can be independently a biocompatible matrix, a synthetic polymer or any combinations thereof. Non-limiting examples of the overlying membrane or the underlying membrane include polystyrene, ACLAR® film (a clear, poly-chloro-trifluoroethylene (PCTFE) film), collagen coated ACLAR® film (a clear, poly-chloro-trifluoroethylene (PCTFE) film), and MATRIGEL® (a gelatinous protein mixture) coated ACLAR® film (a clear, poly-chloro-trifluoroethylene (PCTFE) film).

In certain embodiments, the underlying membrane comprises polystyrene. In other embodiments, the underlying membrane comprises thick ACLAR® 33C film (a clear, poly-chloro-trifluoroethylene (PCTFE) film). In yet other embodiments, the underlying membrane comprises 1 mg/mL MATRIGEL® (a gelatinous protein mixture) on thick ACLAR® 33C film (a clear, poly-chloro-trifluoroethylene (PCTFE) film) (199 µm). In yet other embodiments, the overlying membrane comprises 1 mg/mL rat-tail collagen type I coated on ACLAR® 33C film (a clear, poly-chloro-trifluoroethylene (PCTFE) film) film (19 µm), and the underlying membrane comprises collagen type I coated on thick ACLAR® 33C film (a clear, poly-chloro-trifluoroethylene (PCTFE) film) (199 µm), as illustrated in FIG. 8.

In the process of elongation, one of the two membranes—the overlying membrane and the underlying membrane—is the towing membrane, and the other is the stationary membrane.

It is understood that a biocompatible matrix can be used as the overlying or underlying membrane in the stretch growth astrocyte. In one instance, the biocompatible matrix is flexible to permit to flex or bend as necessary. In another instance, the biocompatible matrix may provide a permissive environment for nerve regeneration. Non-limiting examples of materials useful as a biocompatible matrix in the instant invention include: hydrogel, methylcellulose, extracellular matrix, collagen, self-assembling peptides (e.g., U.S. Patent Application Publication No. 2004/50287186), alginate, agarose, fibrin, cross-linked hyaluronic acid, chitosan, poly (HEMA-MMA), polylactic acid (PLA), biodegradable polyurethanes, other natural and biocompatible polymers, and combinations thereof.

In certain embodiments, the biocompatible matrix is biodegradable. In other embodiments, the biocompatible matrix is a hydrogel. In yet other embodiments, the biocompatible matrix is a hydrogel comprising collagen. In yet other embodiments, the biocompatible matrix is a hydrogel comprising agarose. In yet other embodiments, the biocompatible matrix comprises collagen and agarose. In yet other embodiments, the biocompatible matrix comprises biodegradable polyurethanes. In yet other embodiments, the biocompatible matrix comprises cross-linked hyaluronic acid. In yet other embodiments, the biocompatible matrix comprises methylcellulose. In yet other embodiments, the biocompatible matrix comprises agarose and methylcellulose.

The biocompatible matrix, optionally, comprises one or more compounds that contribute directly or indirectly to the regeneration of neural tissue. Such compounds include, but are not limited to, neurotrophic factors, surface receptors, nutrients, and compounds that counteract compounds that inhibit growth and regeneration of neural tissue. Such compounds may be proteins, peptides, cell adhesion molecules, lipids, nucleic acids, e.g., RNA, siRNA or DNA, small molecules, and carbohydrates. Optionally, the compound is covalently attached to the biocompatible matrix.

Non-limiting examples of neurotrophic factors useful in the instant invention include: nerve growth factor (NGF), brain derived neurotrophic factor (BDNF), neurotrophin 3 (NT-3), neurotrophin 4/5 (NT-4/5), neurotrophin 6 (NT-6), neurotrophin 7 (NT-7), ciliary neurotrophic factor (CNTF), neurturin (NTN), persephin, artemin, basic fibroblastic growth factor (bFGF), glial-cell-derived neurotrophic factor (GDNF), purpurin and synthetic neurotrophins, such as pan-neurotrophin-1 (PNT-1).

Non-limiting examples of cell adhesion molecules (CAMs) useful in the instant invention include: L1, NCAM, neurofascin, and contactin.

The matrix may also include a compound that counteracts the inhibitors of growth and regeneration of neural tissue. Such compounds include, but are not limited to, antibodies directed against compounds such as myelin-associated glycoprotein and oligodendrite myelin glycoprotein.

Astrocyte stretch-growth relies on the extension of processes across the interface of adjacent membranes. Therefore, prior to elongating astrocyte processes via stretch-growth, the ability of astrocytes to bridge the interface of a overlying membrane and underlying ACLAR® film (a clear, poly-chloro-trifluoroethylene (PCTFE) film) membrane is assessed (illustrated in FIG. 5). In certain embodiments, plating astrocytes across the thinner collagen type I coated ACLAR® 33C film (a clear, poly-chloro-trifluoroethylene (PCTFE) film) (19 μm) overlying membrane interface produced more robust networks when compared to the thicker collagen type ACLAR® 22A film (a clear, poly-chloro-trifluoroethylene (PCTFE) film) overlying membrane interface.

Figures 5A, 5B, 5C, 5D:
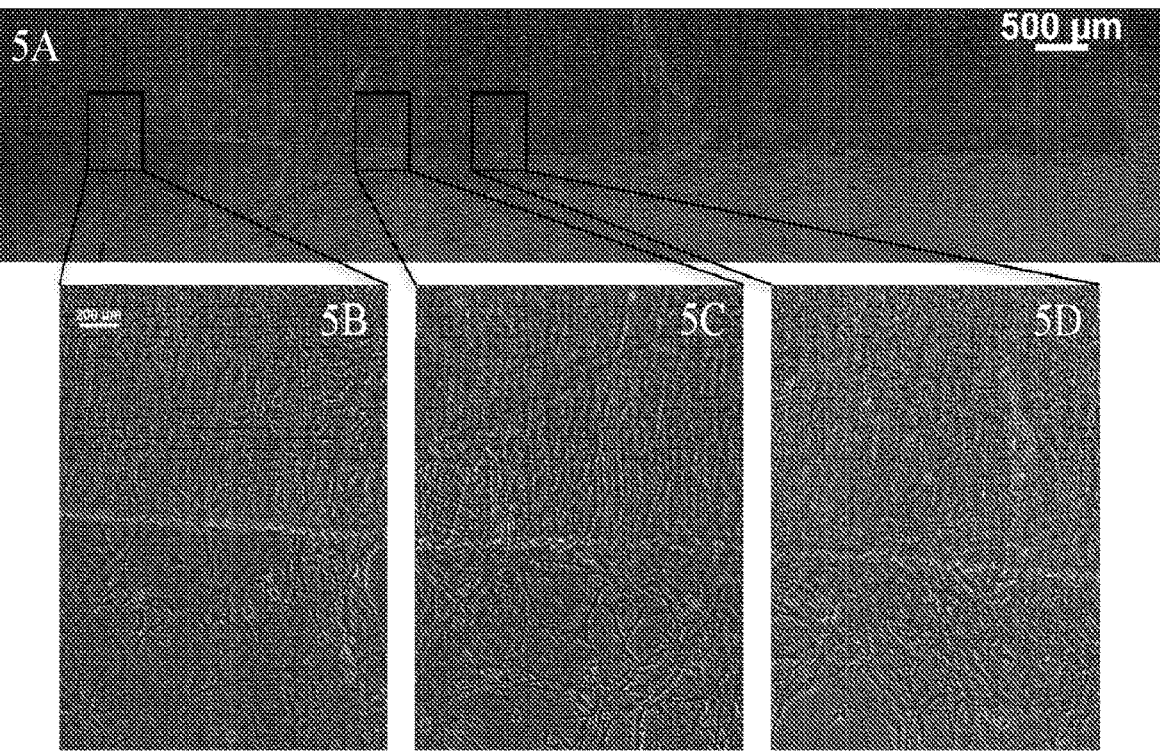
FIGS. 5A-5D, is a panel of images showing that astrocytes plated across a copolymer film, ACLAR® 33C film (a clear, poly-chloro-trifluoroethylene (PCTFE) film, overlying membrane results in robust astrocytic network formation across the interface.
Figures 6, 7:
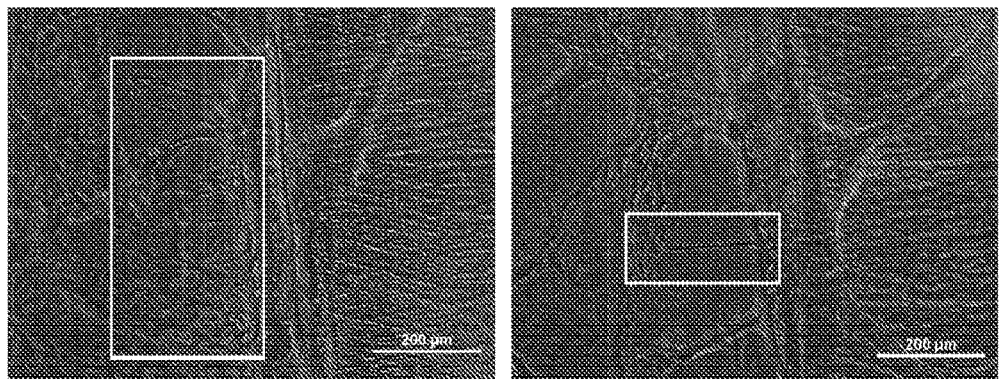
FIG. 6 illustrates the finding that constant mechanical tension induced stretch-growth and organized orientation of the astrocyte processes. After growing in culture for 5 days in vitro, astrocytes were mechanically stretch-grown at a rate of 0.5 mm/day for 3 days, producing astrocyte process alignment orthogonal to the overlying membrane and parallel to the direction of the applied tension (outlined with a white box).
FIG. 7 is a set of images illustrating the finding that constant mechanical tension caused astrocyte processes to grow up to several millimeters in length. After allowing astrocytes to form networks across a collagen type I coated membrane interface for 3 days, the networks were mechanically grown at a rate of 0.5 mm/day for 5 days.

Using the technology disclosed herein, it was unexpectedly discovered that astrocyte processes can undergo stretch-growth when applied with constant mechanical tension. Rather than tearing in response to the mechanical tension, the astrocytes acclimated by lengthening (and presumably adding new biological material) with the applied force. Prior to stretch, the astrocytes bridged the interface with no specific orientation (as depicted in FIG. 5). However, after stretching the astrocytes at a rate of 0.5 mm/day for 3 days, the processes showed growth of up to 200 μm and assumed highly organized, parallel orientations (FIG. 6).

Under optimized plating techniques, extreme stretch-growth in astrocyte processes were obtained. Stretching at a rate of 0.5 mm/day for 5 days, astrocyte processes were shown to be able to stretch up to a length of 2.5 mm in response to the constant applied mechanical tension, (FIG. 7).

Stretch-Growth Device

A custom built mechano-bioreactor is used to generate the elongated astrocytes with long processes. An example of such a device is disclosed in U.S. Pat. Nos. 6,264,944 and 6,365,153, herein incorporated by reference in its entirety.

As illustrated herein, a mechano-bioreactor comprises an enclosed cell culture system, a motor-table assembly, mirostepper motors, a linear table, an encoder, and an indexer/driver. The enclosed culture system comprises a plexiglass box with a removable lid and glass bottom and a gas exchange port. On the inside base, a long rectangular absorbable membrane (substrate: Lactosorb, BioMet, Inc., Warsaw Ind.) for astrocyte attachment was fixed in place. Biologically absorbable material was selected because it was compatible for transplantation into tissue. Another shorter membrane is placed on top, leaving an exposed region of the underlying membrane near one end. This towing membrane was fixed to a movable bar that was driven by two steel rods. Movement of the towing membrane across the underlying membrane is effected by activation of a motor-table assembly (Servo Systems, Inc., Montville, N.J.) and microstepper motors (Pacific Scientific, Rockford, Ill.). Control of the movements is computer driven using a linear table (Aerotech, Irvine, Calif.), an encoder (Remco Encoders, Inc., Goleta, Calif.) and an indexer/driver (Panther, Intelligent Motor Systems, Marlborough, Conn.: Quickstep II Driver Software).

Although, as described in the stretch-growth device, the towing membrane is the overlying membrane and the stationary membrane is the underlying membrane described herein, one skilled in art understands that the towing membrane can be the underlying membrane and the stationary membrane can be the overlying membrane to achieve same results.

Astrocyte Bundle Formation

Figures 17A, 17B, 17C:
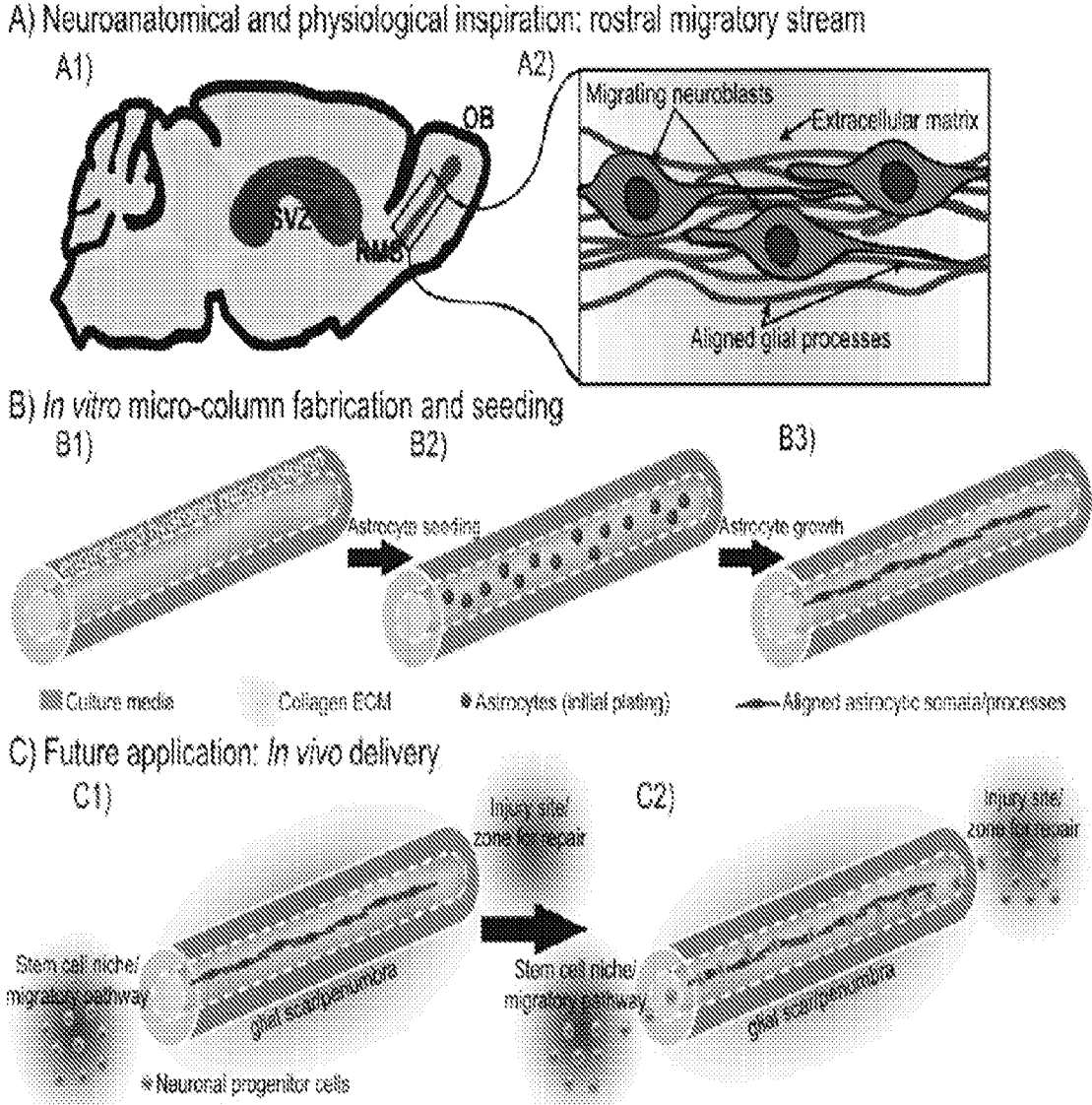
FIGS. 17A-17C are a series of schematic representations of aligned astrocyte constructs designed to promote central nervous system regeneration. A "living scaffold" was constructed composed of aligned astrocytes that mimic developmental processes to ultimately facilitate central nervous system repair.

According the the methods disclosed herein, micro-columns have been designed and fabricated to induce alignment of astrocytes within the central channel of the cylindrical, pipe-like constructs as shown in FIG. 17B. As illustrated herein, a micro-column comprises a three-dimensional cylindrical structure enclosing a biocompatible matrix. In one embodiment, the biocompatible matrix is an agarose hydrogel. In another embodiment, the micro-column contains a bioactive collagenous extracellular matrix on the interior surface of the cylinder that promotes astrocyte adherence and survival. In one embodiment, the inner diameter of the micro-column ranges from 0.1 mm to 3 mm. In certain embodiments, the inner diameter is 0.15 mm and the the outer diameter is 2 mm. In certain other embodiments, the inner diameter ranges from about 0.1 to 0.4 mm and the outer diameter ranges from about 2 to 3 mm. In another embodiment, the inner diameter of the micro-column is about 0.18 mm and the outer diameter is about 0.789 to 2 mm. In other embodiments, the inner diameter is from about 0.3 mm to 0.35 mm and the outer diameter is from about 0.789 mm to 2 mm.

In one embodiment, the micro-columns are made by dissolving agarose in a saline solution, inserting a needle into the center of a glass capillary tube and drawing the solution into the tube via capillary action. After the agarose cools and solidifies, the needle is removed producing a hollow cylindrical structure. The micro-column is then pushed out of the capillary tube and sterilized. Next, a collagen extracellular matrix solution is microinjected into each end of the micro-column which coats the interior surface. This matrix is allowed to polymerize. In order to produce three-dimensional astrocyte bundles, astrocytes are microinjected into the micro-columns at a high cell density. After the cells adhere to the micro-column, the cells are cultured in a defined serum-free media in order to induce the mature, process-bearing astrocyte morphology. Optimizing the inner diameter of the micro-column ensures astrocyte processes align with the longitudinal axis of the micro-column, dictating directionality of astrocyte outgrowth. Seeding the astrocytes into the micro-column at high density produces a tight "bundling" effect of the longitudingally aligned astrocyte somata and processes. This process generates astrocyte bundles: a dense network of closely associated astrocytes in a cable-like architecture generally measuring about 50-150 microns in total diameter. In one embodiment, the astrocytes so cultured are extracted from the micro-column.

Compositions

In one aspect, the present invention also includes a composition comprising an astrocyte comprising aligned and elongated astrocyte processes made by the methods described herein.

In certain embodiments, an ex vivo force used to stretch-grow astrocyte processes can be any external force that causes the elongation of astrocyte processes. Non-limiting examples of ex vivo forces are a physical force, a mechanical force, a magnetic force, or an electrical force. In one instance, the ex vivo force is a mechanical force. In some instances, the mechanical force results from a stepper motor. In certain embodiments, the elongation of astrocyte processes results from a stepper motor connected to a custom mechano-bioreactor (FIG. 8A).

In another aspect, the invention includes a composition comprising an astrocyte living scaffold comprising at least an aligned and elongated astrocyte. In one embodiment, the living scaffold further comprises a biocompatible matrix. In addition to elongated astrocytes and a biocompatible matrix, the astrocyte living scaffold may further comprise a biocompatible sheath. The sheath provides additional physical support to the astrocyte living scaffold. The sheath also provides a means of securing the position of an astrocyte living scaffold at the site of a nerve lesion. The sheath partially or wholly enfolds or surrounds at least part of the astrocyte living scaffold. For instance, in certain embodiments, the sheath comprises a sheet of bio-resorbable material which forms a cylinder around substantially all of the elongated astrocytes tracts that are coated or embedded in the biocompatible matrix. In other embodiments, the sheath forms a cylinder around substantially the entire length of the elongated astrocytes. In yet other embodiments, the sheath is a partial cylinder, i.e., the sheath does not form a complete circle, and it enfolds substantially the entire length of the elongated astrocytes. In yet other embodiments, the sheath is flexible and can be sutured. Optionally, the sheath is bio-resorbable and/or biodegradable. Non-limiting examples of materials useful as a sheath include: surgical meshes, collagen-based sheets, nylon membranes and expanded PTFE membranes. In certain embodiments, the composition further comprises a biocompatible matrix to support the elongate astrocyte in the process of implantation to the injury site. In one embodiment, the matrix is biodegradable.

In yet another aspect, the invention includes a composition comprising at least one aligned bi-polar astrocyte. In one instance, the composition comprises a three-dimensional structure enclosing a biocompatible matrix and at least one aligned bi-polar astrocyte. In another instance, the composition comprises a micro-column enclosing a biocompatible matrix and at least one aligned bi-polar elongated astrocyte. In another aspect, the composition comprises a micro-column enclosing a biocompatible matrix and a bundle of aligned, bi-polar astrocyte processes.

Methods of Treatment

Neural tissue engineering offers tremendous promise to address the effects of neurodegenerative disease or injury in the nervous system. Successful application may involve the integration of engineered living tissue to directly restore lost function or to augment the capacity for nervous system regeneration. The present invention may be used for a range of in vitro test bed and neural tissue engineering applications. The tissue engineered astrocyte living scaffold described herein that comprises aligned and elongated astrocyte processes or aligned bi-polar astrocyte processes can be implanted by neurosurgeons to facilitate repair and functional restoration following trauma or degenerative disease in the nervous system, for instance traumatic brain injury, spinal cord injury, stroke, Alzheimer's disease, or Parkinson's disease, among other disorders.

It is well understood in the art that tissue engineered constructs for neurosurgical implantation can 1) direct and drive axonal regeneration and targeted pathfinding across long lesions in the brain or spinal cord: 2) provide "regenerative pathways" from a stem cell niche in the brain or spinal cord to repopulate regions experiencing neuronal loss (either diffuse loss or profound loss associated with stroke, tumor excision, epileptic resection, contusion, and others). Here, constructs can direct and drive migration of cells to reform complex neural tissue (e.g. stem cells and/or partially or fully differentiated cells) in the brain or spinal cord: 3) by mimicking the migratory pathway of radial glia, these "stretch grown" astrocyte processes can orchestrate the reformation of complex neural tissue architecture (e.g., stem cells and/or partially or fully differentiated cells) in the brain or spinal cord: 4) these may provide pathways to "punch through" the glial scar to allow for stem cell, neuronal, or glial migration, or axonal pathfinding: 5) these may serve as an in vitro test bed to study developmental mechanisms, regenerative mechanisms, or glial disease states.

Accordingly, the present invention provides a method for treating nervous system injury or degeneration in a mammal. In one instance, the method comprises transplanting into the nervous system injury or degeneration site an astrocyte living scaffold comprising a biocompatible matrix and a composition comprising an astrocyte comprising aligned and elongated astrocyte processes. The aligned and elongated astrocyte processes result from ex vivo machine-driven, physical stretching of astrocytes maintained in culture. In another instance, the method comprises transplanting into the nervous system injury or degeneration site a three-dimensional structure enclosing a biocompatible matrix and at least an aligned bi-polar astrocyte. In one example, the three-dimensional structure is a micro-column and the biocompatible matrix is an agarose hydrogel. In another instance, the method comprises transplanting into the nervous system injury or degeneration site a three-dimensional structure enclosing a biocompatible matrix and a bundle of aligned bi-polar astrocytes. In one example, the three-dimensional structure is a micro-column and the biocompatible matrix is an agarose hydrogel.

In certain embodiments, the present invention provides a method treating nervous system injury or degeneration in a mammal. In one instance, the method comprises transplanting into the nervous system injury or degeneration site a composition comprising an astrocyte comprising aligned and elongated astrocyte processes. In one instance, the aligned and elongated astrocyte processes result from ex vivo machine-driven, physical stretching of astrocytes maintained in culture. In another instance, the method comprises transplanting into the nerve injury site a three-dimensional structure enclosing a biocompatible matrix and at least an aligned bi-polar astrocyte. In one example, the three dimensional structure is a micro-column and the biocompatible matrix is an agarose hydrogel. In another embodiment, the method comprises transplanting into the nerve injury site a three-dimensional structure enclosing a biocompatible matrix and a bundle of aligned bi-polar astrocytes. In one example, the three dimensional structure is a micro-column and the biocompatible matrix is an agarose hydrogel.

In one embodiment, the present invention provides a method for treating spinal cord injury in a mammal. In one instance, the method comprises transplanting into the spinal cord injury site a composition comprising an astrocyte comprising aligned and elongated astrocyte processes. The aligned and elongated astrocyte processes result from ex vivo machine-driven, physical stretching of astrocytes maintained in culture. In another instance, the method comprises transplanting into the nerve injury site a three-dimensional structure enclosing a biocompatible matrix and at least an aligned bi-polar astrocyte. In one example, the three-dimensional structure is a micro-column and the biocompatible matrix is an agarose hydrogel.

In one embodiment, the present invention provides a method for treating brain injury in a mammal. In one instance, the method comprises transplanting into the brain injury site a composition comprising an astrocyte comprising aligned and elongated astrocyte processes. The aligned and elongated astrocyte processes result from ex vivo machine-driven, physical stretching of astrocytes maintained in culture. In another instance, the method comprises transplanting into the nerve injury site a three-dimensional structure enclosing a biocompatible matrix and at least an aligned bi-polar astrocyte. In one example, the three-dimensional structure is a micro-column and the biocompatible matrix is an agarose hydrogel. In another instance, the method comprises transplanting into the nerve injury site a three-dimensional structure enclosing a biocompatible matrix and a bundle of aligned bi-polar astrocytes. In one example, the three-dimensional structure is a micro-column and the biocompatible matrix is an agarose hydrogel.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Primary Cortical Astrocyte Harvest and Culture

Astrocytes were harvested from postnatal day 0 or day 1 (P0-P1) Sprague Dawley rat pups. Briefly, cerebral cortices were extracted and dissociated with 0.25% trypsin+EDTA followed by 0.15 to 0.30 mg/mL DNase diluted in HBSS and triturated to separate the tissue. The suspension was then centrifuged at 1000 RPM for 3 min, and cultured in DMEM F-12 media supplemented with 10% fetal bovine serum (FBS), as previously described (Cullen, et al., J. Neurotrauma., 2006, 23:1304-1319). Cultures were maintained by changing media after 24 hours and every 2 days thereafter. The astrocytes were then passaged and cultured in a serum free environment to induce an immature "radial" glia phenotype. This defined medium consisted of Neurobasal® (A neuronal culture medium for cultivating neuronal cells from hippocampus, cortex and other regions of the brain and containing no L-glutamine. L-glutamic acid, or aspartic acid) media supplemented with 0.25% L-glutamine, 2% B27® supplement (a neuronal culture supplement comprising insulin, transferrin, progesterone, putrescine, selenium, thyroid hormone T3, fatty acids, and antioxidants including vitamin E and glutathione) and 1% G-5 supplement (a chemically defined serum free supplement based on Bottenstein's G-5 formulation for growth and expression of glial cells and astrocytes) at a density of 40,000 to 125,000 cells/cm².

Cortical Astrocyte Culture Using Custom-Built Mechano-bioreactors

Astrocytes were plated in custom-built mechano-bioreactors previously used for axon stretch growth, as shown in FIG. 8A. The mechano-bioreactor consists of a towing block attached to rods that are then connected to a motorized stepper that gradually pulls the towing block backward, as described in FIGS. 8B-8D. Cells are plated (at a density of 40,000 to 125,000 cells/cm²) along the interface of two membranes: a thicker 199 µm transparent ACLAR® 33C film (a clear, poly-chloro-trifluoroethylene (PCTFE) film) base membrane and a ultra-thin 19 µm transparent ACLAR® 33C film (a clear, poly-chloro-trifluoroethylene (PCTFE) film) membrane that is sanded to further reduce thickness, and connected to the towing block. This ultra-thin membrane is referred to as the towing membrane. The base membrane and towing membrane were etched with 1N NaOH, and attached to the towing block of the mechano-bioreactor. The plating area was then coated with 0.05 mg/mL poly-L-lysine (PLL) followed by 1 mg/mol rat tail collagen type I at 37° C. and allowed to incubate overnight until dry. The cells were passaged as described previously, plated, and allowed to adhere for 45 min before flooding the mechano-bioreactor with defined media. Approximately 4-5 days after plating, the mechano-bioreactors were connected to the stepper motor and a LabView program was used to apply mechanical stretch on the cells by gradually pulling the towing membrane back at a rate of 0.1-0.5 mm per day.

Hydrogel Micro-Column Fabrication. Coating, and Astrocyte Seeding

Micro-columns consisted of a thin molded cylinder of agarose with an extracellular matrix (ECM) on the interior to allow for astrocyte adhesion and growth. The outer hydrogel structure consisted of 3% agarose in Dulbecco's Phosphate-Buffered Saline (DPBS). The agarose shell was molded with an outer diameter ranging from 798 µm to 2000 µm. To start the fabrication process, the heated agarose solution was drawn into a microliter glass capillary tube (Drummond Scientific, Broomall, PA). A needle (diameter: 180 µm-1000 µm) (Seirin, Weymouth, MA) was in the center of the liquid agarose-filled capillary tube to produce the hollow core. Once the capillary tube had cooled to room temperature, the needle was slowly retracted, and the micro-column was gently ejected from the capillary tube. Micro-columns were then cut to 5 mm in length, and 3 µL of a collagen ECM solution (rat tail type I collagen, 1.0 mg/ml) was microinjected into each end. Thusly, the micro-columns featured a cylindrical agarose shell with a collagen ECM along the interior. The micro-columns were then incubated at 37° C. for 30 minutes, and the micro-columns were placed in DPBS and sterilized by UV light for 15 minutes. To seed micro-columns with astrocytes, 5 L of the cell culture solution (2-4×10⁵ cells/mL) was delivered to each end of the micro-columns via a micropipette (10 µL delivered in total). Seeded micro-columns were placed in a humidified tissue culture incubator (37° C. and 5% $CO_2$) for 40 minutes to allow cells to adhere. Then pre-warmed media was added slowly to the culture dish. Every 2-3 days in vitro, half media changes were performed with pre-warmed media.

Figures 18A, 18B, 18C, 18D, 18E, 18F:
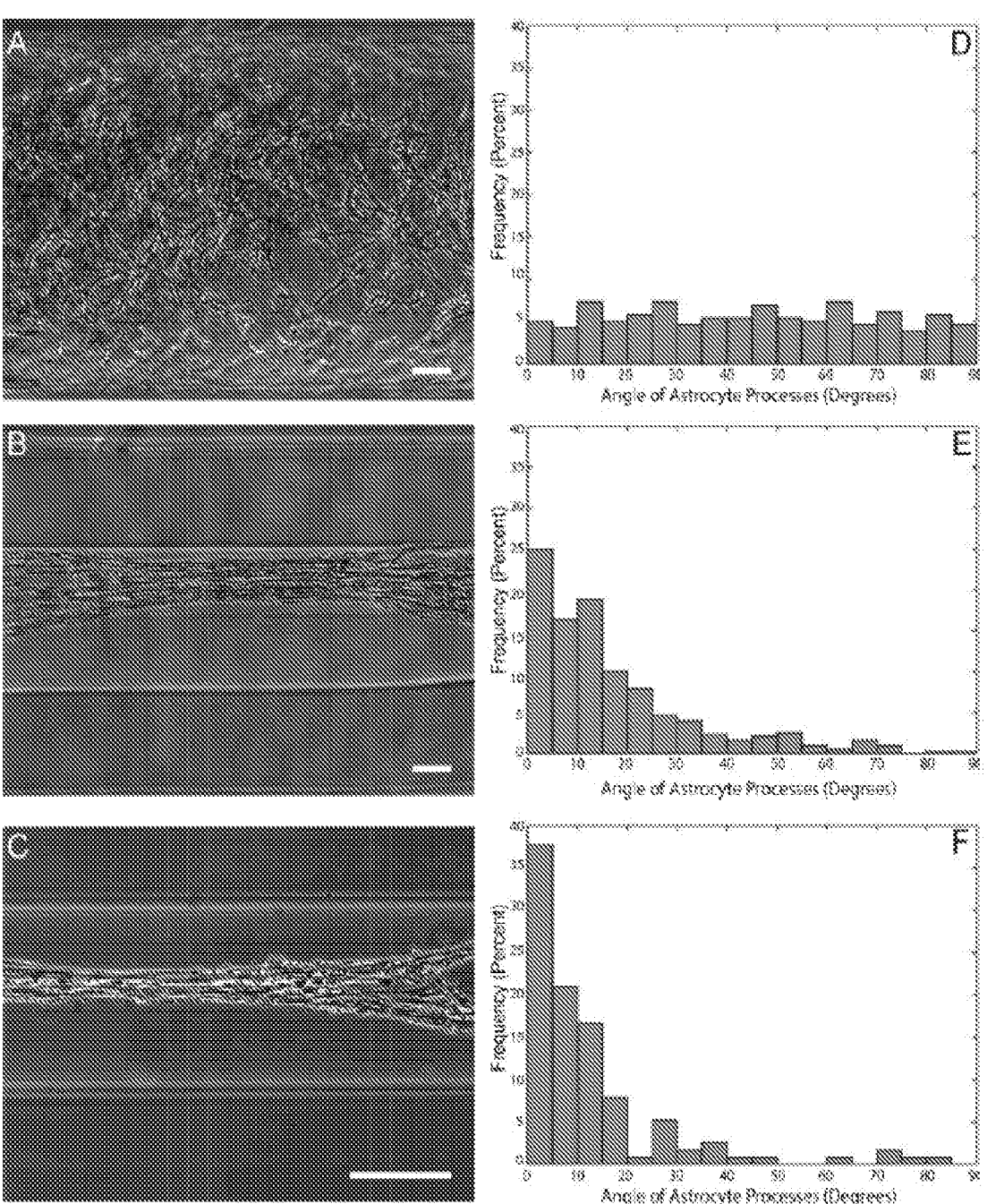
FIGS. 18A-18F are a series of images and graphs that illustrate that decreasing the micro-column inner diameter increased the extent of astrocyte alignment. Astrocytes grown in hydrogel micro-columns were found to increase alignment as a function of decreasing inner diameter (ID). Astrocytes were plated at high density in micro-columns with IDs of (FIG. 18A) 1.0 mm, (FIG. 18B) 350 μm, or (FIG. 18C) 180 μm. Astrocytes in (FIG. 18D) 1.0 mm ID micro-columns (n=259 astrocytes from N=6 micro-columns) did not exhibit a preferential alignment, whereas astrocytes cultured in (FIG. 18E) 350 μm ID (n=428; N=10) or (FIG. 18F) 180 μm ID (n=114; N=5) were induced to form an aligned morphology (p<0.05 for each), as measured based on the percentage of processes growing at discrete angles with respect to the long axis of the micro-column (defined as 0°). This suggests that the physical restriction and radius of curvature of the micro-columns dictated the direction of astrocyte process outgrowth and morphology. Scale bars: 100 µm.

Decreasing the Diameter of 3-D) Micro-Columns Increases the Extent of Astrocyte Alignment In order to determine the optimal hydrogel micro-column architecture, constructs of various diameters were tested to determine the curvature regime that would induce maximal astrocyte alignment. Specifically, columns of inner diameters 180 μm, 350 μm, and 1 mm were tested. Phase contrast microscopy revealed that astrocytes grown within 1 mm ID micro-columns did not exhibit any preference in angle of process outgrowth (FIG. 18A), whereas astrocytes grown in 350 μm and 180 μm ID micro-columns demonstrated process alignment with the central axis of the hydrogel (FIGS. 18B,18C). These process alignment data were quantified, revealing that 1 mm ID micro-columns resulted in astrocyte process outgrowth with uniform distribution (FIG. 18D). In stark contrast, the vast majority of astrocyte processes were aligned with the longitudinal axis of the micro-column (FIGS. 18E,18F) in a pattern that statistically deviated from a uniform distribution (p<0.05) when 180 μm and 350 μm ID micro-columns were used. Moreover, 180 μm ID micro-columns were found to produce the highest frequency of maximal alignment (i.e. processes that were 0° from the longitudinal axis) (FIG. 18F). Of note, plating density was kept constant across the various micro-column diameters by adjusting the volume of cell solution in order to fill the entire inner volume. These results demonstrate that micro-column ID dictates the directionality of astrocyte process outgrowth, suggesting that physical parameters such as the angle of curvature of the growth surface influence process turning (or lack thereof).

Figures 19A, 19B, 19C:
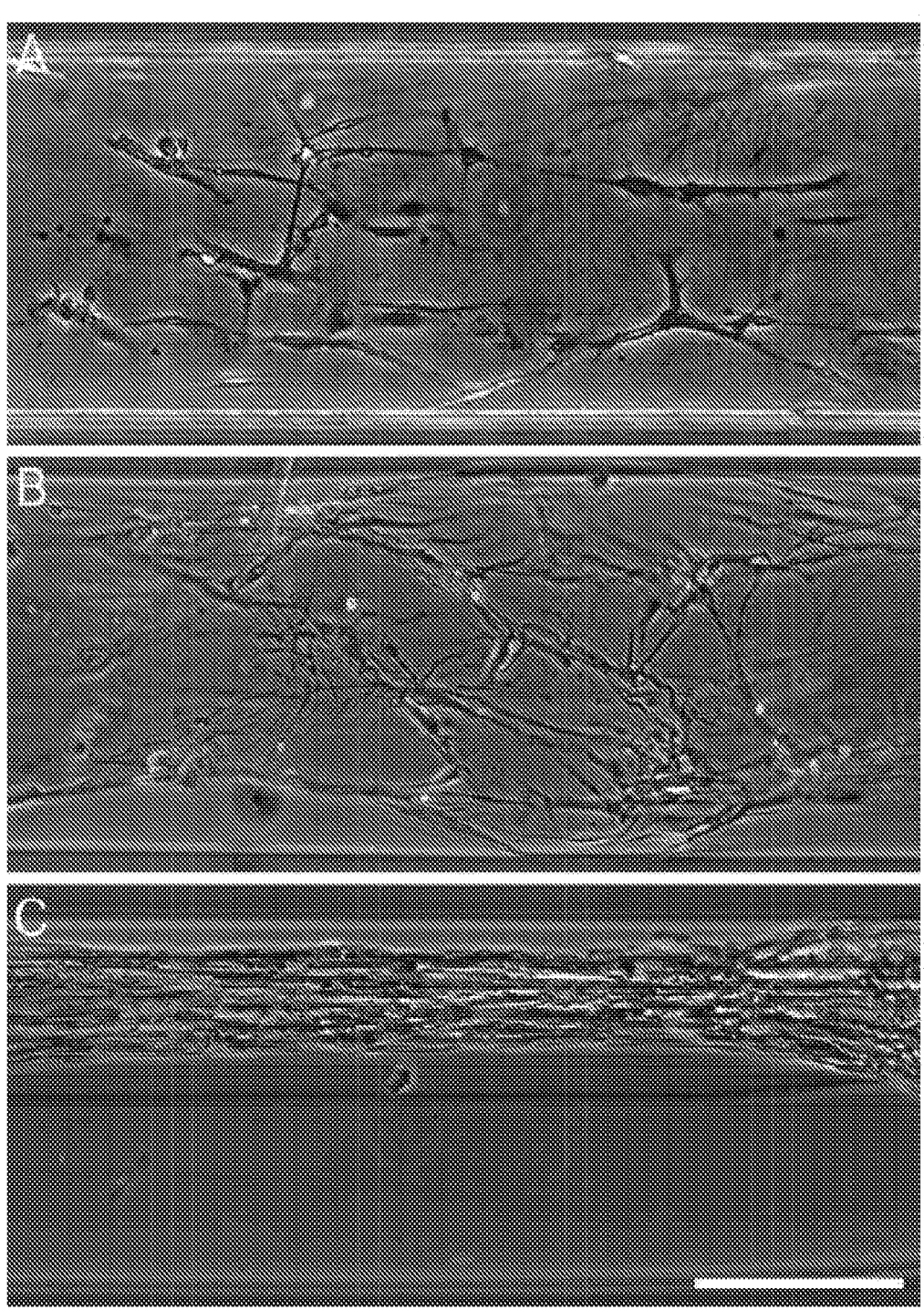
FIGS. 19A-19C are a series of images showing high plating density induced formation of dense, longitudinally aligned bundles of astrocytes. Astrocytes were plated in 350 µm ID hydrogel micro-columns at (FIG. 19A) low.

High Plating Density in 350 μm Diameter Micro-Columns Induces Formation of Longitudinally Aligned Astrocytic Bundles Within 1 DIV Having established that microcolumn dimensions (i.e. diameter/radius of curvature) and core ECM properties (i.e. collagen concentration) significantly affect the extent of astrocyte adhesion and alignment in the microcolumns, further studies were conducted to investigate the effect of seeding density on the extent and robustness of astrocyte alignment. To examine the effect of plating density on astrocyte alignment, astrocytes were plated at "low" (2-3× $10^5$ cells/mL), "medium" (5-6×$10^5$ cells/mL), or "high" (9-12×$10^5$ cells/mL) seeding densities in 350 μm ID micro-columns. Preferential alignment of astrocyte processes was observed across all seeding densities (FIG. 19). Intriguingly, micro-columns plated at a high density were found to produce a tight "bundling" effect of the longitudinally aligned astrocyte somata and processes. This entailed extensive cell and ECM contraction, and presumably ECM remodeling that resulted in the formation of a dense network of closely associated astrocytes in a cable-like architecture generally measuring 50-150 μm in total diameter (FIG. 19C). Notably, these cable-like structures formed extremely rapidly—by 1 DIV—and were maximally aligned with the longitudinal axis of the microcolumn. Conversely, constructs plated at low and medium cell densities, although exhibiting astrocyte alignment, did not exhibit this robust bundling effect. Thus, the extent of cell-cell interactions played an important role in the formation of the aligned cytoarchitecture, as tight astrocytic "bundling" was achieved at high but not low or medium seeding densities.

Immunocytochemistry Confirms Astrocyte Phenotype

Figures 20A, 20B, 20C, 20D:
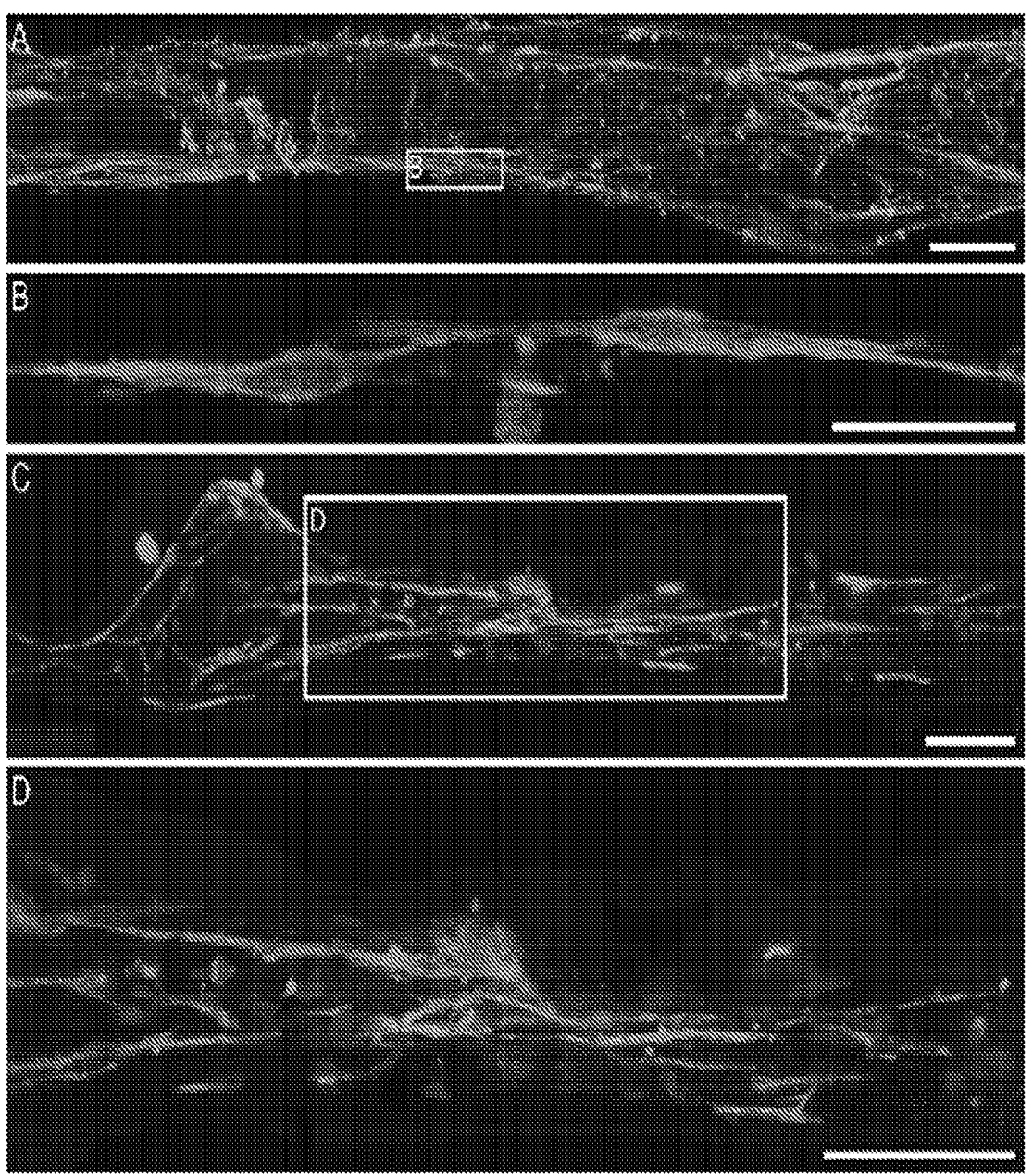
FIGS. 20A-20D are a series of images of immunocytochemistry staining that confirms astrocyte phenotypes within micro-columns. Representative confocal reconstructions of aligned astrocytes are shown that were grown in hydrogel micro-columns with 350 µm ID, stained via immunocytochemistry to denote astrocyte somata/processes (GFAP), possible neuronal contamination (β-tubulin-III), and a Hoechst nuclear counterstain. Astrocytes plated at (FIG. 20A) medium density (N=3 micro-columns) were relatively aligned with the central axis of the micro-column, (FIG. 20B) with many astrocytes exhibiting a bipolar morphology.

Since the objective was to create a tissue engineered construct composed of an aligned astrocyte framework, it was crucial to confirm that the cells aligned in the hydrogel micro-columns were indeed astrocytes. It was also important to eliminate the possibility that the cells had dedifferentiated into a non-glial phenotype or were contaminating neurons. Accordingly, immunocytochemistry techniques were used to label cells for glial fibrillary acidic protein (GFAP), an intermediate filament present in astrocytes, the neuronal marker β-tubulin III, and Hoechst stain to label cell nuclei. High resolution confocal microscopy revealed that the aligned cells were indeed astrocytes, through the widespread expression of GFAP but not β-tubulin III (FIG. 20).

Alignment in 3-D Micro-Column Induces Astrocytic Bi-Polar Morphology

Figures 21A, 21B, 21C, 21D, 21E:
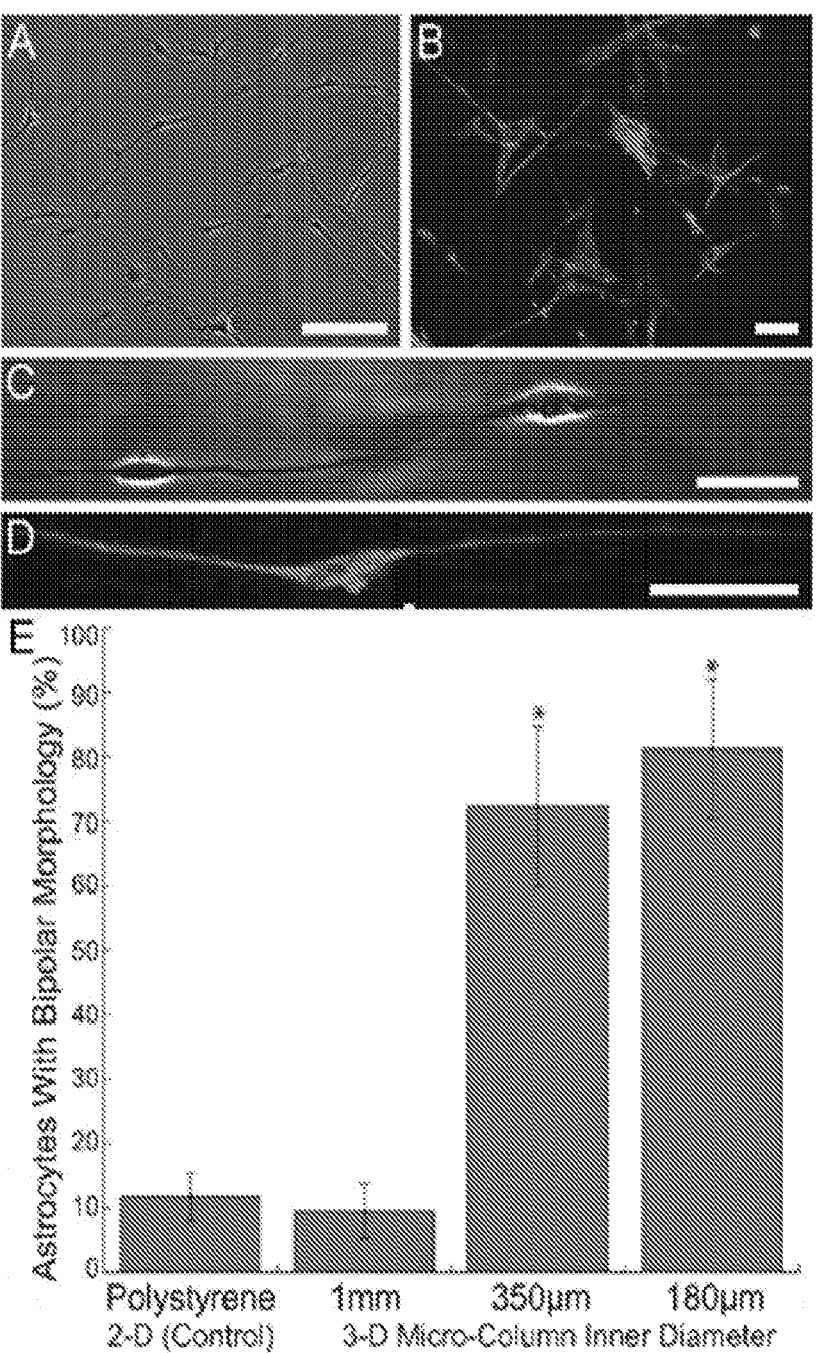
FIGS. 21A-21E are a series of images and graphs showing that growth within small diameter micro-columns induced bipolar morphology in astrocytes.

The effects of micro-column diameter on astrocyte morphology were exam-ined. Typically, astrocytes grown on a 2-D surface display a stellate, multi-process bearing morphology without a preferential direction for process outgrowth (FIGS. 21A-21B). This morphology was also evident in the 1 mm ID micro-columns. However, astrocytes grown in 180 μm or 350 μm hydrogel microcolumns often formed continuous chains of bi-polar astrocytes when plated at low or medium density (FIGS. 21C-21D) or the aforementioned robust longitudinal bundles of bi-polar cells when plated at high density (see FIG. 20). Both the continuous chains and longitudinal bundles of bipolar astrocytes were closely aligned with the longitudinal axis of the micro-column. This finding suggests that the curved geometry of the hydrogel micro-columns dictates the direction of astrocyte process outgrowth as well as the observed cell morphology. To quantify the observation that the smaller diameter micro-columns caused this fundamental shift in morphology, the percentage of bi-polar astrocytes for a particular culture condition was quantified (FIG. 21E). Remarkably, there was over a 7-fold increase in the percentage of bipolar astrocytes when grown within 180 im or 350 im ID micro-columns compared to 1 mm ID micro-columns or growth on planar substrate (p<0.001 for each). Overall, growth within small ID micro-columns induced >70% of the astrocytes to assume a bi-polar morphology, versus ~10% bi-polar in larger micro-columns or on planar surfaces. These results confirm that growth within small diameter micro-columns induced a fundamental alteration in astrocyte morphology.

Figures 22A, 22B, 22C, 22D, 22E, 22F, 22G, 22H, 22I, 22J:
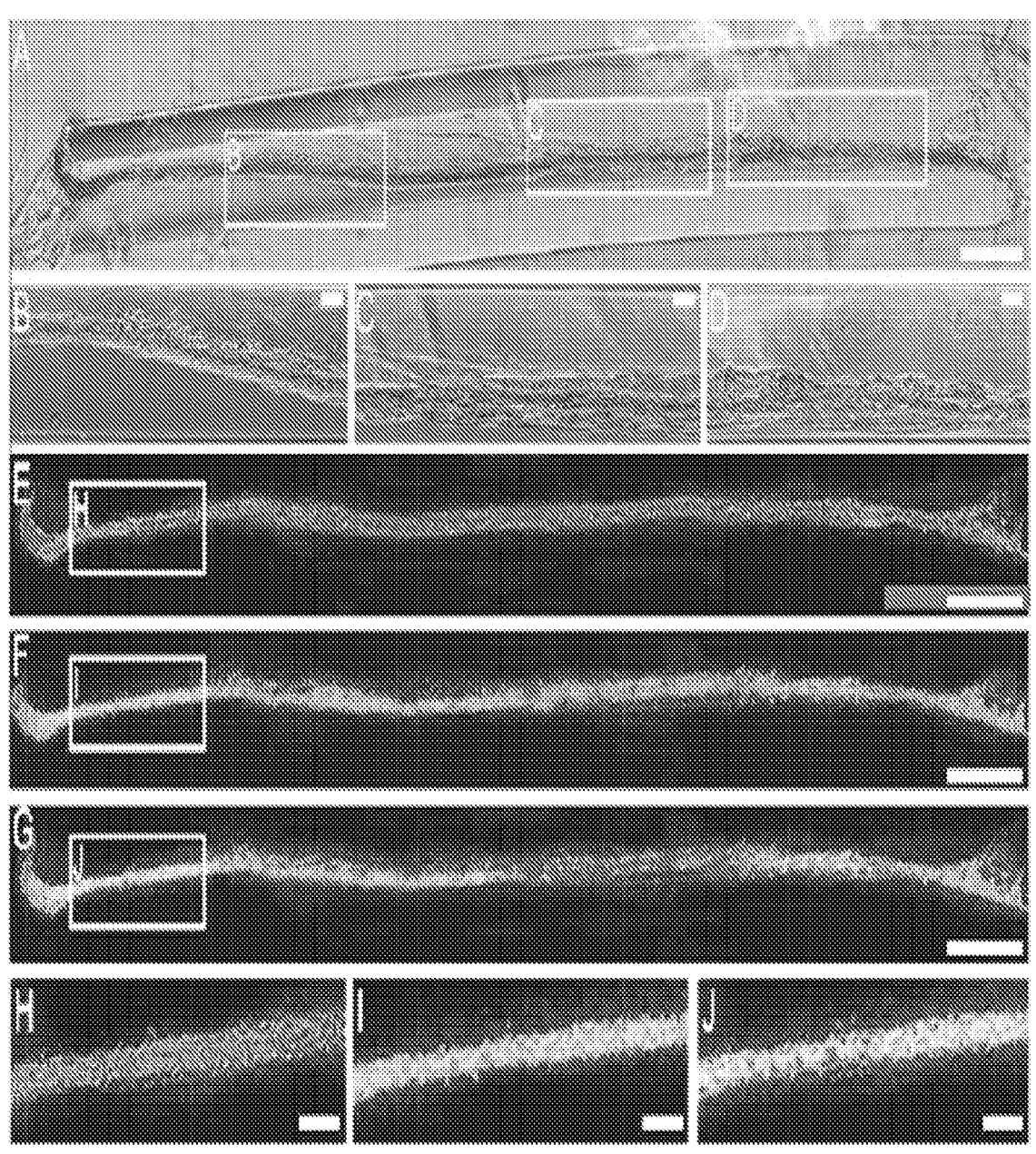
FIGS. 22A-22J are a series of images showing that dense bundles of aligned astrocytes are continuous over the entire length of 5 mm hydrogel micro-columns.

Astrocytic Alignment in Longitudinal Bundles Persists over 16 mm Within Micro-Columns Since the ultimate goal for these aligned astrocyte micro-constructs is to facilitate regeneration following CNS injury, it is critical that these constructs extend over a phys-io-logicaly relevant distance. That is, these constructs must induce robust astrocyte alignment that extends a length sufficient to span an injury site, such as through the glial scar. Here, astrocytes formed a continuous aligned network along the entire length of 5 mm hydrogel mi-cro-columns (FIG. 22). Further, immunocytochemistry was used to confirm that the construct was glial throughout the entire length (FIG. 22E-22J). Moreover, when constructed within longer microcolumns ranging from 20-30 mm in length, astrocytes formed a continuous aligned network of up to 16.8 mm (data not shown). Thus, high density micro-column seeding led to extensive astrocyte-collagen contraction along the length of the micro-column, resulting in continuous, dense 3-D "bundles" of aligned bi-polar astrocytes measuring up to 150 μm in diameter yet extending to a remarkable length of over 16 mm.

Figures 23A, 23B, 23C, 23D, 23E:
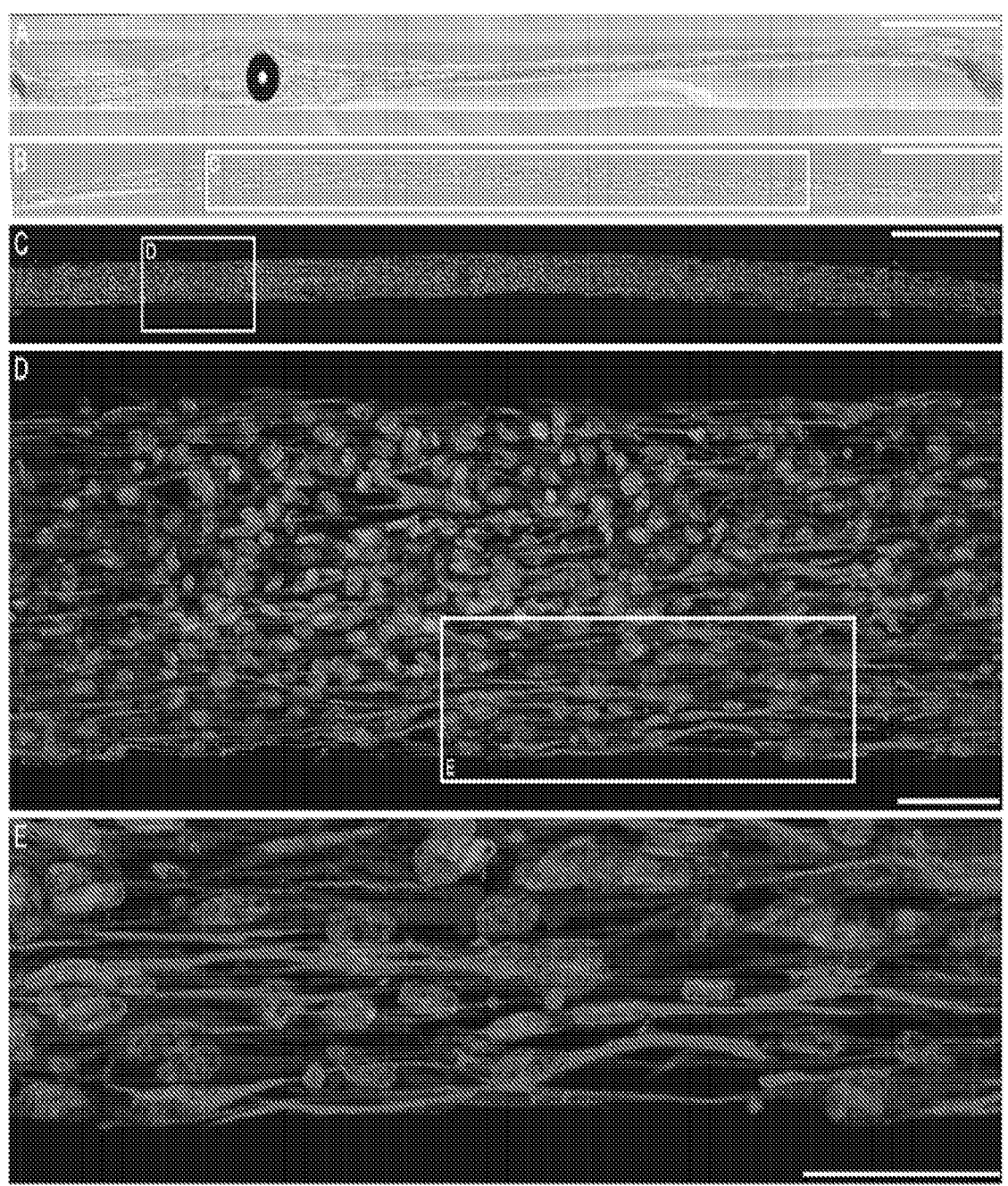
FIGS. 23A-23E are a series of images showing maintenance of aligned longitudinal astrocyte bundles following extraction from microcolumns. Astrocytes plated at high density in micro-columns (300 µm ID; N=7) formed longitudinally aligned astrocytes, which were visualized in phase contrast (FIG. 22A) within the micro-column as well as (FIG. 22B) following extraction from the micro-columns using surgical forceps with placement on a poly-L-lysine coated coverslip.
Figures 24A, 24B:
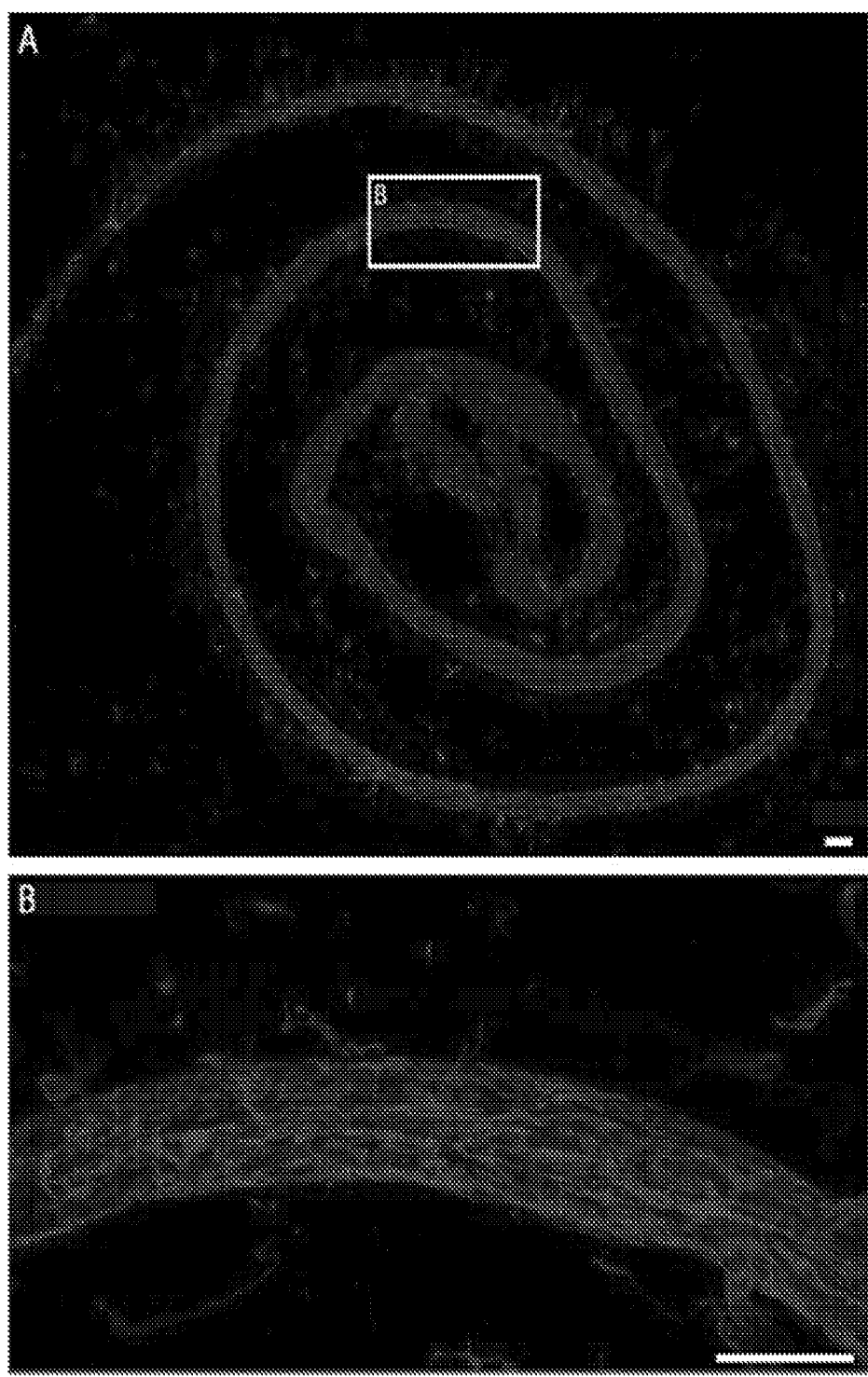
FIGS. 24A-24B are images showing that astrocyte bundles are malleable and resilient upon extraction from micro-columns. Astrocyte bundles extracted from hydrogel micro-columns demonstrate flexibility and durability while maintaining bundled astrocytic cytoarchitecture as shown via immunocytochemistry (GFAP; DAPI) and confocal microscopy.

Bundles of Aligned Bipolar Astrocytes are Maintained upon Extraction from Micro-Columns The structural integrity and stability of the longitudinally aligned astrocytic bundles was assessed by physically pulling them out of the hydrogel columns. The "bundles" of aligned bi-polar astrocytes were maintained despite the forces associated with gripping the end and applying tension for extraction, and once removed, absent the structural support provided by the hydrogel scaffold (FIG. 23). Using surgical forceps, one end was grasped to pull astrocytic bundles out of the micro-columns, where they were often removed in one continuous piece. Bundles were placed onto poly-L-lysine coated coverslips for immunocytochemistry to furthe assess morphology (FIG. 23B-23E). Confocal microscopy revealed that astrocytes maintained a bipolar morphology and remained interconnected to maintain the dense 3-D bundles. These bundles also demonstrated flexibility and maintenance of general alignment despite being physically manipulated while being adhered to coverslips (FIG. 24). This demonstrates the durability and strength of the bundled astrocyte-collagen constructs, which bodes well for in vivo applications following micro-injection.

Figures 25A, 25B, 25C:
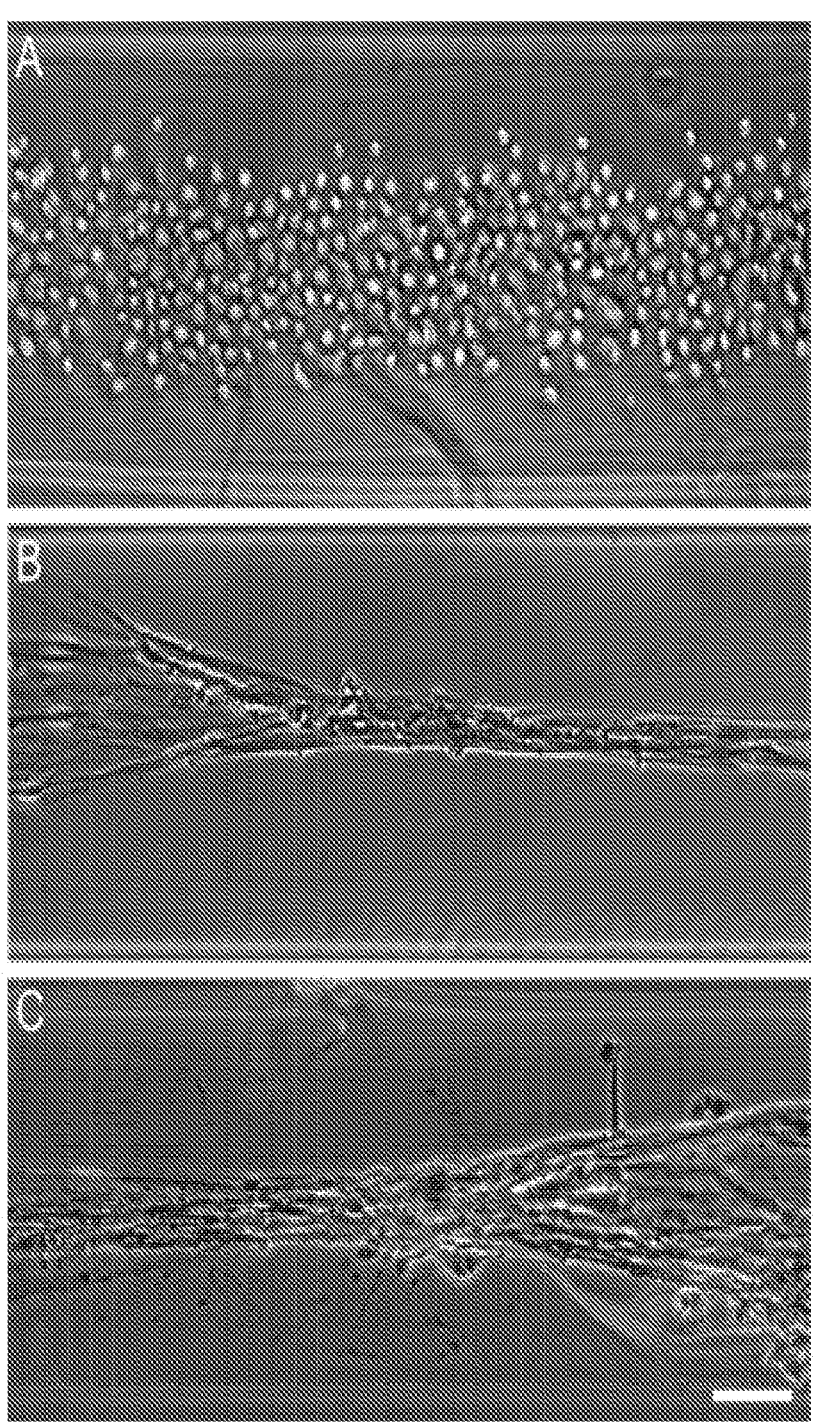
FIGS. 25A-25C are a series of images showing that rapid formation of dense astrocytic bundles is not affected by co-seeding with neurons.

Rapid Formation of Dense. Longitudinally Aligned Astrocytic Bundles is Not Affected By Co-Seeding With Neurons To assess the stability of the aligned astrocyte constructs in the presence of neurons, neurons were co-seeded with astrocytes in 350 μm ID micro-columns. Following initial seeding, astrocytes appeared as sphere-like cells consisting solely of somata and no apparent processes (FIG. 25A). After 1 DIV, astrocytes exhibited a processes bearing morphology and had sufficient time to form the longitudinally aligned bundles by contracting and remodeling the collagen ECM coating the inner surface of the micro-columns (FIG. 25B). This process was unaffected by the presence of neurons, as astrocyte micro-columns co-seeded with neurons also formed the longitudinal astrocytic bundles by 1 DIV (FIG. 25C). This suggests that astrocytes dominate the mechanical process of contracting to form dense bundles, and that the underlying physiological mechanisms are not affected by the presence of neurons.

Figures 26A, 26B, 26C, 26D, 26E, 26F, 26G, 26H, 26I, 26J, 26K:
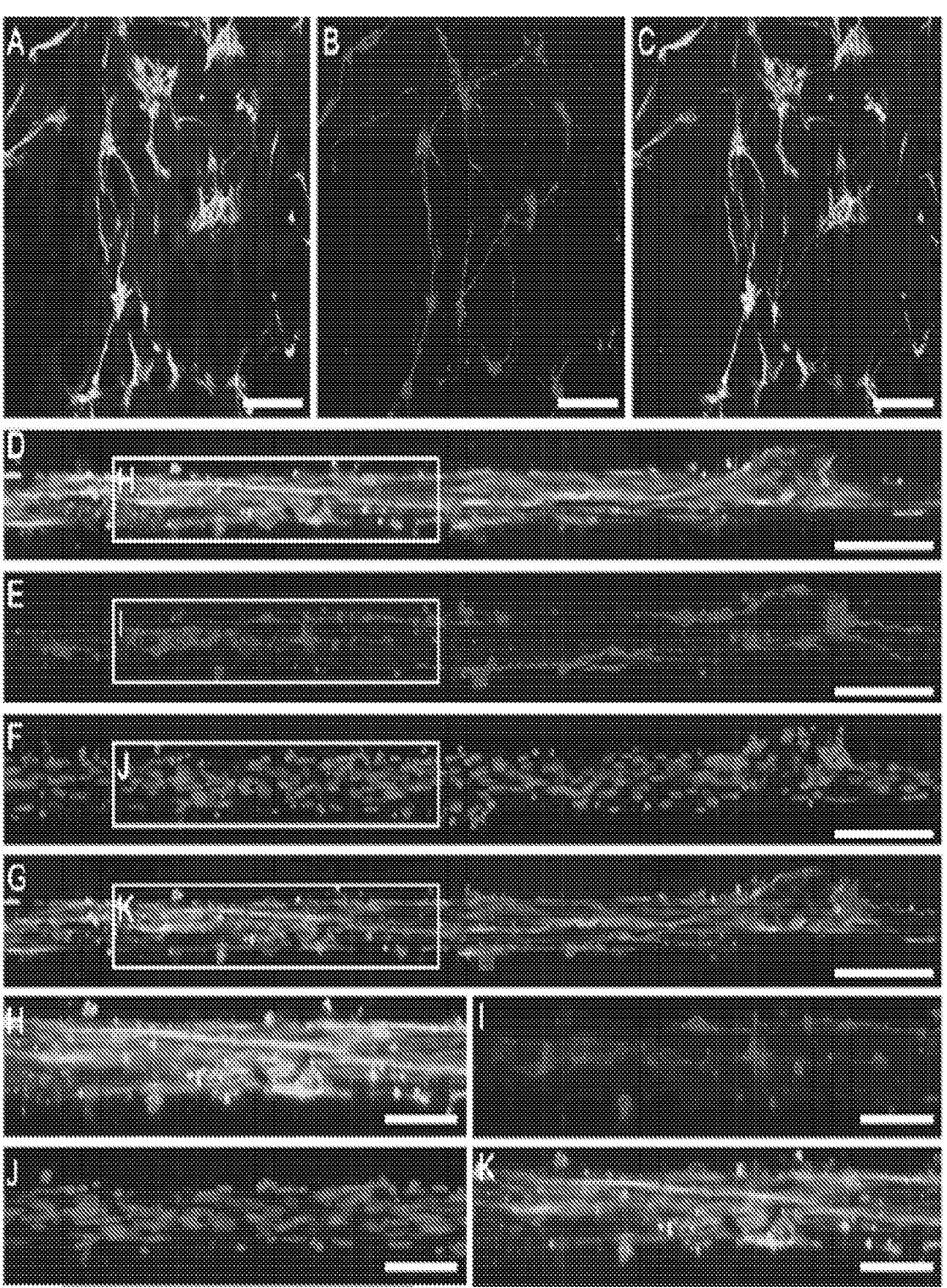
FIGS. 26A-26K are a series of images showing that neurons closely associate and align with longitudinal astrocyte bundles when co-seeded within micro-columns. Neuron-astrocyte co-cultures grown within micro-columns (350 µm ID; N=5) stained via immuno-cytochemistry to denote (FIGS. 26A, 26D, 26H) astrocyte somata/processes (GFAP), (FIGS. 26B, 26E, 26I) neurons (β-tubulin-III), and nuclear counterstain (Hoechst) (FIGS. 26F, 26J) with overlay (FIGS. 26C, 26G, 26K) at 4 DIV.
Figures 27A, 27B:
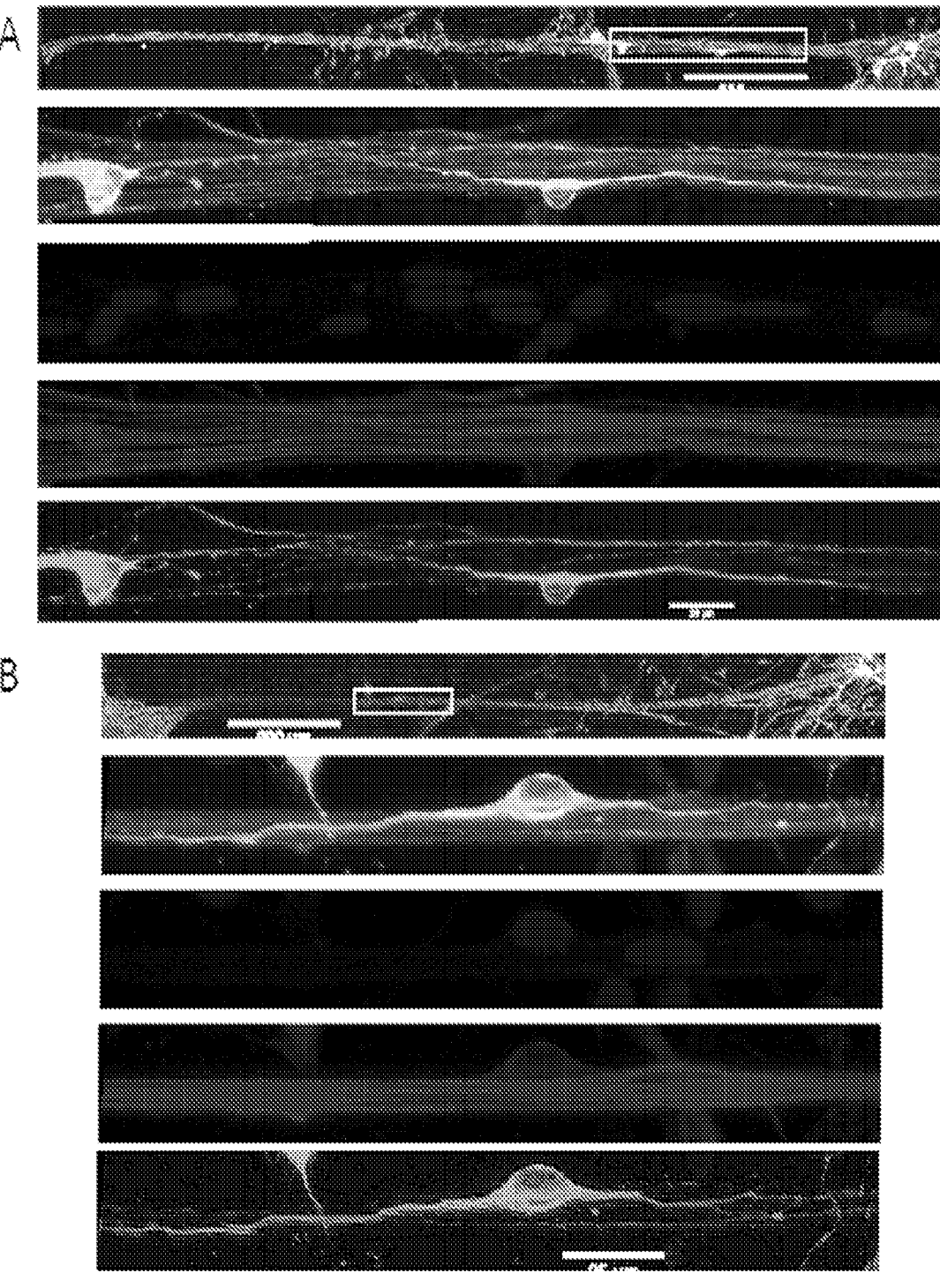
FIGS. 27A-27B are a series of images displaying alignment of neuronal somata and neurites along mechanically elongated astrocytic processes. Immunocytochemistry using antibodies recognizing astrocyte processes (GFAP) and neuronal somata/neurites (TUJ1) with a nuclear counterstain (Hoechst). Individual neurons demonstrated soma and neurite alignment directly along mechanically elongated astrocyte processes.
Figures 28A, 28B, 28C, 28D:
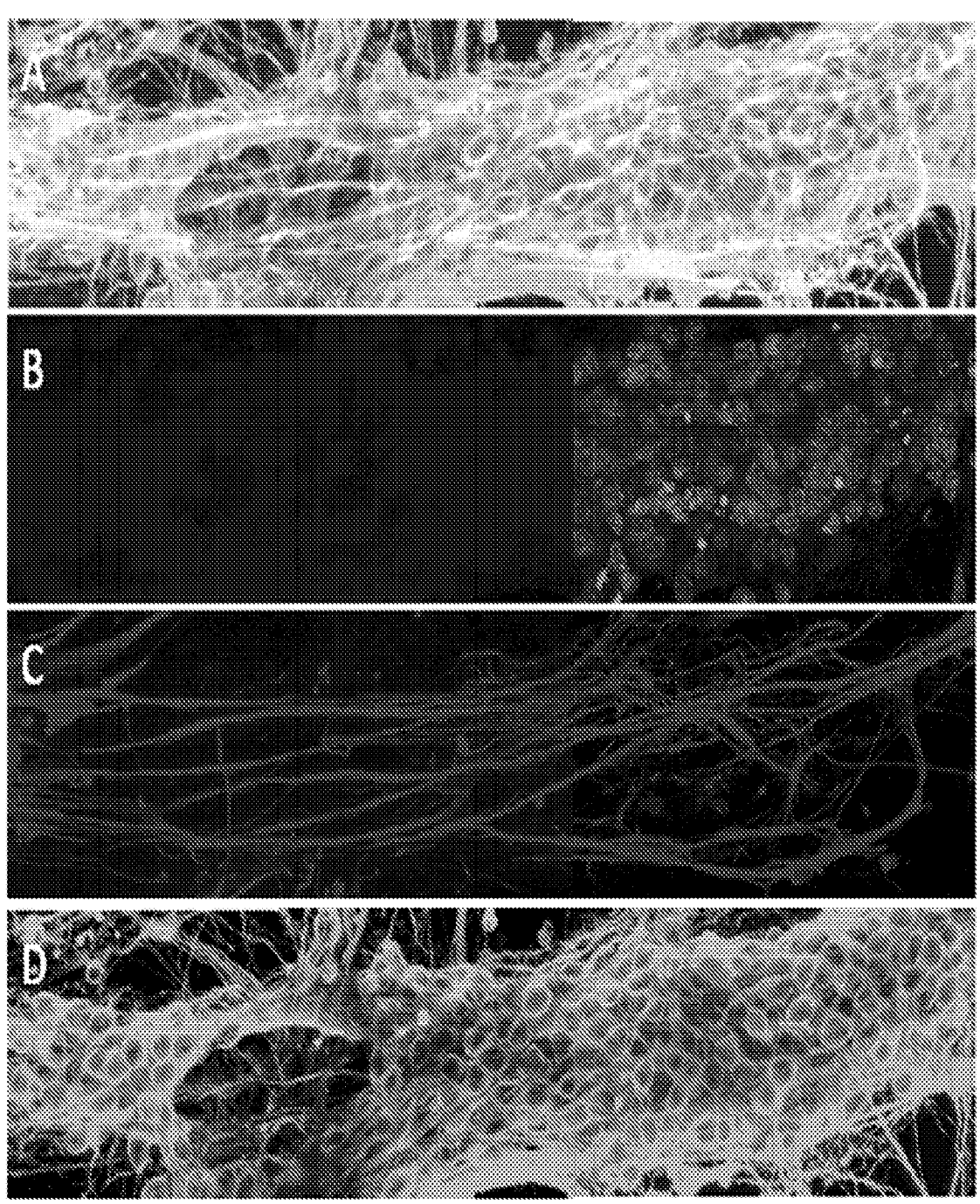
FIGS. 28A-28D are a series of images showing the grouping of neuronal somata along mechanically elongated astrocytic processes. Immunocytochemistry using antibodies recognizing astrocyte processes (GFAP) and neuronal somata/neurites (TUJ1) with a nuclear counterstain (Hoechst). In dense cultures, neuronal somata preferentially lined up along mechanically elongated processes.

Neurons Co-Seeded with Astrocytes in Hydrogel Micro-Columns Survive and Associate with Bundles of Longitudinally Aligned Astrocytes The neuronal-astrocytic co-cultures within micro-columns were grown over several DIV to assess the ability of the aligned astrocyte constructs to support neuron survival and neurite outgrowth. The co-seeded neurons survived and associated closely with the bundles of longitudinally aligned astrocytes. Immunocytochemistry and confocal microscopy revealed that at 4 DIV, neurons co-cultured with astrocytes were directly attached to and extended neurites directly along the longitudinal bundles of aligned astrocytes (FIGS. 26D-26K). These growth patterns were in stark contrast to those observed on a 2-D polystyrene surface, as neuronal adhesion and neurite outgrowth was only colocalized with astrocytes in some cases, and no preferential growth alignment was observed (FIGS. 26A-26C). These findings demonstrate the ability of the aligned astrocyte micro-constructs to support neuron adhesion and survival as well as to provide permissive structural and soluble cues to enable neurite extension directly along the aligned astrocyte somata and processes.

Primary Cortical Neuron Isolation and Culture.

Cerebral cortices were extracted from embryonic day 18 Sprague-Dawley rats and dissociated to isolate cortical neurons. Following dissociation, neurons were resuspended at 2-4×10$^5$ cells/mL in defined co-culture media (Neurobasal® (A neuronal culture medium for cultivating neuronal cells from hippocampus, cortex and other regions of the brain and containing no L-glutamine. L-glutamic acid, or aspartic acid) media+2% B27® supplement (a neuronal culture supplement comprising insulin, transferrin, progesterone, putrescine, selenium, thyroid hormone T3, fatty acids, and antioxidants including vitamin E and glutathione), 1% G-5 supplement (a chemically defined serum free supplement based on Bottenstein's G-5 formulation for growth and expression of glial cells and astrocytes), and 0.25% L-Glutamine). To assess the interaction between neurons and stretched astrocyte processes, approximately 10-20 μL of neuronal solution was added to the cultures containing stretched astrocytes, however the neurons were added some distance away from the processes in order to shield the stretched processes form direct fluid flow forces, as well as to enable assessment of neuronal migration onto the astrocyte processes.

Neurons Survive and Extend Neurites Directly Along Stretched Astrocytic Processes.

Once astrocyte processes had been subjected to tension-induced growth, neurons were added to the culture some distance away from the bundles of stretch-grown processes. Neurons were allowed to grow for 3 DIV, and then the co-cultures were fixed and labeled for GFAP to identify astrocytes, beta-III tubulin to label neurons, and a HOECHST counterstain which labeled nuclei (FIGS. 27A-27B and FIGS. 28A-28D). The stretch-grown astrocytes were clearly seen to be dense bundles of multiple somata and processes. Importantly, seeded neurons were observed readily adhered to these elongated astrocyte process bundles despite being seeded several millimeters away, suggesting migration along the astrocyte processes. Moreover, neurons robustly extended neurites directly along and in alignment with the stretch-grown astrocytic processes (FIG. 9).

Thus, these stretch grown astrocyte somata and processes may be utilized as "living scaffolds" for CNS repair-specifically inducing neuronal precursor migration and/or axonal extension across regions of degeneration. Importantly, these GFAP-positive elongated astrocytic processes were able to successfully promote neurite extension and neuronal migration directly along the stretched process. This demonstrates support and permissiveness for neuronal survival and outgrowth, and bodes well for future applications of this technology in neuroregeneration.

The Materials and Methods used in the performance of the experiments disclosed herein are now described.

Primary Cortical Astrocyte Isolation and Culture. Astrocytes were harvested from postnatal day 0 or day 1 (P0-P1) Sprague Dawley rat pups, as described previously (Cullen et al. 2007, *J Neurosci Res*, 85:3642-51). Briefly, cerebral cortices were extracted and dissociated with 0.25% trypsin+ EDTA followed by 0.15 to 0.30 mg/mL DNase diluted in Hank's balanced salt solution (HBSS) and triturated to separate the tissue. The suspension was then centrifuged at 1000 RPM for 3 min, and cultured in DMEM F-12 media supplemented with 10% fetal bovine serum (FBS), and plated in a flask (Cullen et al. 2007, *J Neurosci Res*, 85:3642-51). Cultures were maintained by mechanically agitating the flasks prior to changing media after 24 hours to dislodge less adherent cell types, leading to a pure astrocyte population over time. The astrocytes were passaged at 90% confluency and re-plated at 30,000 cells/cm$^2$ (McCarthy and de Vellis 1980 *J Cell Biol*, 85:890-902). These methods have previously been shown to produce a nearly pure population of astrocytes (>95%) (Cullen et al. 2007, *J Neurosci Res*, 85:3642-51), which was verified using immunocytochemistry. Between passages 2-8, astrocytes were re-plated in a serum free media to induce a mature glia phenotype as described below. This defined medium consisted of Neurobasal® (A neuronal culture medium for cultivating neuronal cells from hippocampus, cortex and other regions of the brain and containing no L-glutamine. L-glutamic acid, or aspartic acid) media supplemented with 0.25% L-glutamine. 2% B27® supplement (a neuronal culture supplement comprising insulin, transferrin, progesterone, putrescine, selenium, thyroid hormone T3, fatty acids, and antioxidants including vitamin E and glutathione) and 1% G-5 supplement (a chemically defined serum free supplement based on Bottenstein's G-5 formulation for growth and expression of glial cells and astrocytes) at a seeding density ranging from 40.000 to 125.000 cells/cm$^2$. To determine the effect of substrates on astrocyte growth and process formation, four substrates were tested prior to stretch: polystyrene (n=4), thick ACLAR® 33C film (a clear, poly-chloro-trifluoroethylene (PCTFE) film) (199 μm) (n=4), 1 mg/mL MATRIGEL® (a gelatinous protein mixture) on thick ACLAR® 33C film (a clear, poly-chloro-trifluoroethylene (PCTFE) film) (n=4), and 1 mg/mL rat-tail collagen type I on thick ACLAR® 33C film (a clear, poly-chloro-trifluoroethylene (PCTFE) film) (n=4). The MATRIGEL® (a gelatinous protein mixture) and collagen I coatings were extremely thin to ensure sufficient cell adhesion to the membranes such that the mechanical forces would be applied to the cells for eventual stretch-growth studies. Polystyrene and ACLAR® 33C film (a clear, poly-chloro-trifluoroethylene (PCTFE) film) in all groups were coated with 0.05 mg/mL poly-L-lysine (PLL) overnight, then rinsed prior to addition of MATRIGEL® (a gelatinous protein mixture) or collagen I coating.

Figures 1A, 1B, 1C, 1D:
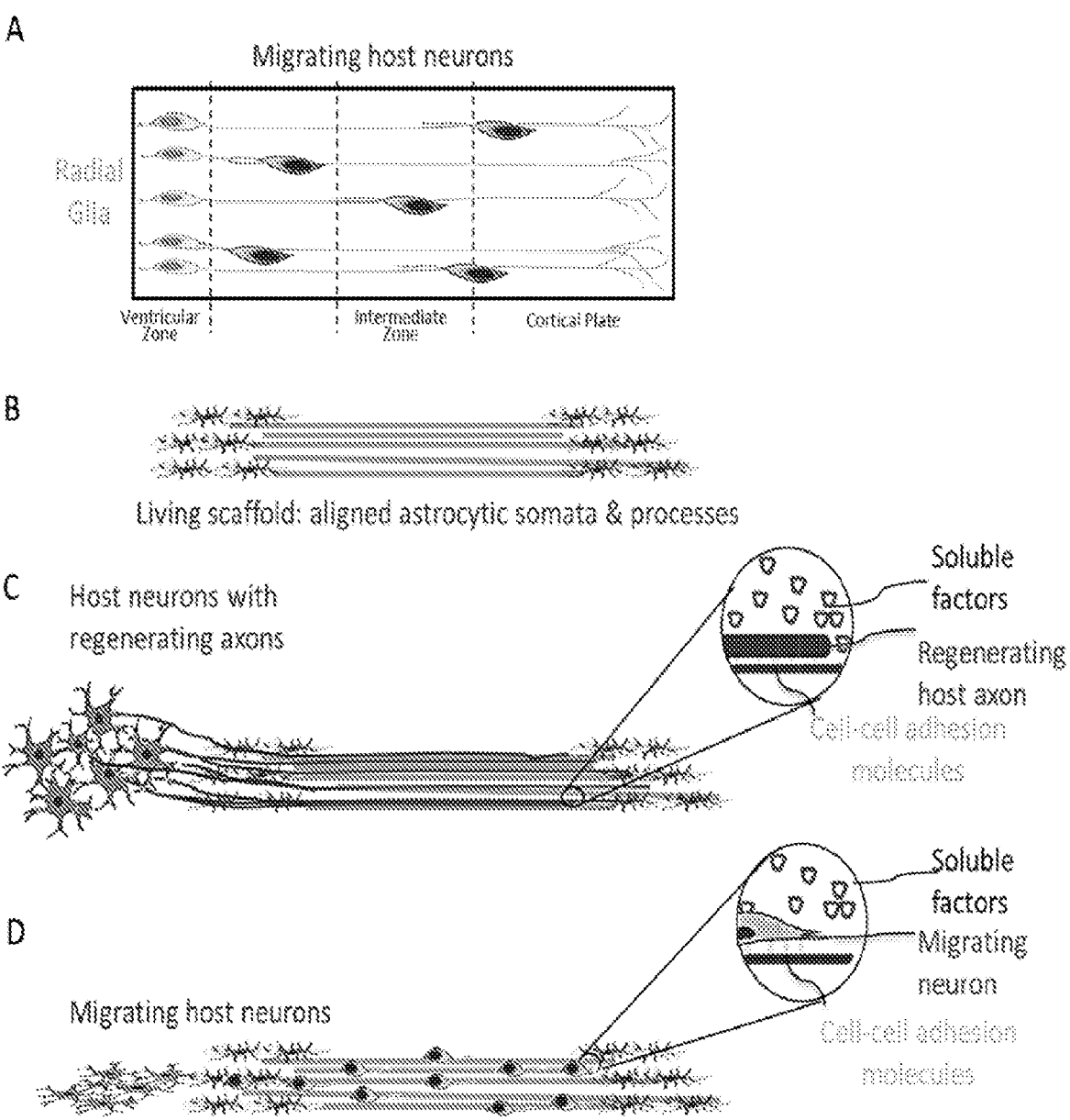
FIG. 1A is a schematic diagram illustrating that radial glia extend along a process from the ventricular zone (VZ) to the cortical plate (CP), and that this long process serves as a living scaffold to direct neuronal migration outward to populate the cortical layers.
FIG. 1B is a schematic diagram illustrating tissue engineered astrocytic living scaffolds consisting of astrocytic somata and stretch-grown, aligned processes.
FIG. 1C is a schematic diagram illustrating a living scaffold comprising long, aligned astrocyte processes to guide axon regeneration.
FIG. 1D is a schematic diagram illustrating a living scaffold comprising long, aligned astrocyte processes to promote neuronal migration to a specified region.
Figures 2A, 2B, 2C, 2D:
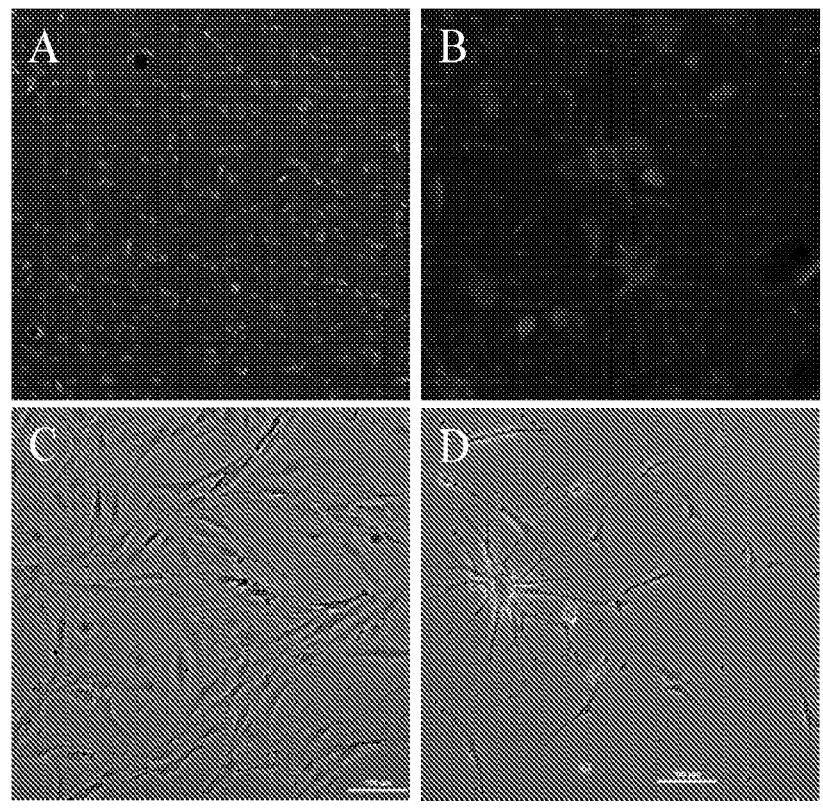
FIGS. 2A-2D, is a panel of images illustrating that a defined astrocyte culture media results in in vivo-like process-bearing morphology.
Figures 3A, 3B, 3C, 3D:
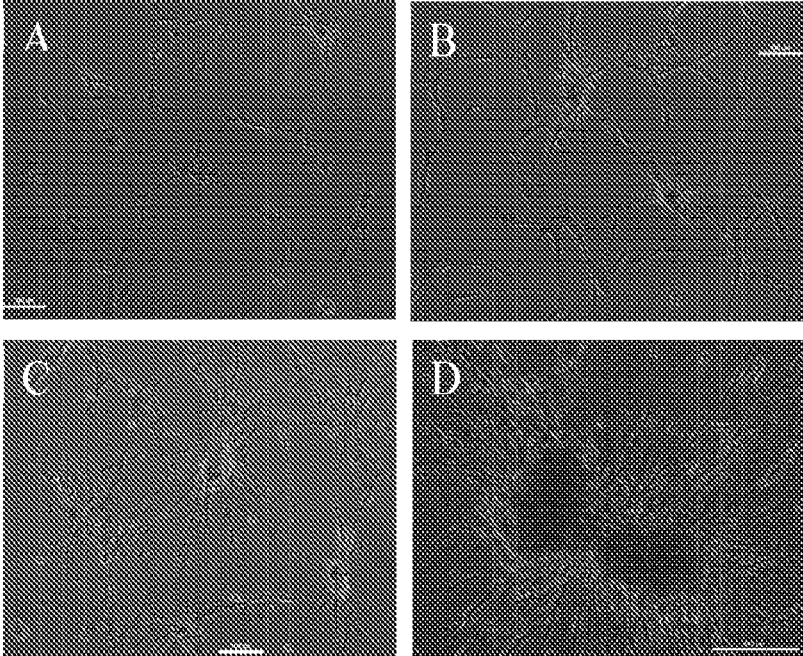
FIGS. 3A-3D, is a panel of images illustrating that matrix optimization results in astrocyte clustering and long processes.

Cortical Astrocyte Culture and Process "Stretch-Growth" Using Custom-Built Mechanobioreactors. Astrocytes were plated in custom-built mechanobioreactors consisting of a custom designed process expansion chamber, linear motion table, stepper motor and controller. The expansion chamber, made of polyether ether ketone (PEEK), served as housing for the cells and consisted of a sealed enclosure with a port for CO$_2$ exchange, removable process stretching frame (known as the carriage), and connecting rods to apply displacements. The carriage was designed to slowly divide two populations of cell somata, thereby stretching their interconnecting processes. The carriage arranges two adjoining substrates in an overlapping fashion on which cells are cultured (FIG. 1). The bottom substrate (199 μm thick), made of optically transparent ACLAR® 33C film (a clear, poly-chloro-trifluoroethylene (PCTFE) film) covered the entire bottom of the stretching frame on which a stationary population of astrocytes was cultured. The plating area within the mechanobioreactor was 15 cm by 8 cm. An overlapping movable substrate (a thinner ACLAR® 33C film (a clear, poly-chloro-trifluoroethylene (PCTFE) film). 19 μm thick) was placed on top of the bottom ACLAR® film (a clear, poly-chloro-trifluoroethylene (PCTFE) film) substrate and served as the substrate for the moving population of cells (referred to as the towing membrane). Processes were mechanically stretched by forces transduced from a stepper motor via attachment to the connecting rods, with the entire assembly mounted to a fixed linear motion table. In turn, the rods displaced the stretching frame with 0.5 μm accuracy. The system was computer controlled by a programmable stepper motor indexer, which was controlled using a custom-written LabView 2011 Run-time Engine program.

Cells were plated at a density of 40.000 to 125.000 cells/cm$^2$ along the interface of the two membranes: the 199 μm thick ACLAR® 33C film (a clear, poly-chloro-trifluoroethylene (PCTFE) film) (SPI supplies) base membrane and the thin 51 μm or ultra-thin 19 μm transparent ACLAR® 33C film (a clear, poly-chloro-trifluoroethylene (PCTFE) film) (SPI supplies) towing membrane that was polished further to reduce thickness. The base and towing membranes were etched with 1N NaOH, and the base membrane was adhered to the bottom of the carriage while the towing membrane was adhered to the towing block, and this entire carriage assembly was placed within the PEEK mechanobioreactors enclosure. The plating area was then coated with 0.05 mg/mL poly-L-lysine (PLL) (BD Biosciences) overnight, rinsed, coated with 1 mg/mL rat tail collagen type I (BD Biosciences) at 37° C. and allowed to incubate overnight. Astrocytes were then plated and allowed to adhere for 45 min before flooding the mechanobioreactor with defined media. Approximately 4-5 days after plating, the mechanobioreactor was connected to the stepper motor and mechanical tension was applied on the cells spanning the membranes by gradually pulling the towing membrane back at a rate of 0.1 mm, 0.3 mm, or 0.5 mm per day (corresponding to 4.17 μm. 12.5 μm, and 20.8 μm per hour).

Microscopic Analysis and Immunocytochemistry. Astrocyte cultures were routinely imaged using phase contrast microscopy techniques on a Nikon Eclipse Ti inverted microscope with Nikon Elements Basic Research software. For immunocytochemistry analysis, astrocyte cultures were fixed in 4% formaldehyde for 30 min, rinsed in phosphate buffered saline (PBS), and permeabilized using 0.3% Triton X100 plus 4% horse serum for 60) min. Primary antibodies were added (in PBS+4% serum solution) at 4° C. for 12 hrs. Primary antibodies to identify astrocytes and neurons were used. Rabbit anti-glial acidic fibrillary protein (GFAP) (Millipore AB5804) was used to identify intermediate filament protein present in astrocytes and mouse anti-β-tubulin III (Sigma C8198) was used to identify an element of microtubules expressed in neurons. After rinsing. Alexa 561 donkey anti-rabbit IgG and Alexa 488 donkey anti-mouse IgG secondary antibodies (1:500 in PBS+4% serum) were added at 18-24° C. for 2 hours. Stretched or static astrocytic cultures were fluorescently imaged using a laser scanning confocal microscope (LSM 710 on an Axio Observer Z1; Zeiss. Oberkochen, Germany). For each culture, multiple confocal z-stacks were digitally captured and analyzed.

Hydrogel Micro-Column Fabrication. All supplies were from Invitrogen (Carlsbad, CA), BD Biosciences (San Jose, CA), or Sigma-Aldrich (St. Louis, MO) unless otherwise noted. Three-dimensional hydrogel micro-columns were designed and fabricated to induce alignment of astrocytes within the central channel of the cylindrical, pipe-like constructs (FIG. 17B). Micro-columns consisted of a thin molded cylinder composed of 3% agarose with a collagenous extracellular matrix (ECM) on the interior to allow for astrocyte adhesion and growth. Briefly, agarose was dissolved in heated Dulbecco's phosphate-buffered saline (DPBS). A needle (Seirin America, Weymouth MA) with diameter ranging from 180 μm to 1 mm was inserted into the center of a microliter glass capillary tube (Drummond Scientific. Broomall PA) with diameter ranging from 798 μm to 2 mm. The agarose solution was drawn via capillary action into the microliter glass capillary tube with the needle in the center. After allowing the agarose to cool and gel, the needle was carefully removed to produce a central column devoid of agarose, creating a hydrogel micro-column with outer diameter (OD) corresponding to the capillary tube diameter (798 μm-2 mm) and an inner diameter corresponding to the needle diameter (180 μm-1 mm). The micro-column was then gently pushed out of the capillary tube into DPBS, trimmed to 5 mm in most cases, and sterilized by UV light for 15 minutes. Subsequently, the micro-columns were cleared of DPBS and 1-3 μL of a collagen ECM solution (0.5-2.0 mg/mL rat-tail collagen type I in defined astrocyte medium, described below) was microinjected into each end. Extra-long micro-columns (10-30 mm) were also generated with 798 μm OD and 300 μm ID, with a proportionate amount of 1 mg/ml collagen micro-injected. Thus, the micro-columns featured a cylindrical agarose shell with a collagen ECM coating the interior surface. The micro-columns were placed in a humidified tissue culture incubator (37° C. 5% $CO_2$) for 1 hour to allow the collagen to polymerize prior to addition of cells as described below:

Primary Cortical Astrocyte Isolation and Culture for Bundle Formation. All procedures involving animals were approved by the Institutional Animal Care and Use Committee of the University of Pennsylvania and followed the National Institutes of Health Guide for the Care and Use of Laboratory Animals (NIH Publications No. 80-23: revised 2011). Primary cortical astrocytes were isolated from postnatal day 0-1 Sprague-Dawley rats pups (Charles River. Wilmington. MA) and dissociated using an established protocol (Cullen et al., *Journal of neuroscience research* 2007: 85:3642-51). Dissociated cells were plated in flasks containing DMEM/F12 supplemented with 10% FBS. Over weeks in culture, a nearly pure population of astrocytes (>95%) was obtained through mechanical agitation to suspend non-astrocytic cell types, media change, and passage, as described, with astrocytic phenotype verified using immunocytochemistry as described below. To seed astrocytes in the micro-columns, dissociated cell solution (2-12× $10^5$ cells/mL) was precisely micro-injected into the micro-columns using a stereoscope for visual guidance. To ensure that the plating density was held constant among micro-columns of different diameters, the astrocyte solution was made to a desired cell density and a sufficient volume was delivered to fill the entire internal canal of the cylinder (e.g., approximately 0.13 μL. 0.48 μL. 3.9 μL for 5 mm long micro-columns with 180 μm. 350 μm, and 1 mm IDs, respectively) as verified by visual inspection. Seeded micro-columns were placed in a humidified tissue culture incubator for 40 minutes to allow cells to adhere. Finally, the culture vessel was flooded with pre-warmed serum-free medium to induce a mature, process-bearing astrocyte phenotype. This defined astrocyte medium consisted of Neurobasal® (A neuronal culture medium for cultivating neuronal cells from hippocampus, cortex and other regions of the brain and containing no L-glutamine. L-glutamic acid, or aspartic acid) medium supplemented with 2% B27® supplement (a neuronal culture supplement comprising insulin, transferrin, progesterone, putrescine, selenium, thyroid hormone T3, fatty acids, and antioxidants including vitamin E and glutathione), 1% G-5 supplement (a chemically defined serum free supplement based on Bottenstein's G-5 formulation for growth and expression of glial cells and astrocytes), and 0.25% L-Glutamine. Constructs were maintained in the humidified tissue culture incubator and half medium changes were performed every 2-3 days in vitro (DIV).

Primary Cortical Neuron Isolation and Culture. Cerebral cortices were extracted from embryonic day 18 Sprague-Dawley rats (Charles River) and dissociated to isolate cortical neurons as described. Following dissociation, neurons were resuspended at 2-4×$10^5$ cells/mL in defined co-culture media (Neurobasal® (A neuronal culture medium for cultivating neuronal cells from hippocampus, cortex and other regions of the brain and containing no L-glutamine. L-glutamic acid, or aspartic acid) media+2% B27® supplement (a neuronal culture supplement comprising insulin, transferrin, progesterone, putrescine, selenium, thyroid hormone T3, fatty acids, and antioxidants including vitamin E and glutathione), 1% G-5 supplement (a chemically defined serum free supplement based on Bottenstein's G-5 formulation for growth and expression of glial cells and astrocytes), and 0.25% L-Glutamine). To assess the ability of the aligned astrocyte constructs to support neuron adhesion, survival, and neurite outgrowth, neurons were seeded by micropipetting 1-2 μL of neuron cell solution at the openings on both ends of micro-columns at 40 minutes following astrocyte plating. These micro-columns were again placed in a humidified tissue culture incubator for 40 minutes to allow cells to adhere and were subsequently flooded with pre-warmed defined co-culture media. Constructs were maintained in the humidified tissue culture incubator and half media changes were performed every 2-3 DIV.

Immunocytochemistry. Immunocytochemistry was performed to confirm astrocyte and neuron phenotype. Briefly, cultures were fixed with 4% formaldehyde for 35 minutes at 18-24° C., rinsed with phosphate buffered saline (PBS), permeabilized and blocked with 4% normal horse serum in 0.1-0.3% Triton X-100 for 60 minutes at 18-24° C., and again rinsed with PBS. Cultures were then incubated in primary antibody solutions at 4° C. for 16 hours. Rabbit anti-glial acidic fibrillary protein (GFAP) (Millipore AB5804) (1:250 in micro-columns or 1:2000 on glass slides) was used to detect the intermediate filament protein in astrocytes, and mouse anti-β-tubulin III (Sigma T8578) (1:500) was used to detect a microtu-bule protein expressed in neurons. Subsequently, cultures were rinsed and incubated in appropriate Alexa secondary antibodies (1:500) in the dark at 18-24° C. for 2 hours. Finally, cultures were incubated in Hoechst solution (Invitrogen H3570) (1:10, 000) for 10 minutes for nuclear staining and subsequently rinsed with and stored in PBS.

Microscopy and Data Acquisition. Cultures were routinely imaged using phase contrast microscopy on a Nikon Eclipse Ti—S microscope with digital image acquisition using a QiClick camera interfaced with Nikon Elements Basic Research software (4.10.01). Cultures were fluorescently imaged using a Nikon AIRSI Laser Scanning Confocal microscope.

Study Design and Statistical Analysis. Multiple studies were conducted to determine the optimal micro-tissue culture conditions to induce astrocyte alignment in the 3-D hydrogel micro-columns, with independent variables including micro-column ID (180 μm, 350 μm, 1 mm), astrocyte plating density ("low": 2-3×$10^5$, "medium": 5-6×$10^5$, "high": 9-12×$10^5$ cells/mL), and the presence of co-seeded neurons. Dependent variables included astrocyte adhesion, survival, process alignment, morphology, density, and phenotype: as well as neuronal adhesion, survival, and neurite outgrowth. As appropriate, traditional 2-D astrocyte cultures on 1 mg/mL collagen I-coated polystyrene were used as controls.

Micro-column ID. Astrocytes were seeded in micro-columns of varying IDs to assess the effects of substrate curvature on astrocyte alignment. At 1 DIV, the extent of astrocyte process alignment was measured relative to the central axis of the hydrogel micro-column (the longitudinal axis of the micro-column was defined as 0) ° with the radial axis defined as) 90°. Angles were measured from phase contrast micrographs using Nikon Elements Basic Research software. This quantitative analysis was performed on astrocytes grown in micro-columns of the following IDs (each at high seeding density): 180 μm (n=114 astrocytes from N=5 micro-columns), 350 μm (n=428; N=10), and 1 mm (n=259; N=6). These data were statistically analyzed using a chi-square goodness-of-fit test (p<0.05 required for significance) with the null hypothesis being that the angles of process outgrowth were governed by a uniform overall distribution (i.e. absence of preferred process directionality).

Astrocyte morphology. The effect of 3-D hydrogel micro-column ID on astrocyte morphology was also assessed in comparison to morphologies present in a traditional 2-D plating environment. Individual astrocytes were analyzed from phase contrast micrographs with morphology scored as "bi-polar" (defined as 2 processes) or "not bi-polar" (defined as >2 processes), and the percentage of astrocytes exhibiting a bi-polar morphology was calculated. This process was completed for astrocytes grown in the following conditions (each at high seeding density): 180 μm ID (n=121 astrocytes from N=6 micro-columns), 350 μm ID (n=134; N=6), and 1 mm ID cultures (n=146 astrocytes; N=5), as well as 2-D sister cultures on polystyrene (n=102; N=5 cultures). These data were statistically analyzed using multiple two-sample t-tests (p<0.05 required for significance).

Astrocyte plating density. Various astrocyte seeding densities were tested in 350 μm ID micro-columns: low (N=15 micro-columns), medium (N=15), and high (N=15). Astrocyte process density and network contraction were qualitatively assessed using phase contrast microscopy over 1-5 DIV.

Extraction of astrocyte bundles from micro-columns. Maintenance of aligned astrocytic bundles outside of the hydrogel micro-columns was assessed (N=10). Following bundle formation in micro-columns (300 μm ID), astrocyte bundles were extracted using surgical forceps and stereoscope for visual guidance. Bundles were adhered to poly-L-lysine coated (20 μg/mL) glass coverslips.

Phenotype of astrocyte-only micro-columns. Confirmation of astrocytic phenotype and the potential presence of neuronal contamination were assessed both within micro-columns (350 μm ID) at medium (N=3 micro-columns) and high (N=21) seeding densities, and following extraction from the micro-columns (as described above) following plating at high seeding density (N=7). Micro-columns were stained using immunocytochemistry and imaged using confocal microscopy as described previously. Astrocytic presence, morphology, and network micro-structure were qualitatively assessed from confocal reconstructions from micro-columns fixed over 1-5 DIV.

Phenotype and growth in astrocyte micro-columns co-seeded with neurons. Neuronal survival, adhesion, and neurite outgrowth were assessed when co-seeded in 350 μm ID micro-columns seeded with astrocytes at high density (N=5). Micro-columns were stained using immunocytochemistry and imaged using confocal microscopy, with neuronal presence, morphology, and neurite alignment qualitatively assessed from confocal reconstructions from micro-columns fixed over 1-5 DIV.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A composition comprising three-dimensional astrocyte bundles of bi-polar and aligned astrocyte processes, wherein the astrocyte bundles are enclosed in a micro-column comprising a biocompatible matrix on the inner surface of the micro-column.

2. The composition of claim 1, wherein the micro-column has an inner diameter ranging from about 0.1 mm to about 0.9 mm, or about 0.3 mm to about 0.35 mm.

3. The composition of claim 2, wherein the inner diameter of the micro-column is about 0.18 mm.

4. The composition of claim 1, wherein the biocompatible matrix is a hydrogel selected from the group consisting of extracellular matrix, collagen, agarose, methylcellulose, biodegradable polyurethanes, and cross-linked hyaluronic acid.

5. The composition of claim 4, wherein the biocompatible matrix comprises collagen and the micro-column comprises agarose.

6. The composition according to claim 1, further comprising astrocytes comprising aligned and elongated astrocyte processes having a length of at least 0.2 millimeters.

7. A composition comprising at least one three-dimensional bundle of bi-polar and aligned astrocyte processes made by a method comprising seeding a micro-column comprising a biocompatible matrix and an inner diameter in a range of about 0.1 mm to about 0.9 mm, or about 0.3 mm to about 0.35 mm with a plurality of astrocytes at a density in a range of $9\text{-}12\times10^5$ cells/ml; and culturing the astrocytes in the micro-column.

8. A method of producing three-dimensional astrocyte bundles of bi-polar aligned astrocyte processes, comprising (i) seeding a micro-column comprising a biocompatible matrix with a plurality of astrocytes at a density in a range of $9\text{-}12\times10^5$ cells/ml.; and (ii) culturing the micro-column so seeded of (i) in a culture medium, wherein the culture medium comprises Neurobasal® (A neuronal culture medium for cultivating neuronal cells from hippocampus, cortex and other regions of the brain and containing no L-glutamine, L-glutamic acid, or aspartic acid), B-27® supplement (a neuronal culture supplement comprising insulin, transferrin, progesterone, putrescine, selenium, thyroid hormone T3, fatty acids, and antioxidants including vitamin E and glutathione), G-5 supplement (a chemically defined serum free supplement based on Bottenstein's G-5 formulation for growth and expression of glial cells and astrocytes) and L-glutamine.

9. The method of claim 8, wherein the micro-column has an inner diameter ranging from about 0.1 mm to about 0.9 mm, or about 0.3 mm to about 0.35 mm.

10. The method of claim 9, wherein the inner diameter of the micro-column is about 0.18 mm.

11. The method of claim 8, wherein the biocompatible matrix is a hydrogel selected from the group consisting of extracellular matrix, collagen, agarose, methylcellulose, biodegradable polyurethanes, and cross-linked hyaluronic acid.

12. The method of claim 11, wherein the biocompatible matrix is collagen and the micro-column comprised agarose.

13. The method of claim 8, wherein the B27® supplement (a neuronal culture supplement comprising insulin, transferrin, progesterone, putrescine, selenium, thyroid hormone T3, fatty acids, and antioxidants including vitamin E and glutathione) in the culture medium is at a concentration ranging from 1% to 5%.

14. The method of claim 8, wherein the G-5 supplement (a chemically defined serum free supplement based on Bottenstein's G-5 formulation for growth and expression of glial cells and astrocytes) in the culture medium is at a concentration ranging from 0.1% to 3%.

15. The method of claim 8, wherein the of L-glutamine in the culture medium is at a concentration ranging from 0.1% to 1.0%.

16. The method of claim 8, wherein the micro-column is co-seeded with neurons.

17. The method of claim 8, wherein the astrocytes so cultured are extracted from the micro-column.

18. A method of producing aligned and elongated astrocyte processes from an astrocyte comprising:

a) culturing an astrocyte in a culture medium, wherein the culture medium comprises Neurobasal® (a neuronal culture medium for cultivating neuronal cells from hippocampus, cortex and other regions of the brain and containing no L-glutamine, L-glutamic acid or aspartic acid), B-27® supplement (a neuronal culture supplement comprising insulin, transferrin, progesterone, putrescine, selenium, thyroid hormone T3, fatty acids, and antioxidants including vitamin E and glutathione), G-5 supplement (a chemically defined serum free supplement based on Bottenstein's G-5 formulation for growth and expression of glial cells and astrocytes) and L-glutamine;

b) plating the cultured astrocyte onto an overlying membrane and an underlying membrane so that the cultured astrocyte adheres to both membranes, wherein the overlying membrane or the underlying membrane is selected from polystyrene, ACLAR® film (a clear, poly-chloro-trifluoroethylene (PCTFE) film), collagen coated ACLAR® film (a clear, poly-chloro-trifluoroethylene (PCTFE) film) or MATRIGEL® (a gelatinous protein mixture) coated ACLAR® film (a clear, poly-chloro-trifluoroethylene (PCTFE) film), and wherein the overlying membrane is a towing membrane and the underlying membrane is a stationary membrane, or wherein the underlying membrane is the towing membrane and the overlying membrane is the stationary membrane; and c) moving one of the two membranes—the overlying membrane and the underlying membrane-across the other under an ex vivo force at a stretching rate of 0.1-0.5 millimeter/day so that astrocyte processes from the astrocyte are stretched and aligned along the ex vivo force.

19. The method of claim 18, wherein the B-27® supplement (a neuronal culture supplement comprising insulin, transferrin, progesterone, putrescine, selenium, thyroid hormone T3, fatty acids, and antioxidants including vitamin E and glutathione) in the culture medium is at a concentration ranging from 1% to 5%.

20. The method of claim 18, wherein the G-5 supplement (a chemically defined serum free supplement based on Bottenstein's G-5 supplement (a chemically defined serum free supplement based on Bottenstein's G-5 formulation for growth and expression of glial cells and astrocytes) formulation for growth and expression of glial cells and astrocytes) in the culture medium is at a concentration ranging from 0.1% to 3%.

21. The method of claim 18, wherein the L-glutamine in the culture medium is at a concentration ranging from 0.1% to 1.0%.

22. The method of claim 18, wherein the ex vivo force is a mechanical force.

23. The method of claim 22, wherein the mechanical force is generated from a device comprising structures of a stepper motor, an adaptor and a mechano-bioreactor, and wherein the mechano-bioreactor consists of a towing block attached to elongator rods that are connected to a motorized stepper that gradually pulls the towing blocks backward as shown in FIG. 8B-8D.

24. The method of claim 18, wherein the astrocyte processes are elongated to greater than 1 millimeter in length, or to greater than 2 millimeters in length.

25. The method of claim 18, wherein the towing membrane and/or the stationary membrane are selected from collagen coated ACLAR® film (a clear, poly-chloro-trifluoroethylene (PCTFE) film) or MATRIGEL® (a gelatinous protein mixture) coated ACLAR® film (a clear, poly-chloro-trifluoroethylene (PCTFE) film).

* * * * *